(12) United States Patent
Brown et al.

(10) Patent No.: US 8,333,995 B2
(45) Date of Patent: *Dec. 18, 2012

(54) PROTEIN MICROSPHERES HAVING INJECTABLE PROPERTIES AT HIGH CONCENTRATIONS

(75) Inventors: Larry Brown, Newton, MA (US); Vered Bisker-Leib, Woburn, MA (US); Debra LaFreniere, Dighton, MA (US); John McGeehan, Woodbury, NJ (US); Julia Rashba-Step, Newton, MA (US); Terrence Scott, Winchester, MA (US)

(73) Assignees: Baxter International, Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/127,704

(22) Filed: May 12, 2005

(65) Prior Publication Data

US 2006/0024379 A1 Feb. 2, 2006

Related U.S. Application Data

(63) Continuation-in-part of application No. 10/894,410, filed on Jul. 19, 2004, now abandoned.

(60) Provisional application No. 60/570,274, filed on May 12, 2004.

(51) Int. Cl.
*A61K 39/395* (2006.01)
(52) U.S. Cl. ....................................................... 424/491
(58) Field of Classification Search .................. 424/491
See application file for complete search history.

(56) References Cited

U.S. PATENT DOCUMENTS

| | | | |
|---|---|---|---|
| 3,737,337 A | 6/1973 | Schnoring et al. |
| 3,891,570 A | 6/1975 | Fukushima et al. |
| 4,389,330 A | 6/1983 | Tice et al. |
| 4,530,840 A | 7/1985 | Tice et al. |
| 4,584,894 A | 4/1986 | Fogelberg |
| 4,652,441 A | 3/1987 | Okada et al. |
| 4,728,721 A | 3/1988 | Yamamoto et al. |
| 4,818,542 A | 4/1989 | DeLuca et al. |
| 4,849,228 A | 7/1989 | Yamamoto et al. |
| 4,861,627 A | 8/1989 | Mathiowitz et al. |
| 4,897,268 A | 1/1990 | Tice et al. |
| 4,904,479 A | 2/1990 | Illum |
| 4,917,893 A | 4/1990 | Okada et al. |
| 5,075,109 A | 12/1991 | Tice et al. |
| 5,102,872 A | 4/1992 | Singh et al. |
| 5,149,543 A | 9/1992 | Cohen et al. |
| 5,213,812 A | 5/1993 | Ruiz |
| 5,300,464 A | 4/1994 | Rittler |
| 5,330,767 A | 7/1994 | Yamamoto et al. |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Tice et al. |
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,482,927 A | 1/1996 | Maniar et al. |
| 5,543,158 A | 8/1996 | Gref et al. |
| 5,556,642 A | 9/1996 | Kobayashi et al. |
| 5,575,987 A | 11/1996 | Kamei et al. |
| 5,578,709 A * | 11/1996 | Woiszwillo ................... 530/410 |
| 5,599,719 A | 2/1997 | Woiszwillo |
| 5,603,961 A | 2/1997 | Suzuki et al. |
| 5,631,020 A | 5/1997 | Okada et al. |
| 5,631,021 A | 5/1997 | Okada et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,665,428 A * | 9/1997 | Cha et al. ................... 427/213.3 |
| 5,667,808 A | 9/1997 | Johnson et al. |
| 5,851,451 A | 12/1998 | Takechi et al. |
| 5,891,478 A | 4/1999 | Johnson et al. |
| 5,932,248 A | 8/1999 | Chen et al. |
| 5,945,126 A | 8/1999 | Thanoo et al. |
| 5,981,719 A | 11/1999 | Woiszwillo et al. |
| 5,989,463 A | 11/1999 | Tracy et al. |
| 6,036,976 A | 3/2000 | Takechi et al. |
| 6,042,792 A | 3/2000 | Shefer et al. |

(Continued)

FOREIGN PATENT DOCUMENTS

CA 2157793 A1 9/1994

(Continued)

OTHER PUBLICATIONS

Falkenberg J. Clin. Chem. Biochem. 1984, 22:867-882.*

(Continued)

*Primary Examiner* — Karen Cochrane Carlson
(74) *Attorney, Agent, or Firm* — Marshall, Gerstein & Borun LLP

(57) ABSTRACT

The present invention relates to compositions of methods of making and compositions small compositions of particles of an active agent. In accordance with the method of production, the active agent is dissolved in an aqueous or aqueous-miscible solvent containing a dissolved phase-separation enhancing agent (PSEA) to form a solution in a single liquid phase. The solution is subjected to a liquid-solid phase separation to cause the active agent to form small spherical that are substantially amorphous or non-crystalline and are injectable through fine gauge needles at high concentrations. The invention has special application for higher molecular weight proteins.

81 Claims, 38 Drawing Sheets

U.S. PATENT DOCUMENTS

| | | | |
|---|---|---|---|
| 6,051,259 | A | 4/2000 | Johnson et al. |
| 6,063,910 | A | 5/2000 | Debeneditti |
| 6,090,925 | A | 7/2000 | Woiszwillo et al. |
| 6,120,787 | A | 9/2000 | Gustafsson et al. |
| 6,153,211 | A | 11/2000 | Hubbell et al. |
| 6,252,055 | B1 | 6/2001 | Relton et al. |
| 6,267,958 | B1 | 7/2001 | Andya et al. |
| 6,268,053 | B1 | 7/2001 | Woiszwillo et al. |
| 6,270,795 | B1 | 8/2001 | Jones et al. |
| 6,270,802 | B1 | 8/2001 | Thanoo et al. |
| 6,361,798 | B1 | 3/2002 | Thanoo et al. |
| 6,395,302 | B1 | 5/2002 | Hennink et al. |
| 6,455,074 | B1 | 9/2002 | Tracy et al. |
| RE37,872 | E | 10/2002 | Franks et al. |
| 6,458,387 | B1 | 10/2002 | Scott et al. |
| 6,500,448 | B1 | 12/2002 | Johnson et al. |
| 6,506,410 | B1 | 1/2003 | Park et al. |
| 6,596,316 | B2 | 7/2003 | Lyons et al. |
| 6,616,949 | B2* | 9/2003 | Jonsson et al. ............. 424/501 |
| 6,630,169 | B1 | 10/2003 | Bot et al. |
| 6,645,525 | B1 | 11/2003 | Woiszwillo et al. |
| RE38,385 | E | 1/2004 | Hatley et al. |
| 6,749,866 | B2 | 6/2004 | Bernstein et al. |
| 6,814,980 | B2 | 11/2004 | Levy et al. |
| 6,830,737 | B2 | 12/2004 | Ramstack |
| 6,849,259 | B2 | 2/2005 | Haurum et al. |
| 6,861,064 | B1 | 3/2005 | Laakso et al. |
| 6,875,432 | B2 | 4/2005 | Liu et al. |
| 7,132,100 | B2* | 11/2006 | Oliver et al. ............. 424/130.1 |
| 8,075,919 | B2* | 12/2011 | Brown et al. ............. 424/489 |
| 2001/0002261 | A1 | 5/2001 | Morrison et al. |
| 2002/0009453 | A1 | 1/2002 | Haurum et al. |
| 2002/0045571 | A1 | 4/2002 | Liu et al. |
| 2002/0136719 | A1 | 9/2002 | Shenoy et al. |
| 2002/0146459 | A1 | 10/2002 | Levy et al. |
| 2003/0007990 | A1 | 1/2003 | Blankenship et al. |
| 2003/0059474 | A1* | 3/2003 | Scott et al. ............. 424/491 |
| 2003/0064033 | A1 | 4/2003 | Brown et al. |
| 2003/0211153 | A1 | 11/2003 | Johnson et al. |
| 2004/0014698 | A1 | 1/2004 | Hortelano et al. |
| 2004/0039171 | A1 | 2/2004 | Matsumoto et al. |
| 2004/0043076 | A1 | 3/2004 | Dulieu et al. |
| 2004/0185091 | A1 | 9/2004 | Truong et al. |
| 2004/0197324 | A1 | 10/2004 | Liu et al. |
| 2004/0219224 | A1 | 11/2004 | Yakovlevsky et al. |
| 2005/0053666 | A1 | 3/2005 | Tzannis et al. |
| 2005/0142201 | A1 | 6/2005 | Rashba-Step et al. |
| 2005/0142205 | A1 | 6/2005 | Rashba-Step et al. |
| 2005/0142206 | A1 | 6/2005 | Brown et al. |
| 2005/0147687 | A1 | 7/2005 | Rashba-Step et al. |
| 2005/0158303 | A1 | 7/2005 | Liu et al. |
| 2005/0170005 | A1 | 8/2005 | Rashba-Step et al. |
| 2005/0175603 | A1 | 8/2005 | Liu et al. |
| 2005/0180967 | A1 | 8/2005 | Haurum et al. |
| 2005/0202072 | A1 | 9/2005 | Ruch-Rasmussen et al. |
| 2005/0233945 | A1 | 10/2005 | Brown et al. |
| 2005/0271731 | A1 | 12/2005 | Suzuki et al. |
| 2006/0002862 | A1 | 1/2006 | Truong-Le et al. |
| 2006/0127395 | A1 | 6/2006 | Arvinte et al. |
| 2006/0182740 | A1 | 8/2006 | Yang et al. |
| 2007/0023776 | A1 | 2/2007 | Zakgeym et al. |
| 2007/0065440 | A1 | 3/2007 | Tomlinson et al. |
| 2007/0122411 | A1 | 5/2007 | Matheus et al. |
| 2007/0172475 | A1 | 7/2007 | Matheus et al. |
| 2007/0172479 | A1 | 7/2007 | Warne et al. |

FOREIGN PATENT DOCUMENTS

| | | |
|---|---|---|
| CA | 2157793 C | 9/1994 |
| EP | 248531 A2 | 1/1986 |
| EP | 248531 A3 | 1/1986 |
| EP | 0564061 B1 | 10/1993 |
| EP | 809110 A1 | 11/1997 |
| EP | 1060741 A1 | 12/2000 |
| EP | 1173151 B1 | 1/2002 |
| EP | 1283720 B1 | 2/2003 |
| EP | 1801123 A2 | 6/2004 |
| EP | 0907378 B1 | 2/2006 |
| JP | 11-302156 A | 11/1999 |
| JP | 2006219455 | 8/2006 |
| RU | 2147226 | 4/2000 |
| WO | WO 94/20856 | 9/1994 |
| WO | WO-94/24263 | 10/1994 |
| WO | WO/9500128 | 5/1995 |
| WO | WO-96/03978 | 2/1996 |
| WO | WO-96/08289 | 3/1996 |
| WO | WO-96/09814 | 4/1996 |
| WO | WO-96/38153 A1 | 12/1996 |
| WO | WO-97/45140 | 12/1997 |
| WO | WO-99/55310 A1 | 11/1999 |
| WO | WO-00/00176 | 1/2000 |
| WO | WO-00/62759 | 10/2000 |
| WO | WO-01/89563 | 11/2001 |
| WO | WO-02/39985 A1 | 5/2002 |
| WO | WO-02/43580 | 6/2002 |
| WO | WO-02/055059 A2 | 7/2002 |
| WO | WO-02/072636 | 9/2002 |
| WO | WO-02/096457 | 12/2002 |
| WO | WO 03/000014 A2 | 1/2003 |
| WO | WO-03/015750 | 2/2003 |
| WO | WO-04/001007 | 12/2003 |
| WO | WO-2004/058156 | 7/2004 |
| WO | WO-2004/060343 | 7/2004 |
| WO | WO 2005001355 A1 | 6/2005 |
| WO | WO 2005077414 A1 | 8/2005 |
| WO | WO-2005/123131 | 12/2005 |
| WO | WO-2006/031560 | 3/2006 |
| WO | WO-2006/065746 | 6/2006 |
| WO | WO-2006/112838 | 10/2006 |
| WO | WO-2007/076062 | 7/2007 |

OTHER PUBLICATIONS

Huber Klin. Wochenschr. 1998, 58:1217-1231.*
Diehl et al. 2001; A good practice guide to the administration of substances and removal of blood, including routes and volumes. Journal of applied Toxicology 21: 15-33.*
Ahn, C.H, et al., Biodegradable poly(ethylenimine) for plasmid DNA delivery, Journal of Controlled Release, 2002, vol. 80(1-3), pp. 273-282.
Brazeau, G.A., et al., In vitro myotoxicity of selected cationic macromolecules used in non-viral gene delivery, Pharmaceutical Research, 1998, vol. 15(5), pp. 680-684.
Brown, et al., "Pulmonary Delivery of Novel Insulin Microspheres", Proceed, Respiratory Drug Delivery VIII, DHI Publishing, Raleigh, N.C., 2002, pp. 431-434.
Brown, et al., PROMAXX Microsphere Characterization, in Proceed. of Resp. Drug. Del. IX, 2004, pp. 477-479.
Bustami, et al., Generation of micro-particles of proteins for aerosol delivery using high pressure modified carbon dioxide, Pharmaceutical Research, Nov. 2000, vol. 17, No. 11, pp. 1360-1366.
Chu, C.J., et al., Efficiency of cytoplasmic delivery by pH-sensitive liposomes to cells in culture, Pharm. Res., 1990, vol. 7, pp. 824-834.
Moghimi, "Chemical camouflage of nanospheres with a poorly reactive surface: towards development of stealth and target-specific nanocarriers", Biochimica et Biophysica Acta, vol. 1590, pp. 131-139, 2000.
Morita, et al., Formation and Isolation of Spherical Fine Protein Microparticles Through Lyophilization of Protein-Poly (ethylene Glycol) Aqueous Mixture, Pharmaceutical Research, 2000, vol. 17, No. 11.
Rashba-Step et al., Albumin Microspheres as Drug Delivery Vehicle for Multiple Routes of Administration, Proceed. Int'l. Symp. Control. Rel. Bioact. Materials., 2001, vol. 28.
Sah, H.K., et al.,Biodegradable microcapsules prepared by a w/o/w technique: effects of shear force to make a primary w/o emulsion on their morphology and protein release, J. of Microencapsulation, 1995, vol. 12(1), pp. 59-69.
Sinha, et al., Biodegradable microspheres for protein delivery, Journal of Controlled Release, 2003, vol. 90, pp. 261-280.
Yang, et al., Crystalline monoclonal antibodies for subcutaneous delivery, Proc. Natl. Acad. Sci (USA), Jun. 10, 2003, vol. 100, No. 12, pp. 6934-6939.

Zhao, Q., et al., Modulation of oligonucleotide-induced immune stimulation by cyclodextrin analogs.Biochem. Pharmacol., 1996, vol. 52, pp. 1537-1544.
Report of the International Searching Authority PCT/US04/016651 pp. 1-3, Sep. 5, 2005.
Report of the International Searching Authority PCT/US04/23182 pp. 1-3, Nov. 3, 2005.
Opinion of the International Searching Authority PCT/US04/016651 pp. 1-6, Sep. 5, 2005.
Opinion of the International Searching Authority PCT/US04/23182 pp. 1-3, Nov. 3, 2005.
US 5,849,884, 12/1988, Woiszwillo et al. (withdrawn).
Eliassi et al. Densities of Poly(ethylene glycol) + Water Mixtures in the 298.15-328.15 K Temperature, Aug. 1998, Journal of Chemical and Engineering Data, vol. 43 pp. 719-721.
Leaversuch, R. Materials: Renewable PLA Polymer Gets 'Green Light' for Packaging Uses, Mar. 2002, Plastics Technology Online at: http://www.ptonline.com/articles/200203fa2.html , pp. 1-4.
Nonfinal office action from corresponding U.S. Appl. No. 10/894,408, dated Nov. 2, 2007.
Final office action from corresponding U.S. Appl. No. 10/894,408, dated Aug. 1, 2008.
Final office action from corresponding U.S. Appl. No. 10/894,408, dated May 4, 2009.
Nonfinal office action from corresponding U.S. Appl. No. 10/894,408, dated Aug. 16, 2010.
Nonfinal office action from corresponding U.S. Appl. No. 10/894,429, dated Apr. 10, 2007.
Final office action from corresponding U.S. Appl. No. 10/894,429, dated Jan. 22, 2008.
Nonfinal office action from corresponding U.S. Appl. No. 10/894,429, dated Oct. 29, 2008.
Final office action from corresponding U.S. Appl. No. 10/894,429, dated Aug. 6, 2009.
Nonfinal office action from corresponding U.S. Appl. No. 10/894,432, dated May 22, 2008.
Final office action from corresponding U.S. Appl. No. 10/894,432, dated Mar. 5, 2009.
Nonfinal office action from corresponding U.S. Appl. No. 10/894,432, dated May 11, 2010.
Nonfinal office action from corresponding U.S. Appl. No. 10/894,430, dated Feb. 27, 2008.
Final office action from corresponding U.S. Appl. No. 10/894,430, dated Aug. 18, 2009.
Nonfinal office action from corresponding U.S. Appl. No. 10/894,410, dated Sep. 10, 2008.
Final office action from corresponding U.S. Appl. No. 10/894,410, dated Jun. 3, 2009.
Nonfinal office action from corresponding U.S. Appl. No. 11/033,780, dated Apr. 16, 2008.
Final office action from corresponding U.S. Appl. No. 11/033,780, dated Jun. 5, 2009.
Abstract from 123rd Annual Meeting of the Pharmaceutical Society of Japan, p. 97 (Mar. 2003).
Annunziata et al., Effect of polyethylene glycol on the liquid-liquid phase transition in aqueous protein solutions, *Proceedings of the National Academy of Sciences*, 99:14165-70 (2002).
Ataka, The initial process of protein crystal growth, *Japanese Assoc. for Crystal Growth*, 30:13-20 (2003).
Office Action from corresponding Japanese Application No. 2006-520406, dated Oct. 12, 2010.
Nonfinal office action, U.S. Appl. No. 10/894,430, dated Dec. 9, 2010.
Final office action, U.S. Appl. No. 10/894,432, dated Jan. 20, 2011.
Final office action, U.S. Appl. No. 10/894,408, dated Apr. 20, 2011.
Nonfinal office action, U.S. Appl. No. 10/894,429, dated Jul. 15, 2011.
Nonfinal office action, U.S. Appl. No. 10/894,410, dated Jul. 18, 2011.
Ceglia et al., "Meta-analysis: efficacy and safety of inhaled insulin therapy in adults with diabetes mellitus", Ann Intern Med., 145:665-675 (2006).
Online protocol on ammonium sulphate protein precipitation (http://research.biology.arizona.edu/mosquito/willott/proj/labpro/Prot/Proppt/Ammon.html).
Methoden der organischen Chemie, Ed. Eugen Müller, Georg Thieme Verlag-Stuttgart (1970), p. 381.
Gorin G et al., Section C, Physical Sciences—Isolation of Crystalline Urease, (1959) Proc. of the Okla. Acad. of Sci. For, pp. 62-70.
Third Party Observations Pursuant to Article 115 EPC filed in connection with European Patent Application No. 04809503.8, dated Jul. 23, 2012.

* cited by examiner

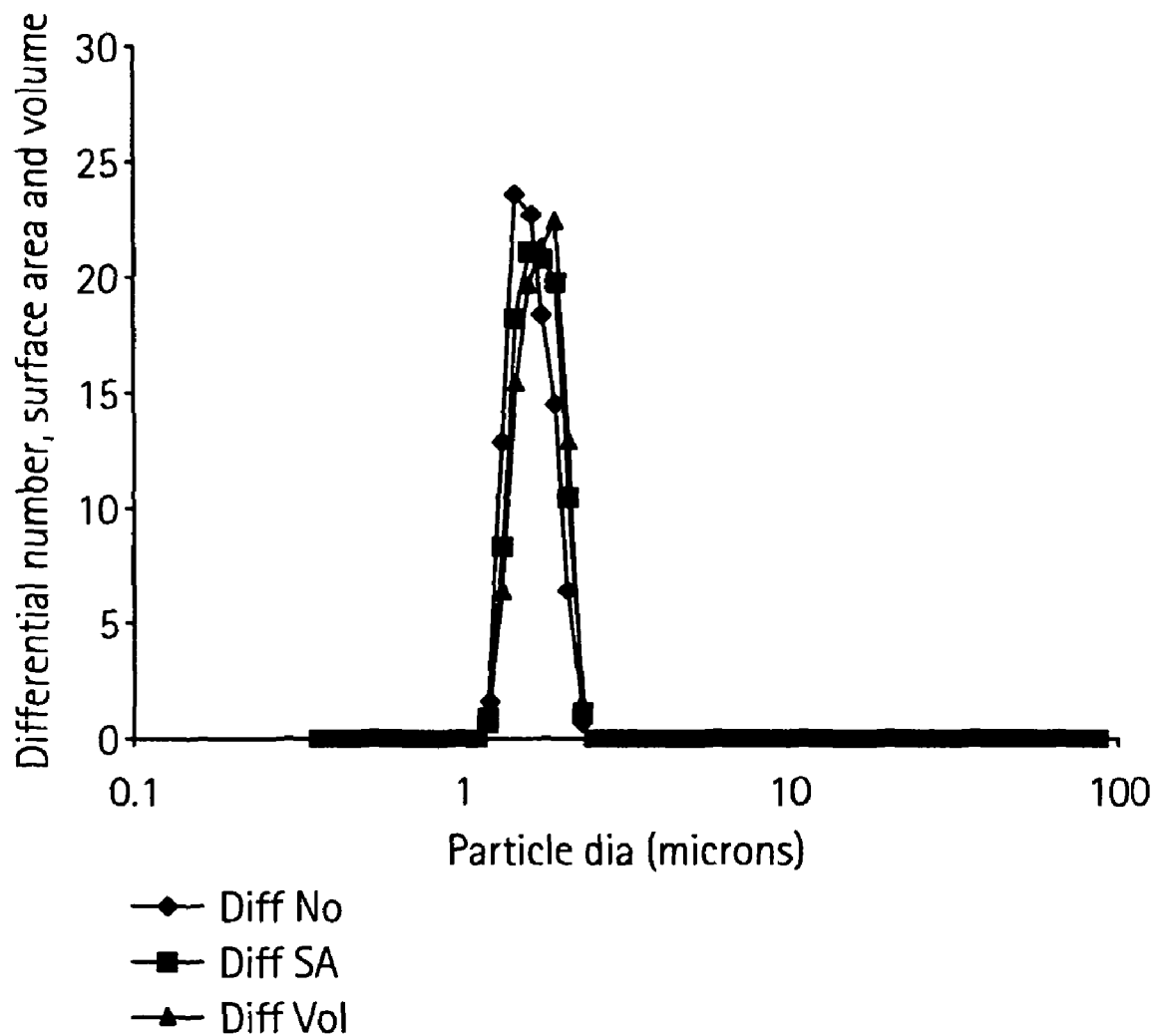

Insulin Stability in HFA-134a

MDI, CYCLOHALER and DISPhaler

YQ010302 Stability des-A21 25C

YQ010302 des-A21 37C

YQ010302 Stability 25C
Dimer + Oligomers

Lot YQ010302 HMW Stability 37C
Dimer + Oligomers

YQ010302 Total Rel. Compds. 25C

Rate of Reduction of Nitro Blue Tetrazolium- Rate Decreased by Addition of SOD (inhibitor)
Blank vs. SOD Controls VS. SOD Microspheres

PROTEIN MICROSPHERES HAVING INJECTABLE PROPERTIES AT HIGH CONCENTRATIONS

CROSS-REFERENCE TO RELATED APPLICATION

This is a continuation-in-part of application Ser. No. 10/894,410, filed Jul. 19, 2004 now abandoned, and claims priority to U.S. Provisional Application Ser. No. 60/570,274 filed May 12, 2004, each of which is incorporated herein in its entirety by reference and made a part hereof.

TECHNICAL FIELD

The present invention relates to compositions of small particles, preferably substantially spherical in shape, of an active agent. The active agents are preferably high molecular weight proteins, and more preferably substantially amorphous forms of high molecular weight proteins, and most preferably substantially amorphous monoclonal antibodies. The invention has the capability of providing injectable or syringable compositions of high molecular weight proteins, including monoclonal antibodies, at high concentrations, and accordingly provides the ability to deliver a clinically effective dose of such active agents with a low volume of composition, preferably with 10 ml or less of composition, and more preferably with a volume typically found in injection syringe applications including syringable low volume injections typical with subcutaneous bolus injections. Methods of production and methods of use of these compositions of small spherical particles of an active agent are also contemplated by this invention. In accordance with the method of production, the active agent is dissolved in an aqueous or aqueous-miscible solvent containing a dissolved phase-separation enhancing agent (PSEA) to form a solution in a single liquid phase. The solution then is subjected to a liquid-solid phase separation having the active agent comprising the solid phase and the PSEA and solvent comprising the liquid phase. The liquid-solid phase separation can be induced in numerous ways, such as changing the temperature of the solution or energy addition. The method is most suitable for forming small spherical particles of therapeutic agents which can be delivered to a subject in need of the therapeutic agent. The method is also most suitable for forming solid, small spherical particles of macromolecules, particularly macromolecules which are heat labile, such as proteins, including monoclonal antibody materials. The invention has the capability of providing syringable macromolecules.

BACKGROUND OF THE INVENTION

Field of the Invention

Several techniques have been used in the past for the manufacture of biopolymer nano- and microparticles. Conventional techniques include spray drying and milling for particle formation and can be used to produce particles of 5 microns or less in size.

U.S. Pat. No. 5,654,010 and U.S. Pat. No. 5,667,808 describe the production of a solid form of recombinant human growth hormone, hGH, through complexation with zinc in order to create an amorphous complex, which is then micronized through an ultrasound nozzle and sprayed down in liquid nitrogen in order to freeze the droplets. The liquid nitrogen is then allowed to evaporate at a temperature of −80° C. and the resultant material is freeze-dried.

Microparticles and microspheres are solid or semi-solid particles having a diameter of less than one millimeter, more preferably less than 100 microns and most preferably less than 10 microns, which can be formed of a variety of materials, including proteins, synthetic polymers, polysaccharides and combinations thereof. Microspheres have been used in many different applications, primarily separations, diagnostics, and drug delivery.

The most well known examples of microspheres used in separations techniques are those which are formed of polymers of either synthetic or natural origin, such as polyacrylamide, hydroxyapatite or agarose. In the controlled drug delivery area, molecules are often incorporated into or encapsulated within small spherical particles or incorporated into a monolithic matrix for subsequent release. A number of different techniques are routinely used to make these microspheres from synthetic polymers, natural polymers, proteins and polysaccharides, including phase separation, solvent evaporation, coascervation, emulsification, and spray drying. Generally the polymers form the supporting structure of these microspheres, and the drug of interest is incorporated into the polymer structure.

Particles prepared using lipids to encapsulate target drugs are currently available. Liposomes are spherical particles composed of a single or multiple phospholipid and/or cholesterol bilayers. Liposomes are 100 nanometer or greater in size and may carry a variety of water-soluble or lipid-soluble drugs. For example, lipids arranged in bilayer membranes surrounding multiple aqueous compartments to form particles may be used to encapsulate water soluble drugs for subsequent delivery as described in U.S. Pat. No. 5,422,120 to Sinil Kim.

Spherical beads have been commercially available as a tool for biochemists for many years. For example, antibodies conjugated to beads create relatively large particles that have binding specificity for particular ligands. Antibodies are routinely used to bind to receptors on the surface of a cell for cellular activation, are bound to a solid phase to form antibody-coated particles for immunoaffinity purification, and may be used to deliver a therapeutic agent that is slowly released over time, using tissue or tumor-specific antibodies conjugated to the particles to target the agent to the desired site.

There is an on-going need for development of new methods for making particles, particularly those that can be adapted for use in the drug delivery, separation and diagnostic areas. The most desirable particles from a utility standpoint would be small spherical particles that have the following characteristics: narrow size distribution, substantially spherical, substantially consisting of only the active agent, retention of the biochemical integrity and of the biological activity of the active agent. The particles should provide a suitable solid that would allow additional stabilization of the particles by coating or by microencapsulation. Further, the method of fabrication of the small spherical particles would have the following desirable characteristics: simple fabrication, an essentially aqueous process, high yield, and requiring no subsequent sieving.

A high molecular weight protein is a sequence of amino acids for which the chain length is sufficient to produce the higher levels of tertiary and/or quaternary structure. This is to distinguish from 'peptides' or other small molecular weight drugs that do not have such structure.

An antibody (immunoglobulin) is a protein produced by immune system cells (B lymphocytes) in response to a foreign molecule (antigen) or invading organism. An antibody often binds to the foreign molecule or cell extremely tightly, thereby inactivating it or marking it for destruction by phagocytosis or complement-induced lysis.

Immunoglobulin (Ig) is an antibody molecule. Higher vertebrates have five classes of immunoglobulins—IgA, IgD, IgE, IgG, and IgM—each with different role in the immune response.

A monoclonal antibody (mAb) is a highly specific, purified antibody (immunoglobulin molecule) that is derived from only one clone of immune system cells (B lymphocytes) and recognizes a specific site of only one foreign molecule (antigen). Monoclonal antibodies can be mass produced by laboratory manipulations (murine, chimeric, humanized). The term "monoclonal antibody" is used in a broader sense and specifically covers monoclonal antibodies which have an immunoglobulin Fc region, antibody compositions with polyepitopic specificity, bispecific antibodies, diabodies, and single-chain molecules, as well as antibody fragments (e.g., Fab, F(ab')$_2$, and Fv).

Polyclonal antibodies are a range of antibodies (immunoglobulin molecules) that are specific for many sites of a single foreign molecule (antigen). Natural immune responses are polyclonal.

Antibodies referred to as trap molecules are composed of fusions between two distinct receptor components and a portion of an antibody molecule called the "Fc region", resulting in the generation of growth factor and cytokine blockers with markedly increased affinity over that offered by single component reagents. Trap molecules, for example, have been developed by Regeneron Pharmaceuticals.

Monoclonal antibodies (mAbs) can be a laboratory-derived population of antibodies derived from one clone of cells and are highly specific in binding one particular antigen site. They are large proteins, in the order of 150 kDa, comprised of four polypeptide chains: two light chains of about 25 k Da each and two heavy chains of about 50 k Da each. Due to their size, monoclonal antibodies generally are currently delivered by intravenous injection.

Antibodies often need to be delivered at relatively large quantities in order to achieve therapeutic effect. For instance, the delivery dose for many antibodies is between about 100 to 800 mg. Injectability of these large quantities of material present substantial formulation and delivery challenges. A small volume of such large dosage will typically have high viscosity; therefore, large volumes, on the order of 10-250 mL are needed to deliver it intravenously. Intravenous delivery is very uncomfortable to the patient, requires clinical settings, and it is both expensive and time consuming.

Microparticle technology according to the invention can offer significant advantages for this market, because it allows formation of highly concentrated suspensions that can be readily soluble upon injection. Similarly, other active agents comprising high molecular weight proteins can benefit from the present invention. The invention describes compositions that can be delivered at high concentrations and at relatively small volumes, thus compositions with syringability and injectability properties. Prior to the invention, monoclonal antibodies, other antibodies, or other high molecular weight proteins with a molecular weight above about 25 kDa, could not be injected using a fine gauge needle, such as a 20 gauge and finer needle used in connection with a standard syringe. Nor could such a protein be delivered prior to the invention, in a small volume (10 ml or less) containing a clinically effective dose of the protein. The use of microparticle technology in connection with these molecules solves the problem of high volume injection of these molecules as previously required. This invention also can be useful in assisting in delivering lower molecular weight protein materials at high concentrations within a small injection volume and during a short delivery time.

The manufacturing process for a monoclonal antibody is a tedious process, which explains its high price. Thus, it is important that mAbs are precisely delivered to a target location in a very efficient and safe manner. Also important in the preparation and delivery of microparticles, whether mAbs or not, is high yield formation of readily soluble microparticles or microspheres, the retention of their respective chemical integrities, and in the case of materials such as mAbs, very good injectability that may allow delivery by the subcutaneous, ocular, or other administration routes.

An aspect or object of the invention is to provide a substantially amorphous or non-crystalline antibody microparticle.

Another aspect or object of the present invention is to provide a syringable composition including substantially amorphous or non-crystalline antibody microparticles.

A further aspect or object of this invention is to provide a syringable composition providing a clinically effective dose of protein in about 10 ml or less of the composition, even when the protein has a molecular weight of about 25,000 Daltons and above.

A further aspect or object of the present invention is to provide microparticles having at least about 50 mg of active agent per ml of a clinically effective dose, finding especially advantageous application when the active agent has a molecular weight of at least about 25,000 Daltons.

Another aspect or object of the invention is to provide a method of using microparticles in clinically effective manners through active agent delivery by injection at high concentrations such as but not limited to subcutaneous injection.

A further aspect or object of the present invention is a process for preparing microparticles of protein materials of relatively high molecular weight.

Another object or aspect of the present invention is to provide microparticles, preferably microspheres, which are readily soluble, i.e. exhibit solubility within about ten minutes in a PBS buffer at physiological pH, while exhibiting chemical integrity, i.e. at least about 90 percent of the compound is chemically intact in the microparticles, and which exhibit injectability, more particularly in the form of syringability, i.e. form at least a 50 mg/ml suspension and deliverability of the suspension through a fine gauge (small bore) needle without use of excessive force.

Other aspects, objects and advantages of the present invention will be understood from the following description according to the preferred embodiments of the present invention, specifically including stated and unstated combinations of the various features which are described herein, relevant information concerning which is shown in the accompanying drawing.

SUMMARY OF THE INVENTION

The present invention relates to protein microparticles having injectable properties at high doses. The protein is an active agent, and the microparticles are substantially amorphous or non-crystalline. With these compositions, very high concentrations of active agent are deliverable in very low volumes.

The active agent of the present invention is preferably an active agent, which can be a therapeutic agent or a diagnostic agent. In a preferred embodiment of the present invention, the active agent is a macromolecule protein, including a monoclonal antibody. In yet another preferred embodiment, the particles containing the active agent are suitable for in vivo delivery to a subject in need of the agent by any suitable route, including subcutaneous and/or ocular injection approaches, which are otherwise not feasible for high concentrations of macromolecules of these types.

The present invention also relates to methods of production and methods of use of microparticles, small spherical particles or microspheres of an active agent. In accordance with a method of production, the active agent is dissolved in a solvent containing a dissolved phase-separation enhancing agent to form a solution that is a single liquid phase. The solvent is preferably an aqueous or aqueous miscible solvent. The solution is then subjected to a liquid-solid phase separation having the active agent comprising the solid phase and the PSEA and solvent comprising the liquid phase. The liquid-solid phase separation can be induced in numerous ways, such as changing the temperature of the solution to below the phase transition temperature of the solution.

In a preferred embodiment of the present invention, the method of subjecting the solution to a liquid-solid phase separation is by cooling the solution to below the phase transition temperature of the active agent in the solution. That temperature may be above or below the freezing point of the solution. For solutions in which the freezing point is above the phase transition temperature, the solution can include a freezing point depressing agent, such as polyethylene glycol or propylene glycol, to lower the freezing point of the solution to allow the phase separation in the solution to occur without freezing the solution.

The phase-separation enhancing agent of the present invention enhances or induces the liquid-solid phase separation of the active agent in the solution when the solution is subjected to the step of phase change in which the active agent solidifies to form a suspension of small spherical particles as a discontinuous phase while the phase-separation enhancing agent remains dissolved in the continuous phase. That is, the phase separating enhancing agent does not go through a change of phase, but the active agent does go through a phase change.

The method of producing the particles in the present invention may also include an additional step of controlling the liquid-solid phase separation of the particles to control the size and shape of the particles formed. Methods of controlling the phase-separation include control of the ionic strength, the pH, the concentration of the phase-separation enhancing agent, the concentration of the active agent in the solution, or controlling the rate of change in temperature of the solution, the control of these being either before the phase-separation or a change of any or several of these in order to induce the phase-separation.

In a preferred embodiment of the present invention, the small spherical particles are separated from the PSEA in the continuous phase after particle formation. In yet another preferred embodiment, the method of separation is by washing the solution containing the particles with a liquid medium in which the active agent is not soluble in the liquid medium while the phase-separation enhancing agent is soluble in the liquid medium. The liquid washing medium may contain an agent which reduces the solubility of the active agent in the liquid medium. The liquid washing medium may also contain one or more excipients. The excipient may act as a stabilizer for the small spherical particles or for the active agent or the carrier agent. The excipient may also imbue the active agent or the particle with additional characteristics such as controlled release of the active agent from the particles or modified permeation of the active agent through biological tissues. In another preferred embodiment, while the small particles do not include the PSEA, they may be harvested in the presence of the PSEA phase for subsequent processing steps prior to separation from the PSEA phase. In another preferred embodiment, the solution is an aqueous solution comprising an aqueous or aqueous-miscible solvent.

BRIEF DESCRIPTION OF THE DRAWINGS

FIG. 6 reports particle size distribution by number, surface area and volume distribution of anti-Factor VIII monoclonal antibody microspheres as described in Example 5.

FIG. 29 is a chart showing insulin stability data in HFA-134a.

FIG. 42A is a schematic illustration of the continuous emulsification reactor when surface active compound added to the continuous phase or the dispersed phase before emulsification, and FIG. 42B is a schematic illustration of the continuous emulsification reactor when the surface active compound is added after emulsification.

DESCRIPTION OF THE PREFERRED EMBODIMENTS

Figure 1A:
FIGS. 1a and 1b give optical microscope images of anti-Factor VIII monoclonal antibody microspheres prepared as described in Example 3.
Figure 1B:
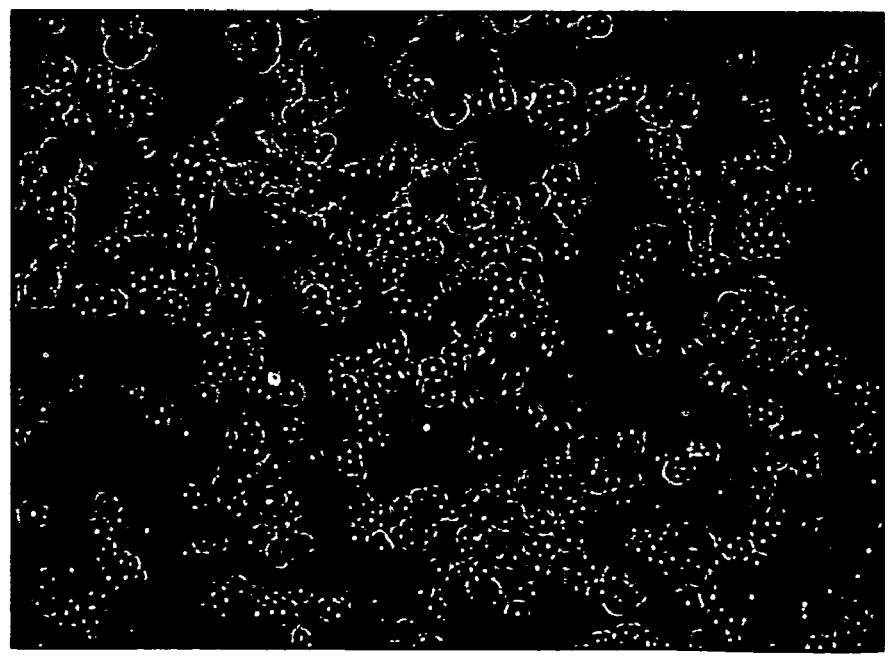

The present invention is susceptible to embodiments in many different forms. Preferred embodiments of the invention are disclosed with the understanding that the present disclosure is to be considered as exemplifications of the principles of the invention and are not intended to limit the broad aspects of the invention to the embodiments illustrated.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The present invention is related to compositions of substantially amorphous or non-crystalline small particles of an active agent that is a protein. Special application is found when the active agent has a molecular weight of at least about 25,000 Daltons. In accordance with the method of production, the active agent is dissolved in a solvent containing a dissolved phase-separation enhancing agent to form a solution that is a single liquid continuous phase. The solvent is preferably an aqueous or aqueous-miscible solvent. The solution is then subjected to a phase change, for example, by lowering the temperature of the solution to below the phase transition temperature of the active agent, whereby the active agent goes through a liquid-solid phase separation to form a suspension of substantially amorphous or non-crystalline small particles constituting a discontinuous phase while the phase-separation enhancing agent remains in the continuous phase.

The present invention relates to compositions of small particles, preferably substantially spherical in shape, of an active agent. The active agents are preferably high molecular weight proteins, and more preferably substantially amorphous forms of high molecular weight proteins, and most preferably substantially amorphous monoclonal antibodies.

The invention has the capability of providing injectable or syringable compositions of high molecular weight proteins, including monoclonal antibodies, at high concentrations, and accordingly provides the ability to deliver a clinically effective dose of such active agents with a low volume of composition, preferably with 10 ml or less of composition, and more preferably with a volume typically found in a standard syringe.

Methods of production and methods of use of these compositions of small spherical particles of an active agent are also contemplated by this invention. In accordance with the method of production, the active agent is dissolved in an aqueous or aqueous-miscible solvent containing a dissolved phase-separation enhancing agent (PSEA) to form a solution in a single liquid phase. The solution then is subjected to a liquid-solid phase separation having the active agent comprising the solid phase and the PSEA and solvent comprising the liquid phase. The liquid-solid phase separation can be induced in numerous ways, such as changing the temperature of the solution or energy addition. The method is most suitable for forming small spherical particles of therapeutic agents which can be delivered to a subject in need of the therapeutic agent. The method is also most suitable for forming solid, small spherical particles of macromolecules, particularly macromolecules which are heat labile, such as proteins, including monoclonal antibody materials. The invention has the capability of providing syringable macromolecules.

The Active Agent

The active agent of the present invention is a protein which can be a therapeutic agent or a diagnostic agent. Preferred active agents are high molecular weight proteins. Preferred agents are amorphous forms of proteins, including amorphous antibodies.

When used herein, the term antibody encompasses monoclonal antibodies, polyclonal antibodies, and antibody fragments, especially the antigen-binding fractions generally known as "Fab" fragments or regions, single chain antibodies, as well as monoclonal or polyclonal antibodies or other antibodies in recombinant form, and are what are currently recognized in the art by the designation "trap molecule". Antibodies also refers to any of the aforementioned forms of antibodies that are treated, such as by coating or encapsulating, including by approaches as described herein.

Trap molecules are composed of fusions between two distinct receptor components and a portion of an antibody molecule referred to as the "Fc region" resulting in the generation of growth factor and cytokine blockers with markedly increased affinity over that offered by single-component reagents.

The following references provide further information on trap molecules: "Cytokine Traps: Multi-Component, High-Affinity Blockers of Cytokine Action"; Economides A N, Carpenter L R, Rudge J S, Wong V, Koehler-Stec E M, Hartnett C, Pyles E A, Xu X, Daly T J, Young M R, Fandl J P, Lee F, Carver S, McNay J, Bailey K, Ramakanth S, Hutabarat R, Huang T T, Radziejewski C, Yancopoulos G D, Stahl N; Journal: Nat Med (2003); Volume, (Number), Pages: 9(1):47-52. "Vascular Eendothelial Growth Factor-Trap Decreases Tumor Burden, Inhibits Ascites, and Causes Dramatic Vascular Remodeling in an Ovarian Cancer Model"; Byrne A T, Ross L, Holash J, Nakanishi M, Hu L, Hofmann J I, Yancopoulos G D, Jaffe R B; Journal: Clin Cancer Res (2003); Volume, (Number), Pages: 15; 9(15):5721-8. "Prevention of Thecal Angiogenesis, Antral Follicular Growth, and Ovulation in the Primate by Treatment with Vascular Endothelial Growth Factor Trap R1R2"; Wulff C, Wilson H, Wiegand S J, Rudge J S, Fraser H M; Journal: Endocrinology (2002); Volume, (Number), Pages: 143(7):2797-807. Volume, (Number), Pages: 143(7):2797-807.

In a preferred embodiment of the present invention, the active agent is a monoclonal antibody, which can be natural or synthetic. Examples of monoclonal antibodies include, but are not limited to: adalimutab (available from Abbot under the tradename HUMIRA®), abciximab (available from Centocor under the tradename REoPRO®); daclizumab, (available from Roche under the tradename Zenapaz™), rituximab (available from IDEC/Genentech under the tradename RITUXIN® or RITUXAN®), basiliximab (available from Novartis under the tradename SIMULECT®), palivzumab (available from Medimmune under the tradename SYNAGIS®), infliximab (available from Centocor under the tradename REMICADE®), trastuxumab (available from Genentech under the tradename HERCEPTIN®), gemtuzumab (available from IDEC under the tradename MYLOTARG®), alemzutumab (available from Millennium/ILEX under the tradename Campath®), and ibritumomab (available from IDEC under the tradename ZEVULIN™). Gammagard Liquid (available from Baxter Healthcare Corporation, Westlake Village, Calif.) is a ready-for-use sterile, liquid preparation of highly purified and concentrated immunoglobulin G (IgG) antibodies.

Examples of antibody "Fab" fractions or regions include, but are not limited to, the following: TGX-6B4, currently in development by ThromboGenics Ltd of Dublin, Ireland, is an antibody to GP1b which inhibits platelet adhesion and is indicated to be a novel approach to prevent early steps in arterial thrombosis; Digoxin specific Fab fragments have been reported to be beneficial in the treatment of toad venom poisoning. (Heart. 2003; 89: 12-472, Toxalert, 15: issue 1, 1998); Humanized Fab fragments have been shown to recognize the IgE-binding domain of human Fc(epsilon)RIalpha in COS and CHO cells (Journal of Biochemistry, 2001: Vol 129, Issue 1 5-12). Other information concerning Anti-tumor Radioimmunotherapy using multivalent Fab' fragments is found in British Journal of Cancer (1999) 81, 972-980.

Examples of other high molecular weight proteins include but are not limited to AAT, Dnase, superoxide dismutase, subtilisin and other proteins. Typically, high molecular weight indicates a protein having molecular weights on the order of approximately 25,000, depending on particular needs or properties of the protein or to its intended use. Lower molecular weight proteins can benefit from the invention to the extent same needs to be administered, for example by injection, in high concentrations. Such proteins are known in the art; see for example U.S. patent application Ser. No. 10/894,410 filed Jul. 19, 2004 and Ser. No. 10/896,326 filed Jul. 21, 2004.

The Microparticles Small Spherical Particles or Microspheres

The microparticles or the microspheres of the present invention preferably have an average geometric particle size of less than 200 microns, typically from about 0.01 μm to about 200 μm, typically not more than about 50 μm, more preferably from 0.1 μm to 10 μm, even more preferably from about 0.5 μm to about 5 μm, and most preferably from about 0.5 μm to about 3 μm, as measured by dynamic light scattering methods (e.g., photocorrelation spectroscopy, laser diffraction, low-angle laser light scattering (LALLS), medium-angle laser light scattering (MALLS)), by light obscuration methods (Coulter analysis method, for example) or by other methods, such as rheology or microscopy (light or electron).

The small spherical particles or microspheres are substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles may have surface texturing, such as lines or indentations or protuberances that are small in scale when compared to the overall size of the particle and still be substantially spherical. More preferably, the ratio of lengths between the longest and shortest axes of the particle is less than or equal to about 1.33. Most preferably, the ratio of lengths between the longest and shortest axes of the particle is less than or equal to about 1.25. Surface contact is minimized in microspheres that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

The microparticles also preferably have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The spherical microparticles of the invention preferably are within a narrow size distribution, thereby minimizing opportunities for contact agglomeration. What is meant by a "narrow size distribution" is a preferred particle size distribution that has a ratio of the volume diameter of the $90^{th}$ percentile of the small spherical particles to the volume diameter of the $10^{th}$ percentile less than or equal to 5. More preferably, the volume diameter of the $90^{th}$ percentile of the small spherical particles to the volume diameter of the $11^{th}$ percentile is less than or equal to 3. Most preferably, the ratio of the volume diameter of the $90^{th}$ percentile of the small spherical particles to the volume diameter of the $10^{th}$ percentile is less than or equal to 2.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less then 15.9%. The GSD has a narrow size distribution when GSD<2.5, more preferably less than 1.8.

In a preferred form of the invention, the active agent in the microparticle or microsphere is semi-crystalline or non-crystalline or substantially amorphous.

The microspheres are preferably comprised of active agents which are substantially amorphous or non-crystalline, that is they are in an amorphous or semi-crystalline form. As used herein, "amorphous" refers to a generally random solid form of the active agent wherein crystalline lattices of the protein(s) or other active agent(s) within the microsphere are absent, and "semi-crystalline" refers to a generally random solid form of active agent(s) wherein the active agent content of the microsphere is comprised of less than 50% of crystalline lattice forms of the active agent(s).

Typically, the microparticles or microspheres are substantially non-porous and have a density greater than 0.5 g/cm$^3$, more preferably greater than 0.75 g/cm$^3$ and most preferably greater than about 0.85 g/cm$^3$. A preferred range for the density is from about 0.5 to about 2 g/cm$^3$ and more preferably from about 0.75 to about 1.75 g/cm$^3$ and even more preferably from about 0.85 g/cm$^3$ to about 1.5 g/cm$^3$. The substantially amorphous or non-crystalline microparticles according to the invention are more readily soluble or exhibit a rate of dissolution faster than microparticles which are not so constituted, such as crystalline microparticles.

The microparticles or microspheres of the present invention can exhibit a high content of the active agent. There is no requirement for a significant quantity of bulking agents or similar excipients that are required by many other methods of preparing microparticles, although materials in addition to the active-agent can be included as desired to achieve a particular objective or objectives. For example, in many applications, the active agent of the microspheres comprise equal to or greater than 95% by weight of the particles. Typically, the active agent is present from about 20% to 100% by weight of the particle, preferably from about 50% to about 100% by weight, more preferably from about 80% to about 100% by weight, even more preferably from about 90% to about 100% by weight. When stating ranges herein, it is meant to include any range or combination of ranges therein.

A further aspect of the present invention is that the microparticles or microspheres retain the biochemical integrity and the biological activity of the active agent with or without the inclusion of excipients.

In vivo Delivery of the Particles

Microparticles, small spherical particles or microspheres containing the active agent in the present invention are suitable for in vivo delivery to a subject in need of the agent by an injectable route. A preferred delivery route is injectable, which includes intravenous, intramuscular, subcutaneous, intraperitoneal, intrathecal, epidural, intra-arterial, intra-articular and the like. Other delivery routes, such as topical, oral, rectal, nasal, pulmonary, vaginal, buccal, sublingual, transdermal, transmucosal, otic or intraocular, could be practiced, but typically the advantages of the invention are more evident for injection applications. Most preferred for the purpose of this invention is the syringable delivery route. Most importantly, the microparticles or microspheres can be aspirated into a syringe and injected through fine needles despite the high molecular weight of the proteins or active agents. A preferred delivery route is injection with a fine needle, which includes subcutaneous, ocular and the like. By fine needle is meant needles of at least 20 Gauge size, typically between about 22 Gauge and about 30 Gauge and above. Advantageously, the fine needles can be at least as fine as 24 Gauge, more advantageously at least as fine as 26 gauge, and even more advantageously at least as fine as 28 Gauge.

The microparticles or microspheres are capable of being injected at a concentration of at least about 50 mg of protein per ml of the composition being injected. For example, from about 100 to about 800 mg of protein are injectable in a delivery volume if not more than about 10 ml, and usually at least about 2 ml for many applications. Also, the delivery is made during normal injection time periods. Typically such time periods are not more than about 20 seconds or less.

The present method for particle formation set forth herein provides for particle formation with or without excipients or other components or additives as desired or required. Fabrication of protein microparticles or microspheres from protein itself with no additives is also an approach according to the invention and at time provides superior advantages for use.

Methods for Making Microparticles

The Continuous Phase

The method of the present invention of preparing microparticles or microspheres of an active agent begins with providing a solution having the active agent and a phase-separation enhancing agent dissolved in a first solvent in a single liquid phase. The solution can be an organic system comprising an organic solvent or a mixture of miscible organic solvents. The solution can also be an aqueous-based solution comprising an aqueous medium or an aqueous-miscible organic solvent or a mixture of aqueous-miscible organic solvents or combinations thereof. The aqueous medium can be water, normal saline, buffered solutions, buffered saline, and the like. Suitable aqueous-miscible organic solvents include, but are not limited to, N-methyl-2-pyrrolidinone(N-methyl-2-pyrrolidone), 2-pyrrolidinone(2-pyrrolidone), 1,3-dimethyl-2-imidazolidinone (DMI), dimethylsulfoxide, dimethylacetamide, acetic acid, lactic acid, acetone, methyl ethyl ketone, acetonitrile, methanol, ethanol, isopropanol, 3-pentanol, n-propanol, benzyl alcohol, glycerol, tetrahydrofuran (THF), polyethylene glycol (PEG), PEG-4, PEG-8, PEG-9, PEG-12, PEG-14, PEG-16, PEG-120, PEG-75, PEG-150, polyethylene glycol esters, PEG-4 dilaurate, PEG-20 dilaurate, PEG-6 isostearate, PEG-8 palmitostearate, PEG-150 palmitostearate, polyethylene glycol sorbitans, PEG-20 sorbitan isostearate, polyethylene glycol monoalkyl ethers, PEG-3 dimethyl ether, PEG-4 dimethyl ether, polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether), alkanes including propane, butane, pentane, hexane, heptane, octane, nonane, decane, or a combination thereof.

The single continuous phase can be prepared by first providing a solution of the phase-separation enhancing agent, which is either soluble in or miscible with the first solvent. This is followed by adding the active agent to the solution. The active agent may be added directly to the solution, or the active agent may first be dissolved in a second solvent and then together added to the solution. The second solvent can be the same solvent as the first solvent, or it can be another solvent selected from the list above and which is miscible with the solution. It is preferred that the active agent is added to the solution at an ambient temperature or lower, which is important particularly for heat labile molecules, such as certain proteins. What is meant by "ambient temperature" is a temperature of around room temperature of about 20° C. to about 40° C. However, the system can also be heated to increase the solubility of the active agent in the system as long as heating does not cause significant reduction in the activity of the agent.

The Phase-Separation Enhancing Agent

The phase-separation enhancing agent (PSEA) of the present invention enhances or induces the liquid-solid phase separation of the active agent from the solution when the solution is subjected to the step of phase separation in which the active agent becomes solid or semi-solid to form a suspension of small spherical particles as a discontinuous phase while the phase-separation enhancing agent remains dissolved in the continuous phase. The phase-separation enhancing agent reduces the solubility of the active agent when the solution is brought to the phase separation conditions. Suitable phase-separation enhancing agents include, but are not limited to, polymers or mixtures of polymers that are soluble or miscible with the solution. Examples of suitable polymers include linear or branched polymers, copolymers and block copolymers. These polymers can be water soluble, semi-water soluble, water-miscible, or insoluble.

In a preferred form of the invention, the phase-separation enhancing agent is water soluble or water miscible. Types of polymers that may be used include carbohydrate-based polymers, polyaliphatic alcohols, poly(vinyl) polymers, polyacrylic acids, polyorganic acids, polyamino acids, co-polymers and block co-polymers (e.g., poloxamers such as Pluronic F127 or F68), tert-polymers, polyethers, naturally occuring polymers, polyimides, surfactants, polyesters, branched and cyclo-polymers, and polyaldehydes.

Preferred polymers are ones that are acceptable as pharmaceutical additives for the intended route of administration of the active agent particles. Preferred polymers are pharmaceutically acceptable additives such as polyethylene glycol (PEG) of various molecular weights, such as PEG 200, PEG 300, PEG 3350, PEG 8000, PEG 10000, PEG 20000, etc. and poloxamers of various molecular weights such as poloxamer 188 and Pluronic F127 or Pluronic F68. Yet another preferred polymer is polyvinylpyrrolidone (PVP). Yet another preferred polymer is hydroxyethylstarch. Other amphiphilic polymers can also be used alone or in combinations. The phase-separation enhancing agent can also be a non-polymer such as a mixture of propylene glycol and ethanol.

Liquid-Solid Phase Separation

A liquid-solid phase separation of the active agent in the solution can be induced by any method known in the art, such as change in temperature (either raising or lowering), change in pressure, change in pH, change in ionic strength of the solution, change in the concentration of the active agent, change in the concentration of the phase-separation enhancing agent, change in osmolality of the solution, combinations of these, and the like.

In a preferred embodiment of the present invention, the phase change is a temperature-induced phase change. In many embodiments the temperature-induced phase change is effected by lowering the temperature below the phase transition temperature of the active agent in the solution.

Figure 13:
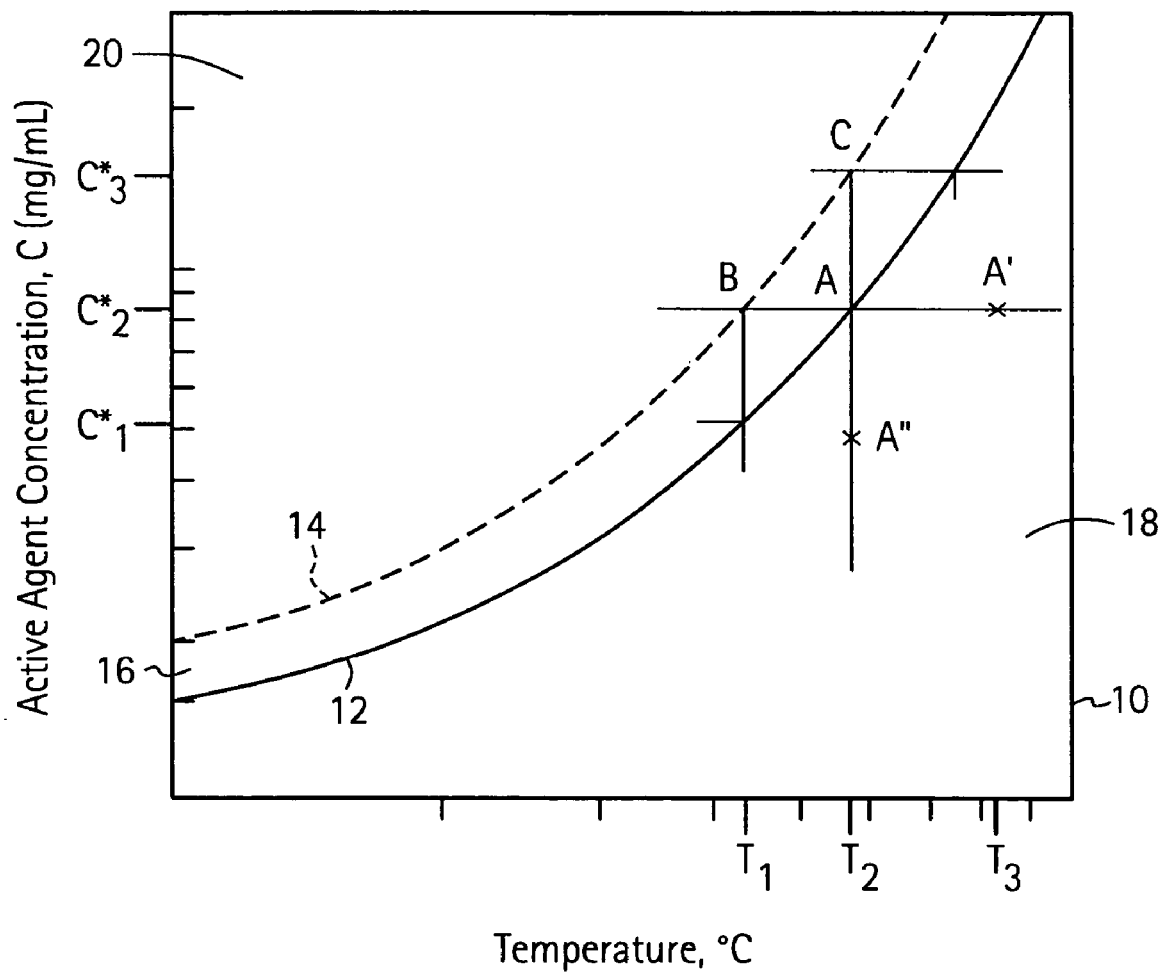
FIG. 13 is a two-dimensional phase diagram plotting active agent concentration against temperature.

FIG. 13 is a two-dimensional phase diagram 10 for the solution containing solvent, a PSEA and an active agent. The diagram plots the active agent concentration against the temperature of the solution. The concentration of the PSEA is held constant.

The diagram of FIG. 13 has a saturation curve 12; a supersaturation curve 14; a metastable area 16 therebetween; a first area 18 below the saturation curve where the system is in a homogenous, single liquid phase where all components are in the liquid phase; and a second area 20 above the supersaturation curve where the system is a two-phase system having a solid phase of the active agent and a liquid phase of the PSEA and solvent. The phase diagram is helpful in determining the temperature of the system and the relative concentration of components in the pure liquid phase, the liquid-solid phase and the conditions surrounding the transition between these two phases.

As disclosed herein, preparation of microparticles or microspheres of the active agent principally involves cooling from an undersaturated solution (point A' in FIG. 13) reaching saturation at point A where the solution is in equilibrium with any solid phase that may be present. On further cooling, a state is reached where the solution contains more active agent than that corresponding to the equilibrium solubility at the given temperature; the solution thus becomes supersaturated. Spontaneous formation of the solid phase does not occur until point B is reached. Point B is a point on the boundary of the metastable zone. The metastable zone width can be expressed either by the maximum attainable undercooling $\Delta T_{max} = T_2 - T_1$ or by the supersaturation $\Delta C_{max} = C^*_2 - C^*_1$. These two expressions are thermodynamically equivalent:

$$\Delta C_{max} = C^*_2 - C^*_1 = \int_{T_1}^{T_2} \left(\frac{\partial C^*}{\partial T}\right) dT \cong \Delta T_{max}\left(\frac{dC^*}{dT}\right)$$

The path A'-A-B represents a polythermal method of preparing a metastable solution. In an isothermal process the starting point would be A''. By increasing the concentration at constant temperature, saturation will again be achieved at point A. An isothermal increase in concentration (by solvent evaporation or by seeding/addition of the active agent, for instance) to point C will cause the solution to move into the metastable region until the metastability limit is again reached. When the metastable limit is exceeded, the solution becomes unstable and a spontaneous formation of the solid phase immediately occurs.

The value $(\Delta C_{max})_T = C^*_3 - C^*_2$ obtained isothermally can be different from the corresponding value of $\Delta T_{max} = T_3 - T_2$ obtained polythermally. As the boundary of the metastable zone is approached, the time necessary for the solid particle formation decreases until the metastable limit is reached.

In the polythermal process, the rate of cooling is done at a controlled rate to control the size and shape of the particles. What is meant by a controlled rate is about 0.2° C./minute to about 50° C./minute, and more preferably from 0.2° C./minute to 30° C./minute. The rate of change can be at a constant or linear rate, a non-linear rate, intermittent, or a programmed rate (having multiple phase cycles). The particles can be separated from the PSEA in the solution and purified by washing as will be discussed below.

The present invention contemplates adjusting the concentration of the active agent, the concentration of the PSEA, the temperature or any combination of these to cause a phase change where the active agent goes from a liquid state to a solid state while the PSEA and solvent do not go through a phase change and remain as liquids. It is also contemplated changing the pH, the ionic strength, the osmolality and the like to enhance, promote, control or suppress the phase change. For solutions in which the freezing point is relatively high, or the freezing point is above the phase transition temperature, the solutions can include a freezing point depressing agent, such as propylene glycol, sucrose, ethylene glycol, alcohols (e.g., ethanol, methanol) or aqueous mixtures of freezing-point depression agents to lower the freezing point of the system to allow the phase change in the system without freezing the system. The process can also be carried out such that the temperature is reduced below the freezing point of the system. The process described herein is particularly suitable for molecules that are heat labile (e.g., proteins).

Optional Excipients

The microparticles of the present invention may include one or more excipients. The excipient may imbue the active agent or the microparticles with additional characteristics such as increased stability of the microparticles or of the active agents or of the carrier agents, controlled release of the active agent from the microparticles, or modified permeation of the active agent through biological tissues. Suitable excipients include, but are not limited to, carbohydrates (e.g., trehalose, sucrose, mannitol), cations (e.g., $Zn^{2+}$, $Mg^{2+}$, $Ca^{2+}$), anions (e.g. $SO_4^{2-}$), amino acids (e.g., glycine), lipids, phospholipids, fatty acids, surfactants, triglycerides, bile acids or their salts (e.g., cholate or its salts, such as sodium cholate; deoxycholic acid or its salts), fatty acid esters, and polymers present at levels below their functioning as PSEA's. When an excipient is used, the excipient does not significantly affect the phase diagram of the solution.

Separating and Washing the Particles

In a preferred embodiment of the present invention, the microparticles or microspheres are harvested by separating them from the phase-separation enhancing agent in the solution. In yet another preferred embodiment, the method of separation is by washing the solution containing the microparticles or microspheres with a liquid medium in which the active agent is not soluble in the liquid medium while the phase-separation enhancing agent is soluble in the liquid medium. Some methods of washing may be by diafiltration or by centrifugation. The liquid medium can be an aqueous medium or an organic solvent. For active agents with low aqueous solubility, the liquid medium can be an aqueous medium or an aqueous medium containing agent that reduces the aqueous solubility of the active agent, such as divalent cations. For active agents with high aqueous solubility, such as many proteins, an organic solvent or an aqueous solvent containing a protein-precipitating agent such as ammonium sulfate may be used.

Examples of suitable organic solvents for use as the liquid medium include those organic solvents specified above as suitable for the continuous phase, and more preferably methylene chloride, chloroform, acetonitrile, ethylacetate, methanol, ethanol, pentane, and the like. It is also contemplated to use mixtures of any of these solvents. One preferred blend is methylene chloride or a 1:1 mixture of methylene chloride and acetone. It is preferred that the liquid medium has a low boiling point for easy removal by, for example, lyophilization, evaporation, or drying.

The liquid medium also can be a supercritical fluid, such as liquid carbon dioxide or a fluid near its supercritical point. Supercritical fluids can be suitable solvents for the phase-separation enhancing agents, particularly some polymers, but are nonsolvents for protein particles. Supercritical fluids can be used by themselves or with a cosolvent. The following supercritical fluids can be used: liquid $CO_2$, ethane, or xenon. Potential cosolvents can be acetontitrile, dichloromethane, ethanol, methanol, water, or 2-propanol.

The liquid medium used to separate the microparticles or microspheres from the PSEA described herein, may contain an agent which reduces the solubility of the active agent in the liquid medium. It is most desirable that the particles exhibit minimal solubility in the liquid medium to maximize the yield of the microparticles or microspheres. For some proteins, such as insulin the decrease in solubility can be achieved by the adding of divalent cations, such as $Zn^{2+}$ to the protein. Other ions that can be used to form complexes include, but are not limited to, $Ca^{2+}$, $Cu^{2+}$, $Fe^{2+}$, $Fe^{3+}$, and the like. The solubility of the complexes are sufficiently low to allow diafiltration of the complex in an aqueous solution.

The liquid medium may also contain one or more excipients which may imbue the active agent or the microparticles with additional characteristics such as increased stability of the microparticles and/or of the active or carrier agents, controlled release of the active agent from the particles, or modified permeation of the active agent through biological tissues as discussed previously. In another form of the invention, the microparticles or microspheres are not separated from the PSEA containing solution.

Aqueous-Based Process

In another preferred embodiment, the fabrication process of the present system is of an aqueous system including an aqueous or an aqueous-miscible solvent. Examples of suitable aqueous-miscible solvents include, but are not limited to, those identified above for the continuous phase. One advantage of using an aqueous-based process is that the solution can be buffered and can contain excipients that provide biochemical stabilization to protect the active agents. This can be especially advantageous when the active agent is a protein.

Microencapsulation of Pre-Fabricated Microparticles

The microparticles or microspheres of the present invention can further be encapsulated within matrices of wall-forming materials to form microencapsulated particles. The microencapusulation can be accomplished by any process known in the art. In a preferred embodiment, microencapsulation of the microparticles or microspheres of the present invention is accomplished by an emulsification/solvent extraction processes as described below. The matrix can impart sustained release properties to the active agent resulting in release rates that persist from minutes to hours, days or weeks according to the desired therapeutic applications. The microencapsulated microparticles or microspheres can also produce delayed release formulations of the active agent. Additional methods of making microparticles and microspheres are set forth in this application.

In the emulsification/solvent extraction process, emulsification is obtained by mixing two immiscible phases, the continuous phase and the discontinuous phase (which is also known as the dispersed phase), to form an emulsion. In a preferred embodiment, the continuous phase is an aqueous phase (or the water phase) and the discontinuous phase is an organic phase (or the oil phase) to form an oil-in-water (O/W) emulsion. The discontinuous phase may further contain a dispersion of solid particles present either as a fine suspension or as a fine dispersion forming a solid-in-oil (S/O) phase. The organic phase is preferably a water immiscible or a partially water miscible organic solvent. The ratio by weights of the organic phase to the aqueous phase is from about 1:99 to about 99:1, more preferably from 1:99 to about 40:60, and most preferably from about 2:98 to about 1:3, or any range or combination of ranges therein. In a preferred embodiment, the ratio of the organic phase to the aqueous phase is about 1:3. This aspect of present invention further contemplates utilizing reverse emulsions or water-in-oil emulsion (W/O) where the oil phase forms the continuous phase and water phase forms the discontinuous phase. This further contemplates utilizing emulsions having more than two phases such as an oil-in-water-in-oil emulsion (O/W/O) or a water-in-oil-in-water emulsion (W/O/W).

In a preferred embodiment of this variation on the invention, the process of microencapsulation using the emulsification/solvent extraction process starts with preparing pre-fabricated microparticles or microspheres by the methods described earlier and an organic phase containing the wall-forming material. The pre-fabricated microparticles or microspheres are dispersed in the organic phase of the wall-forming material to form a solid-in-oil (S/O) phase containing a dispersion of the pre-fabricated microparticles or microspheres in the oil phase. In a preferred embodiment, the dispersion is accomplished by homogenizing the mixture of the microparticles or microspheres and the organic phase. An aqueous medium will form the continuous phase. In this case, the emulsion system formed by emulsifying the S/O phase with an aqueous phase is a solid-in-oil-in-water (S/O/W) emulsion system.

The wall-forming material refers to materials capable of forming the structural entity of the matrix individually or in combination. Biodegradable wall-forming materials are preferred, especially for injectable applications. Examples of such materials include but are not limited to the family of poly-lactide/poly-glycolide polymers (PLGA's), polyethylene glycol conjugated PLGA's (PLGA-PEG's), and triglycerides. In the embodiment in which PLGA or PLGA-PEG is used, the PLGA preferably has a ratio of poly-lactide to poly-glycolide of from 100:0 to 0:100, more preferably from about 90:10 to about 15:85, and most preferably about 50:50. In general, the higher the ratio of the poly-glycolide to the poly-lactide in the polymer, the more hydrophilic are the microencapsulated particles, resulting in faster hydration and faster degradation. Various molecular weights of PLGA also can be used. In general, for the same ratio of poly-glycolide and poly-lactide in the polymer, the higher the molecular weight of the PLGA, the slower is the release of the active agent, and the wider the distribution of the size of the microencapsulated particles or spheres.

When microencapsulation is practiced, the organic solvent in the organic phase (oil phase) of an oil-in-water (O/W) or solid-in-oil-in-water (S/O/W) emulsion can be aqueous immiscible or partially aqueous immiscible. What is meant by "water immiscible solvents" are those solvents which form an interfacial meniscus when combined with an aqueous solution in a 1:1 ratio (O/W). Suitable water immiscible solvents include, but are not limited to, substituted or unsubstituted, linear, branched or cyclic alkanes with a carbon number of 5 or higher, substituted or unsubstituted, linear, branched or cyclic alkenes with a carbon number of 5 or higher, substituted or unsubstituted, linear, branched or cyclic alkynes with a carbon number of 5 or higher; aromatic hydrocarbons completely or partially halogenated hydrocarbons, ethers, esters, ketones, mono-, di- or tri-glycerides, native oils, alcohols, aldehydes, acids, amines, linear or cyclic silicones, hexamethyldisiloxane, or any combination of these solvents. Halogenated solvents include, but are not limited to, carbon tetrachloride, methylene chloride, chloroform, tetrachloroethylene, trichloroethylene, trichloroethane, hydrofluorocarbons, chlorinated benzene (mono, di, tri), trichlorofluoromethane. Particularly suitable solvents are methylene chloride, chloroform, diethyl ether, toluene, xylene and ethyl acetate. What is meant by "partially water miscible solvents" are those solvents which are water immiscible at one concentration, and water miscible at another lower concentration. These solvents are of limited water miscibility and capable of spontaneous emulsion formation. Examples of partially water miscible solvents are tetrahydrofuran (THF), propylene carbonate, benzyl alcohol, and ethyl acetate.

A surface active compound can be added in connection with the microencapsulation aspect, for example, to increase the wetting properties of the organic phase. The surface active compound can be added before the emulsification process to the aqueous phase, to the organic phase, to both the aqueous medium and the organic solution, or after the emulsification process to the emulsion. The use of a surface active compound can reduce the number of unencapsulated or partially encapsulated small spherical particles, resulting in reduction of the initial burst of the active agent during the release. The surface active compound can be added to the organic phase, or to the aqueous phase, or to both the organic phase and the aqueous phase, depending on the solubility of the compound.

What is meant by the term "surface active compounds" are compounds such as an anionic surfactant, a cationic surfactant, a zwitterionic surfactant, a nonionic surfactant or a biological surface active molecule. The surface active compound should be present in an amount by weight of the aqueous phase or the organic phase or the emulsion, whatever the case may be, from less than about 0.01% to about 30%, more preferably from about 0.01% to about 10%, or any range or combination of ranges therein.

Suitable anionic surfactants include but are not limited to: potassium laurate, sodium lauryl sulfate, sodium dodecylsulfate, alkyl polyoxyethylene sulfates, sodium alginate, dioctyl sodium sulfosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Suitable cationic surfactants include, but are not limited to, quaternary ammonium compounds, such as benzalkonium chloride, cetyltrimethylammonium bromide, lauryldimethylbenzylammonium chloride, acyl carnitine hydrochlorides, or alkyl pyridinium halides. As anionic surfactants, phospholipids may be used. Suitable phospholipids include, for example phosphatidylcholine, phosphatidylethanolamine, phosphatidylserine, phosphatidyl inositol, phosphatidylglycerol, phosphatidic acid, lysophospholipids, egg or soybean phospholipid or a combination thereof. The phospholipid may be salted or desalted, hydrogenated or partially hydrogenated or natural, semisynthetic or synthetic.

Suitable nonionic surfactants include: polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxomers), polaxamines, polyvinyl alcohol, polyvinylpyrrolidone, and polysaccharides (including starch and starch derivatives such as hydroxyethylstarch (HES), methylcellulose, hydroxycellulose, hydroxy propylcellulose, hydroxy propylmethylcellulose, and noncrystalline cellulose). In a preferred form of the invention, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters are included those having short alkyl chains. One example of such a surfactant is SOLUTOL® HS 15, polyethylene-660-hydroxystearate, manufactured by BASF Aktiengesellschaft. Surface active biological molecules include such molecules as albumin, casein, heparin, hirudin, hetastarch or other appropriate biocompatible agents.

In a preferred form of the microencapsulation option of the invention, the aqueous phase includes a protein as the surface active compound. A preferred protein is albumin. The protein may also function as an excipient. In embodiments in which protein is not the surface active compound, other excipients may be included in the emulsion, added either before or after the emulsification process. Suitable excipients include, but are not limited to, saccharides, disaccharides, and sugar alcohols. A preferred disaccharide is sucrose, and a preferred sugar alcohol is mannitol.

In addition, use of channeling agents, such as polyethylene glycol (PEG), can increase the water permeation rate of the final product, which results in modification of the initial release kinetics of the active agent from the matrix, when a matrix is present, as well as degradation rate of the matrix and degradation-dependent release kinetics by modifying the hydration rate. Using PEG as the channeling agent during encapsulation can be advantageous in terms of eliminating parts of the washing process during fabrication of the small spherical particles in which PEG is used as the phase-separation enhancing agent. In addition, salinity and pH of the continuous phase can be varied to affect properties of the polymer and the resulting microparticles or microspheres including the matrix packing density, surface charge, wetting, porosity, viscosity, particle size distribution, as well as initial burst and release kinetics of the encapsulated therapeutic agent from the matrix. Salinity of the continuous phase can also be used to reduce miscibility of the two phases. Suitable salts include, but are not limited to, water-soluble phosphate, sulfate, acetate, and carbonate salts, Tris, MES, HEPES. In the embodiment in which salt is used, the salt concentration ranges from 0 to 10 M, more preferably from 1 mM to 1 M, and most preferably from 20 to 200 mM. The pH ranges from 1 to 11, more preferably from 2.5 to 9, and most preferably from 6 to 8.

After dispersing the microparticles or microspheres in the organic phase (oil phase), the continuous phase of the aqueous medium (water phase) then is vigorously mixed, for example by homogenization or sonication, with the discontinuous phase of the organic phase to form an emulsion containing emulsified droplets of embryonic microencapsulated particles. The continuous aqueous phase can be saturated with the organic solvent used in the organic phase prior to mixing of the aqueous phase and the organic phase, in order to minimize rapid extraction of the organic solvent from the emulsified droplets. The emulsification process, when practiced, can be performed at any temperature in which the mixture can maintain its liquid properties. The emulsion stability is a function of the concentration of the surface active compound in the organic phase or in the aqueous phase, or in the emulsion if the surface active compound is added to the emulsion after the emulsification process. This is one of the factors that determines droplet size of the emulsion system (embryonic microencapsulated particles) and the size and size distribution of the microencapsulated particles. Other factors affecting the size distribution of microencapsulated particles are viscosity of the continuous phase, viscosity of the discontinous phase, shear forces during emulsification, type and concentration of surface active compound, and the Oil/Water ratio.

After the emulsification, the emulsion then is transferred into a hardening medium. The hardening medium extracts the solvent in the discontinous phase from the embryonic microencapsulated particles, resulting in formation of solid microencapsulated particles having a solid polymeric matrix around the pre-fabricated microparticles or microspheres within the vicinity of the emulsified droplets. In the embodiment of an O/W or S/O/W system, the hardening medium is an aqueous medium, which may contain surface active compounds, or thickening agents, or other excipients. The microencapsulated particles are preferably spherical and have a particle size of from about 0.6 to about 300 μm, and more preferably from about 0.8 to about 60 μm. Additionally, the microencapsulated particles preferably have a narrow distribution of particle size. To reduce the extraction time of the discontinuous phase, heat or reduced pressure can be applied to the hardening medium. The extraction rate of discontinuous phase from the embryonic microencapsulated particles is an important factor in the degree of porosity in the final solid microencapsulated particles, since rapid removal, e.g., by evaporation (boiling effect), of the discontinuous phase results in destruction of the continuity of the matrix.

Figure 42A:
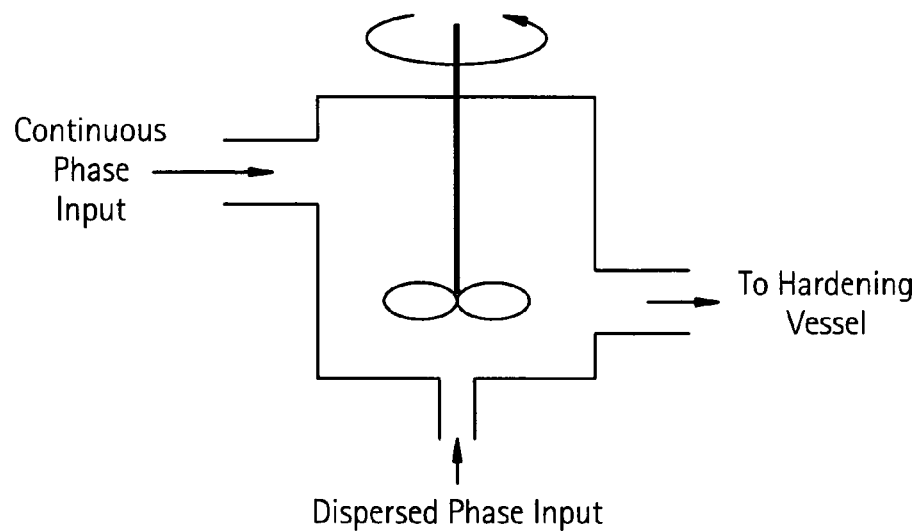
FIGS. 42A-B are schematic illustrations of the continuous emulsification reactor, where
Figure 42B:
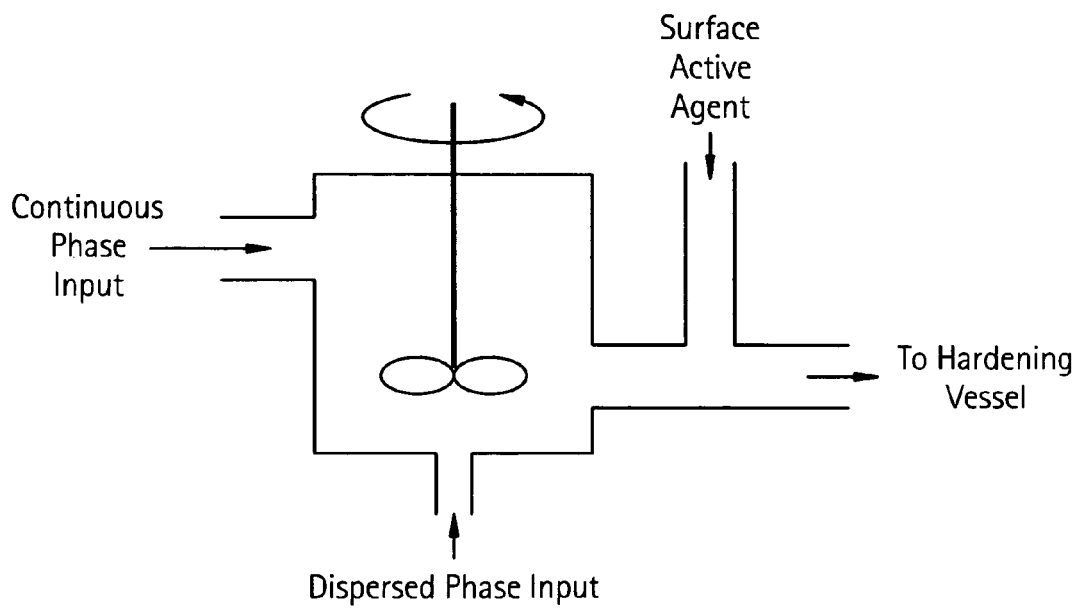

In a preferred embodiment of the emulsification process, when same is practiced, same is performed in a continuous fashion instead of a batch process. FIGS. 42a and b depicts the design of a continuous emulsification reactor which can be used in this regard. FIGS. 42a-b are schematic illustrations of the continuous emulsification reactor, where FIG. 42a is a schematic illustration of the continuous emulsification reactor when surface active compound is added to the continuous phase or the dispersed phase before emulsification, and FIG. 42b is a schematic illustration of the continuous emulsification reactor when the surface active compound is added after emulsification.

In another embodiment when encapsulation is practiced, the hardened wall-forming polymeric matrices that encapsulate the microparticles or microspheres of the active agent, are further harvested by centrifugation and/or filtration (including diafiltration), and washed with water. The remaining liquid phases can further be removed by a process such as lyophilization or evaporation.

Example 1

This Example provides a basic procedure for preparation of 500 μl batches of syringable anti-Factor VIII monoclonal antibody microspheres. Ten batches of 500 μl of the monoclonal antibody are prepared in eppendorf tubes as follows:

Preparation of 40 mM Ammonium Acetate (AA) Buffer at pH=6.5: 40 mM of AA buffer is prepared by dissolving 3.08 grams of AA (Spectrum) in 1 liter of deionized $H_2O$. The AA is readily soluble and forms a buffer solution with a pH of ~6.4. Adjust the pH to pH=6.5 with dilute ammonium hydroxide.

Preparation of 500 mL of 10% Poloxamer 188 in 40 mM AA Buffer solution: 50 grams of Poloxamer 188 (BASF) are dissolved in 500 mL of 40 mM AA Buffer (as described in step 1, only that pH adjustment is not necessary this time). The dissolution of this quantity of Poloxamer can be done in several additions. The final pH is around pH-6.4. The solution is filtered with a 0.22 μm filter and kept refrigerated.

Buffer exchange: 2 PD10 desalting columns (Amersham Biosciences) are used for 5 mL of the protein. Total column volume is 3.5 mL, and it is recommended for exchange of no more than 2.5 mL each. Each column should be rinsed with no less than 25 mL of 40 mM $NH_4OAc$ buffer to saturate the column with the buffer. Then, 2.5 mL of the anti-Factor VIII in phosphate buffer is inserted into the column followed by additional 1 mL of the $NH_4OAc$ buffer to fill the column. The protein is collected by injecting an additional 2.5 mL of the 40 mM $NH_4OAc$ buffer.

A preferred dialysis cassette is a 1 Pierce, with 3-12 mL total volume, and a MW cutoff of 10,000 Daltons to replace the buffer for 5 mL of the protein. Hydrate the cassette prior to use with deionized $H_2O$, such as by using a 5-10 mL syringe with 18G1/2 needle. First, air is injected into the cassette to separate the membrane walls. Then, the sample is injected. Air is withdrawn from the cassette to have a better sample-membrane contact. Last, the float is added on, and the cassette spins at low speed. As a rule of thumb, each buffer exchange should be at least 10× in volume.

Protein concentration: Protein concentration is determined by measuring absorbance at 280 nm and comparing to a calibration curve. If needed, the protein solution can be modified with the buffer according to the desired working concentration.

The pH of the 10% Poloxamer solution is adjusted with acetic acid to pH=6.0 and pH=6.1. The 5 mL of the protein is divided into 10 batches of 500 μL. Then, 1000 μL of 10% Poloxamer 188 in 40 mM AA at pH=6.0 is added to 5 eppendorf tubes, and 1000 μL of 10% Poloxamer 188 in 40 mM AA at pH=6.1 is added to the other 5 eppendorf tubes. The solutions are mixed well by gentle vortexing and hand mixing. The solutions should look clear to slightly hazy. The samples are incubated for 1-2 hours (~4 C) to achieve slow cooling. The samples are cooled with dry ice/ethanol mixture and lyophilized over night, or placed into a −80 C refrigerator, to remove all of the deionized $H_2O$.

Once all the deionized $H_2O$ is removed, 1 mL of $MeCl_2$/5% Acetone is added to the dry samples in each eppendorf tube. Mixing proceeds, and centrifuging is carried out at 6000-8000 RPM for 3 minutes. The supernatant is carefully removed from the centrifuge, and decanted, and washing is repeated two additional times.

After the last wash is complete, the supernatant is decanted, and additional solvent is removed using low, very gentle $N_2$ flow to avoid suspension of the powder. The dry tubes are placed on the lyophilizer to remove residual solvent, and microspheres of anti-Factor VIII monoclonal antibody are collected.

Example 2

This Example provides a basic procedure for preparation of 500 μl batches of anti-CD34 monoclonal antibody microspheres in eppendorf tubes:

Preparation of 40 mM Ammonium Acetate Buffer at pH=6.0: 40 mM of Ammonium Acetate (AA) buffer is prepared by dissolving 3.08 grams of AA (Spectrum) in 1 liter of deionized $diH_2O$. The AA is readily soluble and forms a buffer solution with a pH~ 6.4. Adjust the pH to pH=6.0 with dilute acetic acid.

Preparation of 500 mL of 15% Poloxamer 188 in 40 mM AA Buffer solution: 75 grams of Poloxamer 188 (BASF) are dissolved in 500 mL of 40 mM AA Buffer (as described in step 1, only that pH adjustment is not necessary this time). The dissolution of this quantity of Poloxamer can be carried out in several additions. The final pH is around pH~6.4. The solution is filtered with a 0.22 μm filter and kept refrigerated.

Buffer exchange: 2 PD10 desalting columns (Amersham Biosciences) are used for 5 mL of the protein. Total column volume is 3.5 mL. Each column is rinsed with no less than 25 mL of 40 mM $NH_4OAc$ buffer to saturate the column with the buffer. Then, 2.5 mL of the anti-CD34 in phosphate buffer is inserted into the column followed by additional 1 mL of the $NH_4OAc$ buffer to fill the column. The protein is collected by injecting an additional 2.5 mL of the 40 mM $NH_4OAc$ buffer. A 1 Pierce dialysis cassette with total volume 3-12 mL, and a MW cutoff of 10,000 MW is used to replace the buffer for 5 mL of the protein. The sample is injected. The float is added on, and the cassette is used to spin at low speed.

Protein concentration is determined by measuring absorbance at 280 nm and calibration curve. If needed, the protein is diluted with the buffer according to the desired working concentration. The working concentration for this procedure is determined as 1.8 mg/ml (final concentration is 0.9 mg/ml).

The pH of the 15% Poloxamer solution is adjusted with acetic acid to pH=5.8 and pH=5.9. The 5 mL of the protein is divided into 10 batches of 500 μL. 500 μL of 15% Poloxamer 188 in 40 mM AA is added at pH=5.8 to 5 eppendorf tubes, and 500 μL of 15% Poloxamer 188 is added in 40 mM AA at pH=5.9 to the other 5 eppendorf tubes.

The solutions are mixed well by gentle vortexing and hand mixing, with the solutions looking clear to slightly hazy, the samples are incubated for 1-2 hours (~4 C), effecting slow cooling.

The samples are rapidly (dried ice/ethanol mixture) and lyophilized over night to remove all of the deionized $H_2O$, or the samples are placed in a ~80 C refrigerator. Once all the deionized $H_2O$ is removed, 1 mL of $MeCl_2$/5% Acetone is added to each eppendorf tube, followed by mixing well and centrifuging at 6000-8000 RPM for 3 minutes. The supernatant is decanted and the washes are repeated two additional times.

After the last wash is complete, the supernatant is decanted, and additional solvent is removed using low and gentle $N_2$ flow. The almost dry tubes are placed on the lyophilizer to remove residual solvent, and microspheres of anti-CD34 monoclonal antibody are collected.

Example 3

The Example describes preparation of anti-Factor VIII monoclonal antibody microspheres with Poloxamer as solvent and microsphere formation under cooling. Anti-Factor VIII monoclonal antibody in 40 mM phosphate buffer at pH=7.0 and at a concentration of 5.3-5.5 (no sodium chloride) was provided by Baxter Healthcare Corporation (Bioscience Division, Hayward, Calif.). Anti-Factor VIII monoclonal antibody is a murine monoclonal antibody with a molecular weight of approximately 1501 kD, and is used for purification purposes. 5 mL of this monoclonal antibody at concentration of 5.3 mg/mL were filtered through 0.22 μm and dialyzed against 40 mM ammonium acetate buffer pH=6.5 using dialysis cassette. Protein concentration was determined by measuring absorbance at optical density of 280 nm. A 10% solution of Poloxamer 188 NF (Lutrol F68) available from BASF Corporation (Florham Park, N.J.) was prepared at pH=6.0 and filtered with 0.22 micron filter. Ammonium acetate was provided by Spectrum Chemicals (Gardena, Calif.). A dialysis cassette SLIDE-A-LYZER®, molecular weight cutoff of 10,000 and sample volume 3-12 mL was provided by Pierce (Rockford, Ill.). Aliquots of 0.5 mL of the monoclonal antibody solution were inserted into twenty 1 mL microfuge tubes. 1 mL of 10% Poloxamer solution was added to each tube containing 0.5 mL of the anti-Factor VIII (at 5.3 mg/mL), and the solution was mixed gently at room temperature and incubated at 29° C. for one-half hour.

Then, the solutions were incubated at 4° C. for 1 hour. During cooling, the clear solution became opaque as microspheres comprised of monoclonal antibody were formed. The yield of protein incorporation into microspheres was then determined in the following way: an aliquot of the microsphere suspension was removed, the microspheres were separated from the solution by centrifugation, and the protein concentration in the supernatant was determined by measuring absorbance at optical density of 280 nm. Following incubation, the tubes were flash-frozen and lyophilized. After lyophilization, the dry powder contained the anti-Factor VIII monoclonal antibody microspheres and poloxamer.

Figure 2A:
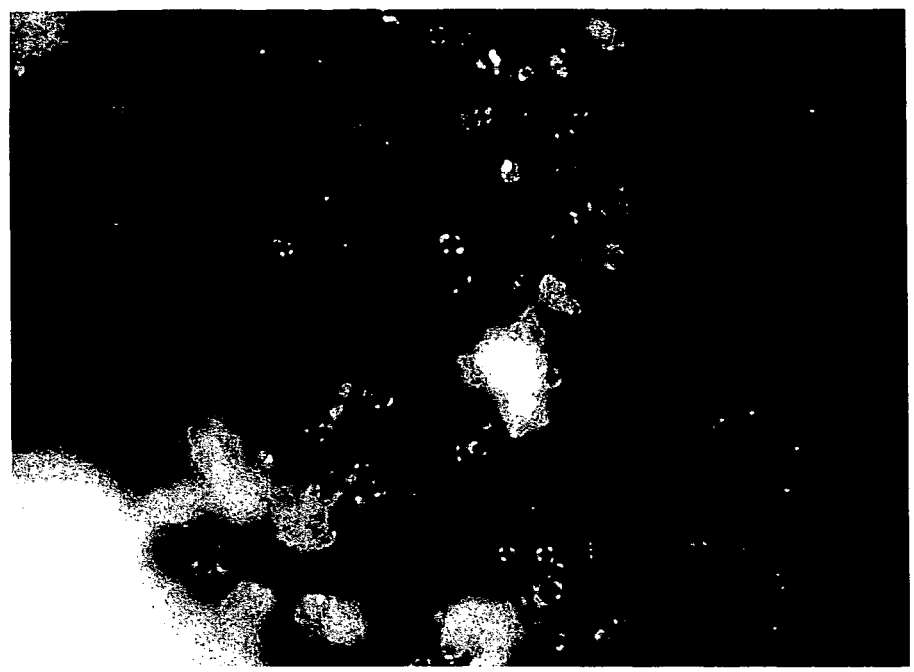
FIGS. 2a and 2b provide polarized optical microscope images of anti-Factor VIII monoclonal antibody microspheres prepared as described in Example 3.
Figure 2B:
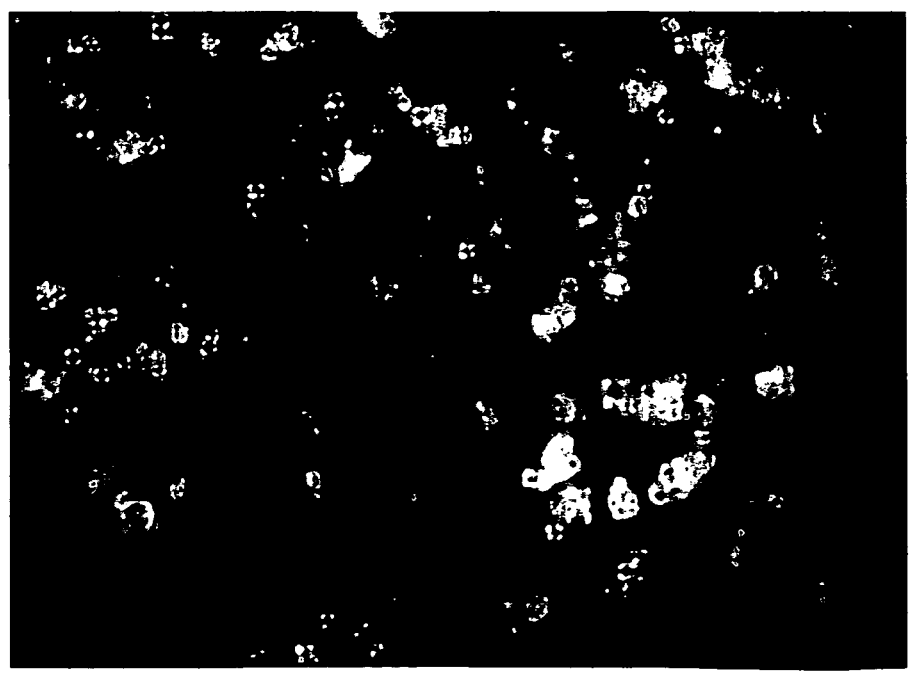

The poloxamer was removed by the addition of 1 mL of a solution of 95% methylene chloride and 5% acetone to each tube, centrifugation and removal of the supernatant. The washing procedure was repeated three times. The wet pellets were dried using nitrogen gas, and residual solvent was removed using vacuum. The dry powder was examined under light microscope. The light microscope images (FIGS. 1a and b) and polarized light microscope images FIGS. 2a and 2b show spherical particles in the size range of 0.5-5 microns. The samples were sent to SEM (Hitachi S4800, Electron Microscopy Center, Northeastern University, Boston Mass.).

Figure 3A:
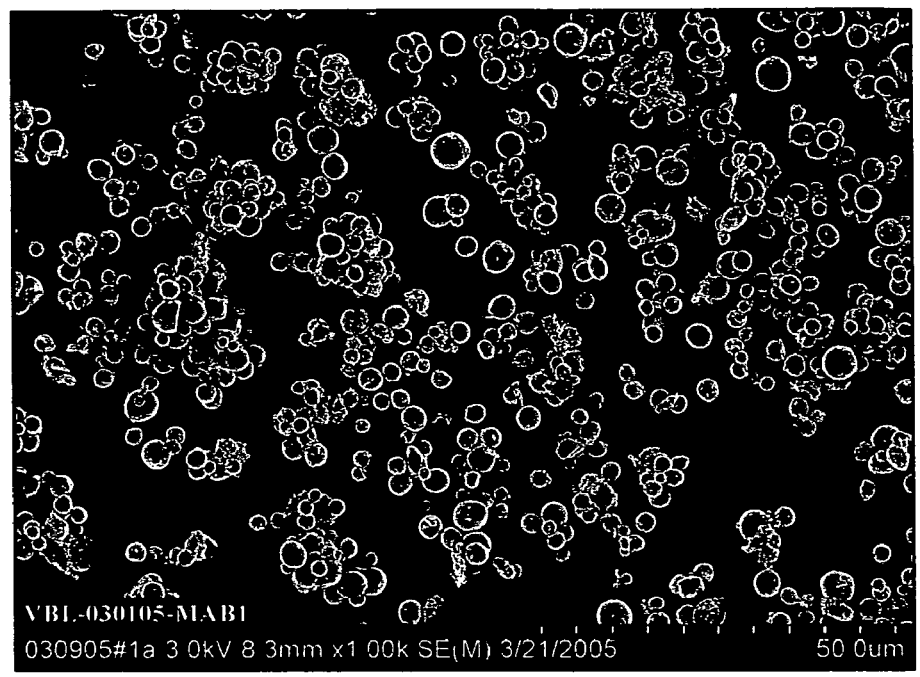
FIGS. 3a and 3b provide scanning electron micrographs of anti-Factor VIII monoclonal antibody microspheres viewed as described in Example 3.
Figure 3B:
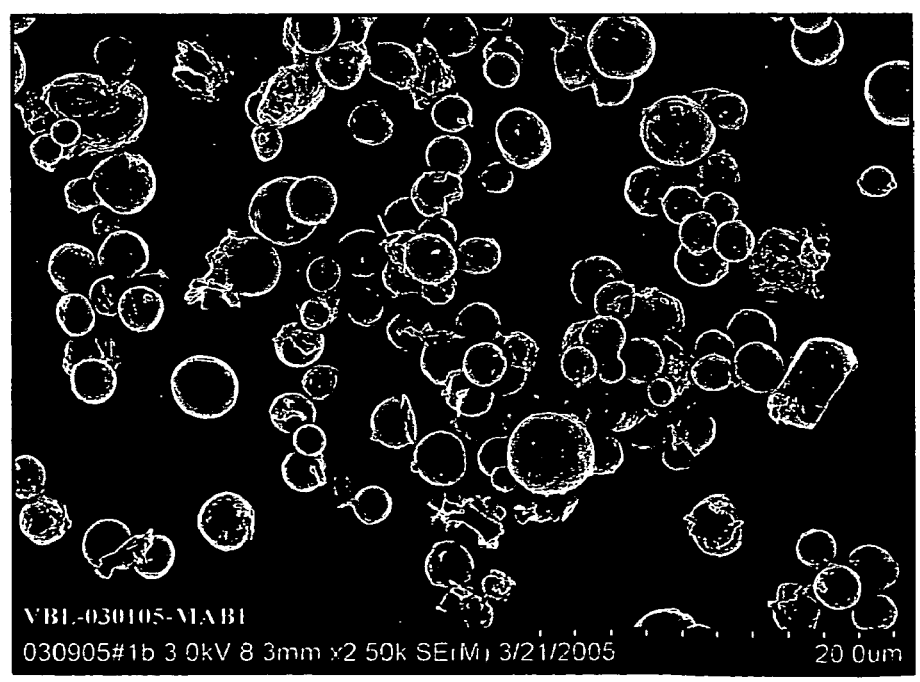

An anti-Factor VIII antibody microsphere sample was attached to the SEM specimen mount using a double-sided conductive carbon adhesive tab. A thin (10-15 nm) conductive layer of Platinum/Palladium 80:20 was applied to the sample via evaporation using a Denton DV-502 vacuum evaporator. The sample was then imaged and digitally recorded on a Hitachi S4800 Field Emission SEM using an accelerating voltage of 2-3 kV. Scanning electron micrographs FIGS. 3a and 3b show spherical particles in the size range of 0.5-6 microns.

When a polarized light passes through an isotropic sample, the sample will have no effect on the polarized light regardless of how the sample is oriented, since all crystal axes are completely equivalent. This effect is known as complete or isotropic extinction, and it occurs for crystals that have a high degree of symmetry, such as cubic systems. Noncrystalline, amorphous samples yield the same behavior. The polarized optical microscope images show the microspheres as dark circles surrounded by a bright halo. These images are independent of the sample's orientation and indicate its spherical shape and amorphous structure.

Example 4

This Example shows gel electrophoresis of anti-factor VIII monoclonal antibody microspheres prepared according to Example 3. Tris-Acetate gel, 3-8%, 1.5 mm×10 wells, Tris-Acetate SDS running buffer, NuPage LDS sample buffer, Mark 12 molecular weight Standard, and SIMPLYBLUE SAFESTAIN® drying solution were provided by Invitrogen (Carlsbad, Calif.). Gel electrophoresis is a widely-used analytical technique for the separation and characterization of proteins and peptides, and for the estimation of the molecular weight of protein.

Anti-Factor VIII monoclonal antibody microspheres prepared according to Example 3 and dissolved in phosphate buffer saline, pH=7.4, at 37° C. 40 µl of three different batches were run in parallel. 40 µl of the native anti-Factor VIII solution were run in parallel as a control. Running time was 1 hour, and voltage was 150 mV.

Figure 4A:
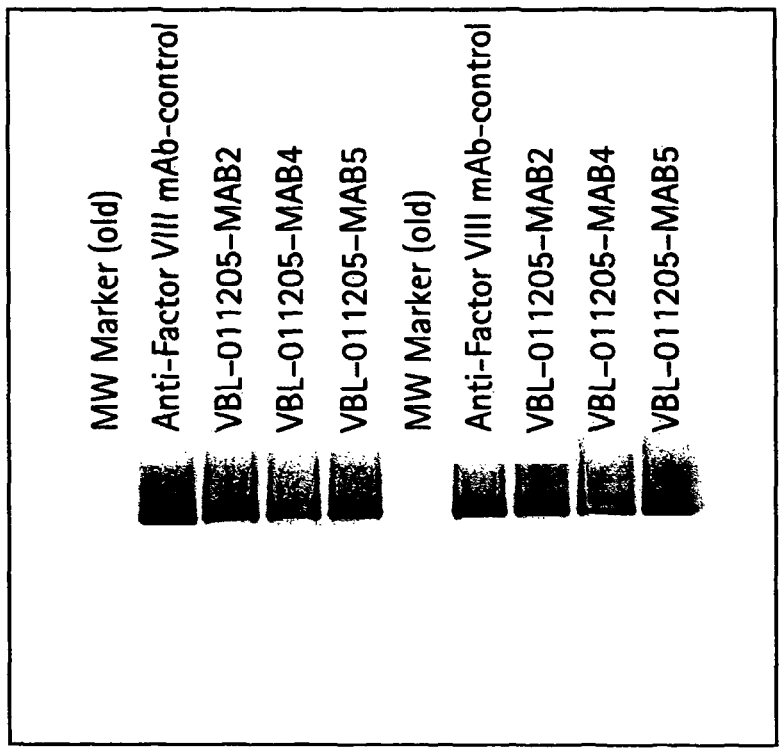
FIGS. 4a and 4b give gel electrophoresis images of anti-Factor VIII monoclonal antibody (starting material and dissolved microspheres) as described in Example 4.
Figure 4B:
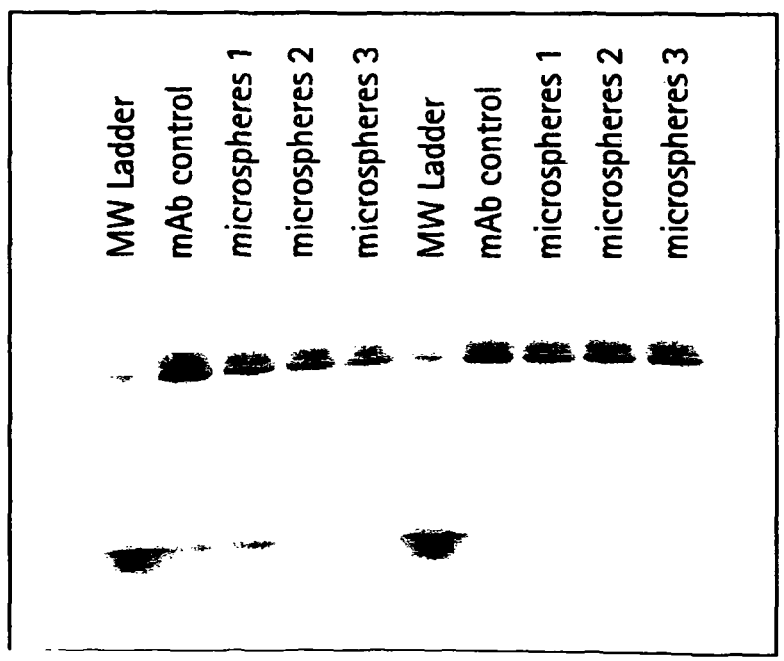

FIGS. 4a and 4b presents two gel images showing that the dissolved monoclonal antibody (released from the microspheres) migrated similarly in the gel when compared with the native monoclonal antibody. All samples migrated to the 150 kD molecular weight marker, which indicates that the protein size has not been changed as a result of the formulation. Stain intensity also was similar, and there were no stains in the gel wells, which indicate that molecular aggregation was minimal.

Example 5

This Example describes preparation of anti-factor VIII monoclonal antibody microspheres with PEG/PVP as solvent and microsphere formation under heating. Anti-Factor VIII monoclonal antibody in 40 mM phosphate buffer (no sodium chloride) of Baxter Healthcare Corporation (Bioscience Division, Hayward, Calif.) was put into microsphere form. A 25% PEG/PVP (w/v) solution in 100 mM sodium acetate buffer and pH=5.6 was prepared, using polyethylene glycol (PEG) 3350 Daltons, polyvinyl pyrrolidone (PVP), 40,000 Daltons, and Sodium acetate, available from Spectrum Chemicals (Gardena, Calif.).

400 µl of 25% PEG/PVP solution were added to 800 µl of the anti-Factor VIII monoclonal antibody solution at a concentration of 5.3 mg/mL at room temperature. The solution was mixed and incubated at 65° C. for one-half hour. Following incubation at 65° C., the solution was rapidly cooled down (quenched) by incubation in cold water to approximately 20° C. Upon cooling, the clear solution became turbid as microspheres comprised of monoclonal antibody were formed. The suspension was centrifuged and the supernatant was removed. Excess PEG/PVP was removed by washes with deionized water.

Figure 5:
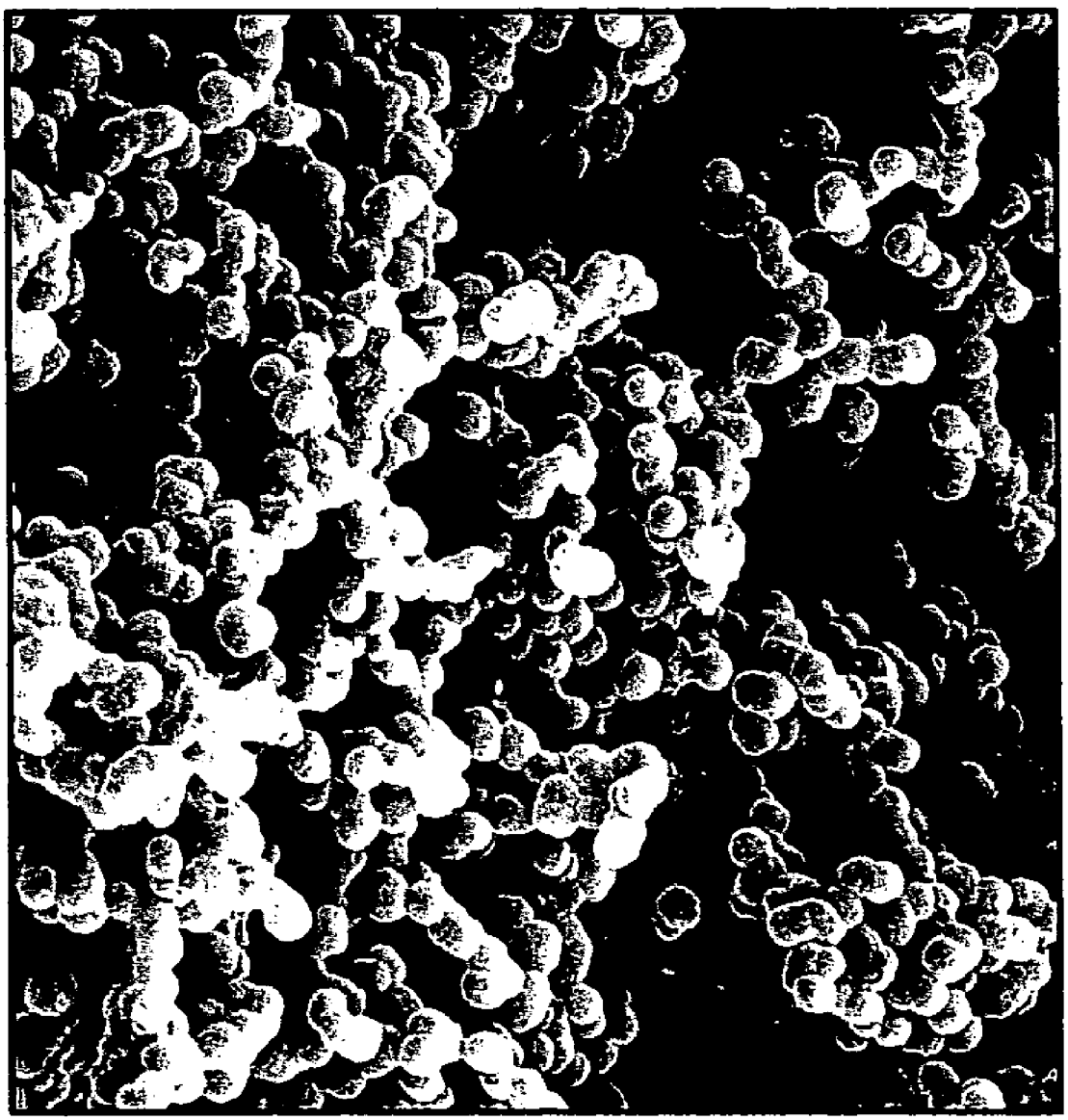
FIG. 5 gives scanning electron micrographs of anti-Factor VIII monoclonal antibody microspheres viewed as described in Example 5.

FIG. 5 presents a scanning electron microscope image of microspheres prepared according to the procedure of this Example. A sample of the microspheres was prepared and analyzed by AMRAY AMR-1000 scanning electron microscope (Electron Microscopy Center, Northeastern University, Boston, Mass.). The sample was taped onto a carbon tab using carbon-based adhesive, and mounted on the SEM specimen position. The sample was coated with Platinum/Palladium 80:20 thin coat under vacuum. The scanning electron micrographs presented in FIG. 5 show spherical particles in the size range of 1-3 µm.

Particle size distribution by laser light scattering (Beckman Coulter LS 230, Miami Fla.) was conducted on an aqueous suspension of microspheres prepared according to this Example. The distribution of the particle size was narrow, with more than 90% of the particles being smaller than 2 µm. In addition, particle size distribution by number, by surface area, and by volume were superimposed, which indicates that all particles were of approximately the same size with no apparent aggregates. See FIG. 6

Example 6

In this Example, anti-CD34 monoclonal antibody microspheres were prepared with a Poloxamer solvent, and cooling was used in microsphere formation. Anti-CD34 monoclonal antibody is a murine IgG1 Lambda monoclonal antibody with molecular weight of approximately 146 kD. This monoclonal antibody is used for extra-cellular therapy, such as stem cell selection, in conjunction with the ISOLEX® 300 and ISOLEX® 300i Magnetic Cell Selection System (Baxter Healthcare Corporation). Stem cell selection system and treatment is indicated for processing autologous peripheral blood progenitor cell (PBPC) products to obtain a CD34+ cell enriched population intended for hematopoietic reconstitution after myeloablative therapy in patients with CD34-negative tumors.

Anti-CD34 monoclonal antibody in 0.02M sodium phosphate buffer with 0.15M sodium chloride and 0.001% Tween 80, at pH=5.5 and at a concentration of 2.3-2.5 mg/mL, was provided by Baxter Healthcare Corporation (Bioscience Division, Hayward, Calif.). 5 mL of the monoclonal antibody at a concentration of 2.2 mg/mL were filtered through 0.22 µM and dialyzed against 40 mM ammonium acetate buffer, pH=6.0. A 15% solution of Poloxamer 188 NF (Lutrol F68), available from BASF Corporation (Florham Park, N.J.), the solution being at pH=6.0, was prepared and filtered with 0.22 µm filter. Ammonium Acetate was provided by Spectrum Chemicals (Gardena, Calif.). A dialysis cassette SLIDE-A-LYZER®, molecular weight cutoff of 10,000 and sample volume 3-12 mL was provided by Pierce (Rockford, Ill.). Aliquots of 0.5 mL of the monoclonal antibody solution were inserted to twenty 1 mL microfuge tubes. 0.5 mL of the 15% Poloxamer solution was added to each tube containing 0.5 mL of the anti-CD34, at 2.0 mg/mL and the solution was mixed gently at room temperature and incubated at 29° C. for one-half hour.

Then, the solutions were incubated at 4° C. for 1 hour. During cooling, the clear solution became opaque as microspheres comprised of monoclonal antibody were formed. The yield of protein incorporation into microspheres was then determined in the following manner: an aliquot of the microsphere suspension was removed, the microspheres were separated from the solution by centrifugation, and protein concentration in the supernatant was determined by measuring absorbance at optical density of 280 nm. Following incubation, the tubes were flash-frozen and lyophilized. After lyophilization, the dry powder contained the anti-CD34 monoclonal antibody microspheres and poloxamer.

Figure 7A:
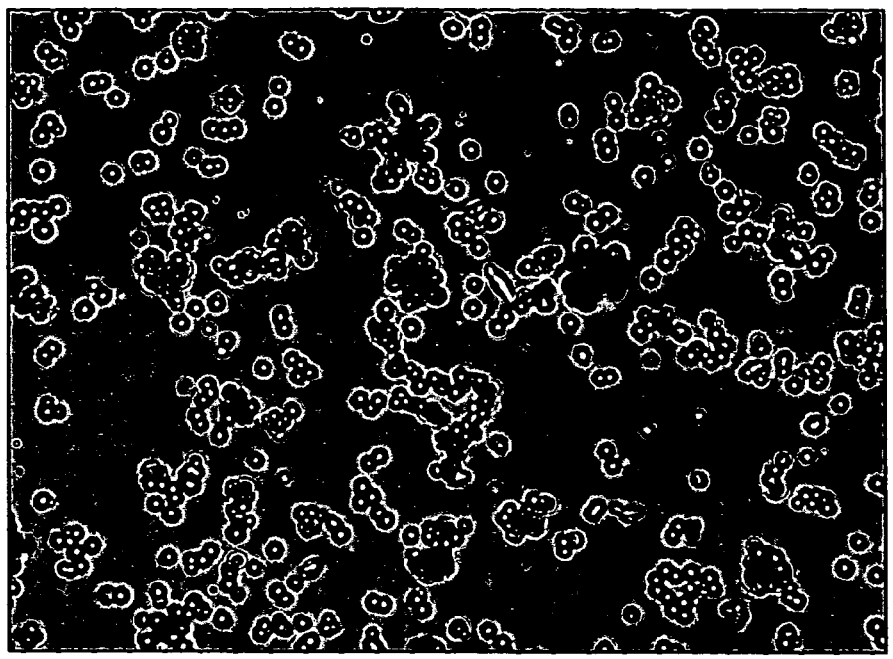
FIGS. 7a and 7b provide optical microscope images of anti-CD34 monoclonal antibody microspheres prepared as described in Example 6.
Figure 7B:
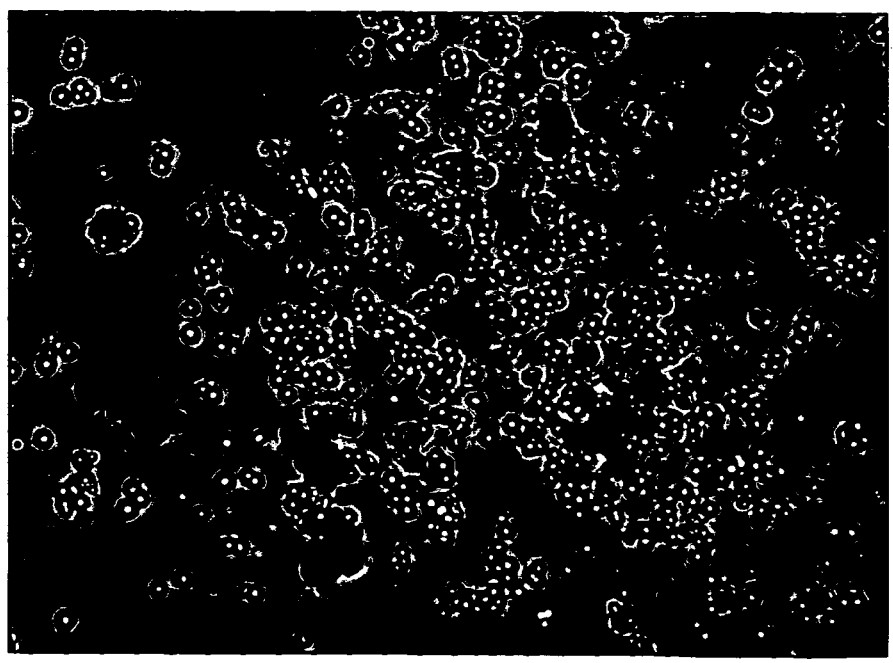
Figure 8:
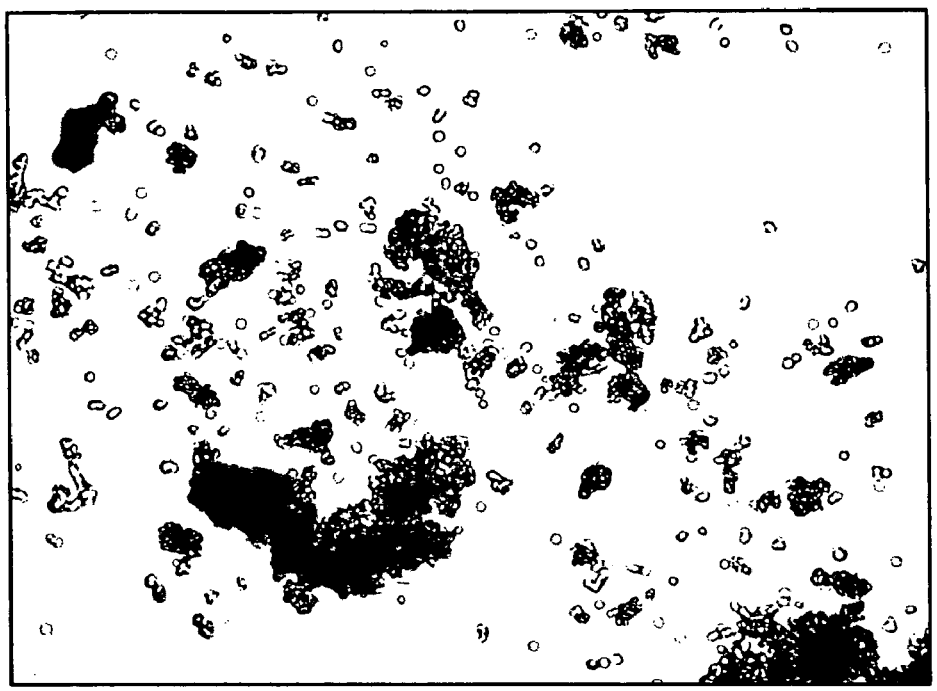
FIG. 8 is an optical microscope image of anti-CD34 monoclonal antibody microspheres prepared as described in Example 8.
Figure 9:
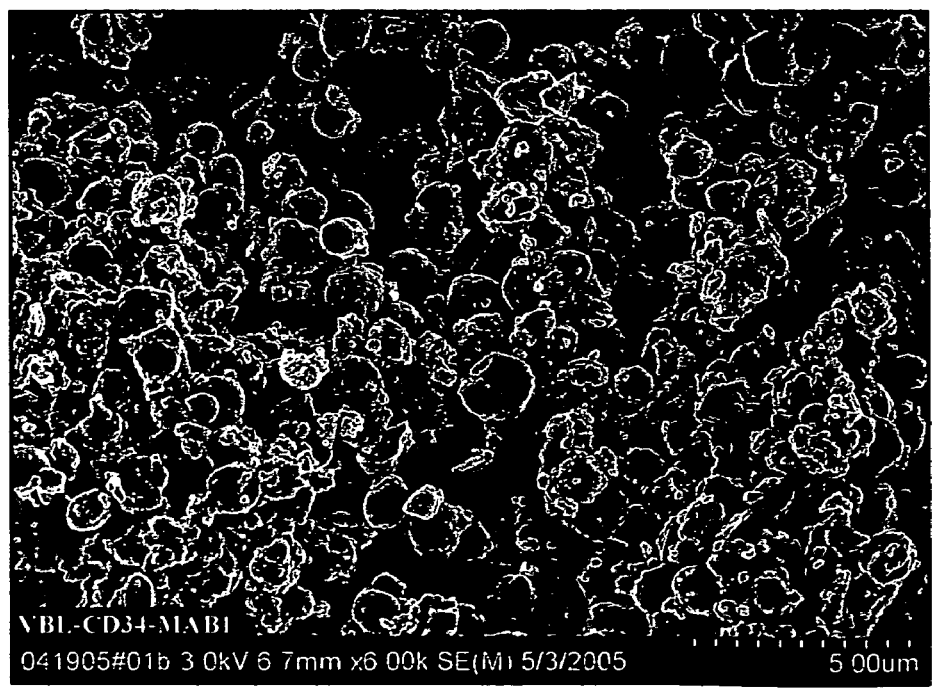
FIG. 9 is a scanning electron micrograph of anti-CD34 monoclonal antibody microspheres prepared as described in Example 6.
Figure 10:
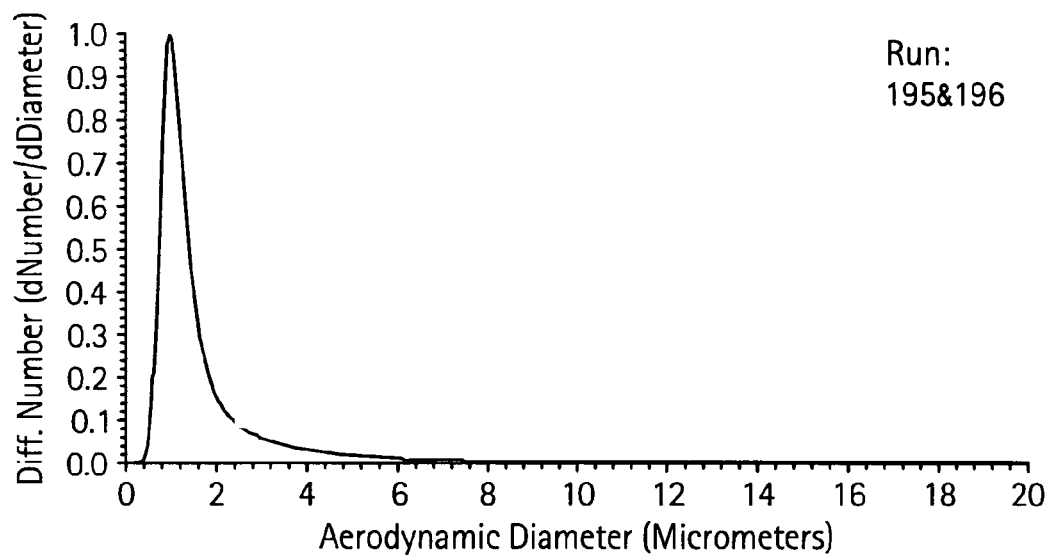
FIG. 10 reports particle size distribution by number distribution of anti-CD34 monoclonal antibody microspheres prepared as described in Example 6.
Figure 11:
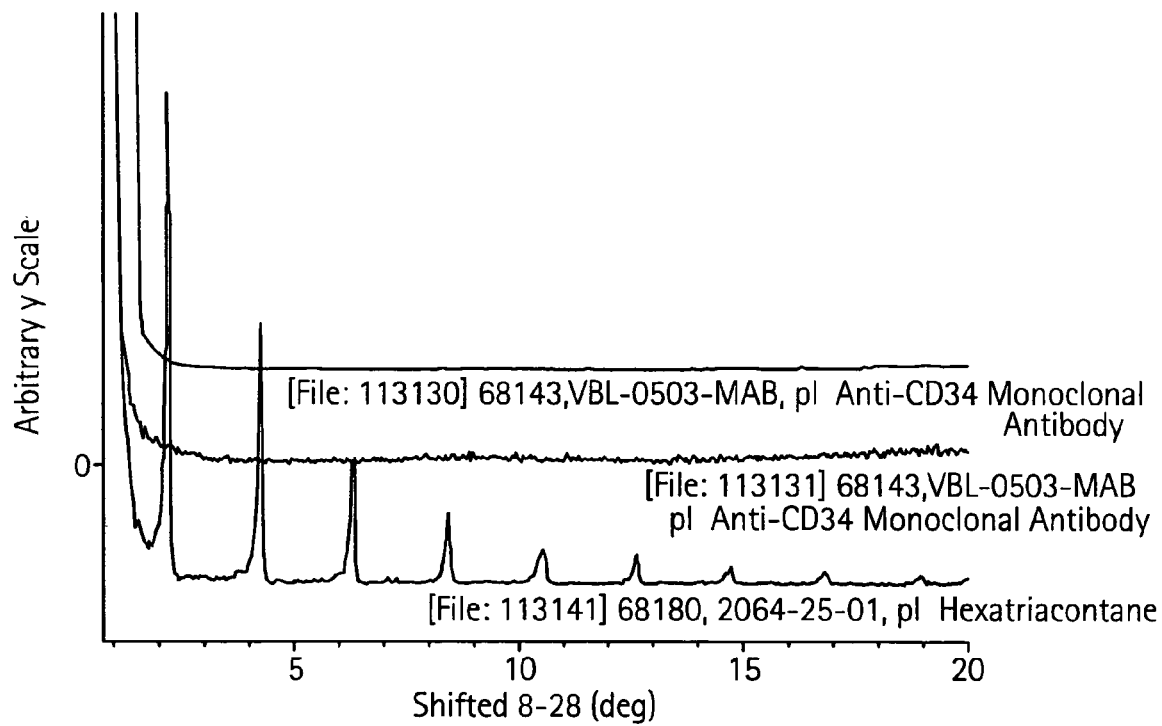
FIG. 11 gives X-ray powder diffraction of anti-CD34 monoclonal antibody microspheres (with 2 slit configuration) and of hexatriacontane:silicon mixture as described in Example 10.
Figure 12:
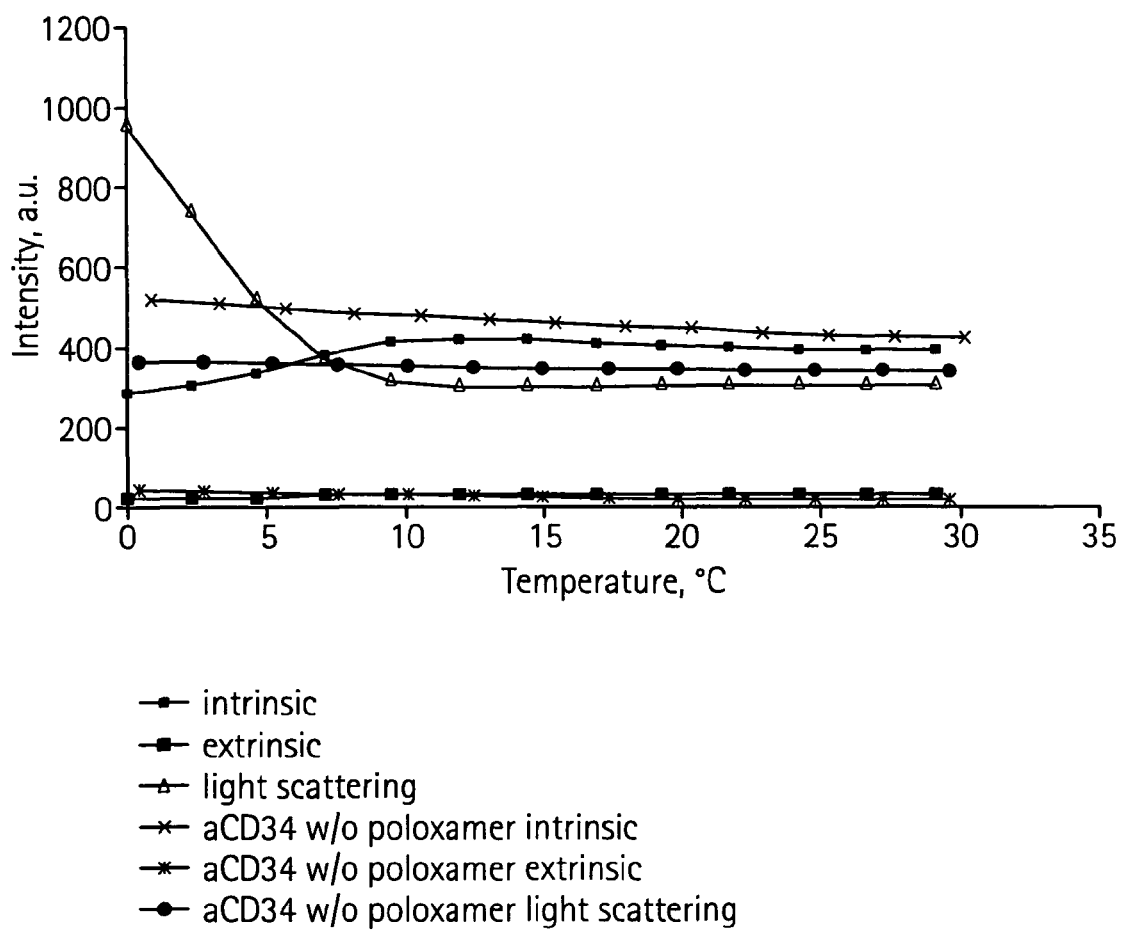
FIG. 12 reports fluorescence monitoring of conformational stability of anti-CD34 monoclonal antibody microspheres during cooling with poloxamer as described in Example 7.

The poloxamer was removed by the addition of 1 mL of a solution of 95% methylene chloride and 5% acetone to each tube, followed by centrifugation and removal of the supernatant. The washing procedure was repeated three times. The wet pellets were dried using nitrogen gas, and residual solvent was removed using vacuum. The dry power was examined under light microscope and samples were sent to SEM. Light microscope images FIGS. 7a and b show spherical particles in the size range of 0.5-5 microns. Scanning electron micrographs of anti-CD34 monoclonal antibody microspheres were viewed as described in Example 4, above (FIG. 9).

Particle size distribution by aerodynamic time-of-flight measurement (TSI Aerosizer) was conducted on 5 mg dry powder of anti-CD34 monoclonal antibody microspheres prepared according to this Example. The distribution of the particle size by number was narrow, with mean size aerodynamic diameter of 1.3 µm, and 95% of the particles were smaller than 3.6 μm (FIG. 10).

Example 7

Conformational stability of the anti-CD34 monoclonal antibody microspheres of Example 6 was also monitored. 1.5 mL of anti-CD34 in 40 mM ammonium acetate buffer, at pH=6.0 and at a concentration of 1.6 mg/mL, were mixed with 1.5 mL of 15% poloxamer in 40 mM ammonium acetate (pH=6.0 at 25° C.). 3 μL of 10 mM solution of fluorescent dye 8-anilinonaphthalene-1-sulphonic acid (ANS) were added, and the solution was gently mixed and transferred to fluorescence cell.

Conformational stability of anti-CD34 antibody was monitored by using intrinsic fluorescence of the protein tryptophane and tyrosine residues and extrinsic fluorescence of the ANS dye. Formation of particles in the fluorescence cell was followed using detection of the second overtone at 500 nm of elastic scattering of the light excited at 250 nm. The Example was performed using a Cary Eclipse Biomelt fluorescence spectrophotometer equipped with Peltier-thermostated multicell holder accessory. The sample was incubated at 25° C. for 1 minute, heated to 31° C. at the rate 0.06 degrees Celsius per minute, cooled to 2° C. at the rate of 5 degrees Celsius per minute, and incubated at this temperature for 1 hour. Control samples included 10 μM ANS in 40 mM ammonium acetate (pH=6.0), 10 μM ANS in 40 mM ammonium acetate 7.5% poloxamer (pH=6.0), and 0.8 mg/mL anti-CD34 monoclonal antibody with 10 μM ANS in 40 mM ammonium acetate (pH=6.0).

FIG. 12 presents fluorescence monitoring results of the conformational stability of anti-CD34 monoclonal antibody. Fluorescence data support that the protein conformation remained intact during microsphere formation.

Example 8

According to this Example anti-CD34 monoclonal antibody microspheres were prepared with Poloxamer or PEG/PVP solvents, and incorporated heating. Anti-CD34 monoclonal antibody in 0.02M sodium phosphate buffer with 0.15M sodium chloride and 0.001% Tween 80, at pH=5.5 and at the concentration of 2.3-2.5 mg/mL, was provided by Baxter Healthcare Corporation (Bioscience Division, Hayward, Calif.). Desalting columns, sample volume 2.5 mL, available form Amersham Bioscience (Piscataway, N.J.), were used to dialyze 5 mL of anti-CD34 monoclonal antibody against 40 mM ammonium acetate buffer (Spectrum Chemicals, Gardena, Calif.) at pH=6.3. Protein concentration was determined by measuring absorbance at optical density of 280 nm. Aliquots of 0.5 mL of the monoclonal antibody solution were inserted to ten 1 mL microfuge tubes, and 0.3 mL aliquot of 15% Poloxamer 188 NF (Lutrol F68 by BASF Corporation, Florham Park, N.J.) was added to a tube containing 0.5 mL of the anti-CD34, at 2.1 mg/mL, and the solution was mixed gently at room temperature and incubated at 70° C. for one-half hour.

Following incubation at 70° C., the solution was rapidly cooled down (quenched) by incubation in cold water to 23° C. Upon cooling, the clear solution became turbid as microspheres comprised of monoclonal antibody were formed. The suspension was centrifuged, and the supernatant was removed. Excess poloxamer was removed by washes with deionized water. Optical microscope image (FIG. 8) show spherical particles in the size range of 0.5-5 μm.

Example 9

In this Example, preparation of anti-CD34 monoclonal antibody microspheres is described with PEG/PVP as solvent and microsphere formation under cooling. Anti-CD34 monoclonal antibody in 0.02M sodium phosphate buffer with 0.15M sodium chloride and 0.001% Tween 80, at pH=5.5 and at the concentration of 2.3-2.5 mg/mL, was provided by Baxter Healthcare Corporation (Bioscience Division, Hayward, Calif.). Polyethylene glycol (PEG) 3350 Da, Polyvinyl pyrrolidone (PVP) 40,000 Da, and sodium acetate were all provided by Spectrum Chemicals (Gardena, Calif.).

25% PEG/PVP solution (pH=5.6) in 100 mM sodium acetate buffer was prepared and filtered through 0.22 pin filter. 5 mL of the monoclonal antibody at the concentration of 2.2 mg/mL was filtered through 0.22 μm filter and dialyzed using a dialysis cassette SLIDE-A-LYZER® (molecular weight cutoff of 10,000 and sample volume 3-12 mL, provided by Pierce (Rockford, Ill.)). The monoclonal antibody was dialyzed against 40 mM ammonium acetate buffer, pH=6.0. Then, 200 μl of 25% PEG/PVP solution (w/v) was added to 500 μl of the anti-CD34 monoclonal antibody at concentration of 2.0 mg/mL and the solution was mixed gently at room temperature and incubated at 29° C. for on-half hour. The process continued as described in Example 6, but for the removal of PEG/PVP, as opposed to poloxamer, by washes with a 95% methylene chloride/5% acetone solution.

Example 10

This Example shows X-ray powder diffraction (XRPD) of monoclonal antibody microspheres prepared according to Example 6. High resolution X-ray powder diffraction (XRPD) analyses were acquired using a Shimadzu XRD-6000 X-ray powder diffractometer, equipped with a long fine focus X-ray tube, using Cu Kα radition (SSCI, West Lafayette, Ind.).

The tube voltage and amperage were set to 40 kV and 40 mA, respectively. The divergence and scattering slits were set at 1° and the receiving slit was set at 0.15 mm. Alternately, the divergence and scattering slits were set at 0.5° and the receiving slit was set at 0.15 mm. Diffracted radiation was detected by a NaI scintillation detector. A θ-2θ continuous scan at 0.5° per minute (4.8 seconds per 0.02° step) from 1 to 20° 2θ was used. A silicon standard was analyzed to check the instrument alignment. Data were collected and analyzed using XRD-6000 v. 4.1. A low angle standard consisting of an 80:20 mixture of hexatriacontane:silicon was run to demonstrate the instrumental resolution at lower angles for a well-defined 'd' value.

FIG. 11 presents XRPD patterns of the anti-CD34 monoclonal antibody microspheres and of the 80:20 mixture of hexatriacontane:silicon. The XRPD of the hexatriacontane: silicon mixture has distinctive peaks which are indicative of the crystalline state, whereas the XRPD pattern of the antibody microspheres is continuous and has no distinct peaks which is typical of the amorphous, non-crystalline state.

Example 11

Anti-CD34 was formulated into microspheres according to the invention, generally following Example 2. The microspheres were suspended into a solution of 5% PEG 3350 at the concentrations shown in Table I. A volume of suspended microspheres was aspirated into a syringe and delivered through a 25 Gauge injectability needle into a 4 lb store bought pork shoulder. Each injection was carried out in 20 seconds or less, with no clogging. The results of the syringeability, which in this Example indicates the ability to aspirate the microsphere suspension through the 25 Gauge needle into the syringe and to fully inject the syringe contents into the pork, are recorded in Table I.

TABLE I

| Anti-CD 34 microsphere concentration (mg/mL) | Volume (mL) | Syringeability | Injectability |
|---|---|---|---|
| 50 | 0.3 | Yes | Yes |
| 200 | 0.15 | Yes | Yes |

The results reported in Table I show that high concentrations of these protein microspheres can be aspirated into a fine (25 Gauge) needle and injected successfully therefrom. This provides an indication of injectability in a subcutaneous environment, through skin and into muscle.

Example 12

Insulin microspheres containing greater than 90% weight-by-weight recombinant human insulin were formulated into microspheres according to the invention. (See Example 13.) The insulin microspheres were suspended into a solution of 5% PEG 3350 at the concentrations shown in Table II. One mL of suspended microspheres was aspirated into the syringe and delivered through a 28 Gauge insulin needle (27 Gauge for the 100 mg/ml concentration) into a 10 lb store bought smoked ham. Each injection was carried out in 20 seconds or less, with no clogging. The results of the syringeability, which in this Example indicates the ability to aspirate the microsphere suspension through the 28 (or 27) Gauge needle into the syringe, and injectability, which in this Example indicates the ability to fully inject the syringe contents into the ham, are recorded in Table II.

TABLE I

| Insulin microsphere concentration (mg/mL) | Volume (mL) | Syringeability | Injectability |
|---|---|---|---|
| 200 | 1 | Yes | Yes |
| 300 | 1 | Yes | Yes |
| 350 | 1 | Yes | Yes |
| 400 | 1 | Yes | Partially |

The results reported in Table II show that high concentrations of these protein microspheres can be aspirated into a fine (27 or 28 Gauge) needle and injected successfully therefrom into a 10 lb piece of ham. This later step provides a rough indication of injectability in a subcutaneous environment. The 300 mg/ml injection was made with 5.8 newtons of force.

Example 13

Insulin microparticles or microspheres are prepared by a general method. A solution buffered at pH 5.65 (0.033M sodium acetate buffer) containing 16.67% PEG 3350 was prepared. A concentrated slurry of zinc crystalline insulin was added to this solution while stirring. The insulin concentration in the final solution was 0.83 mg/mL. The solution was heated to about 85 to 90° C. The insulin crystals dissolved completely in this temperature range within five minutes. Insulin small spherical particles started to form at around 60° C. when the temperature of the solution was reduced at a controlled rate. The yield increased as the concentration of PEG increased. This process yields microparticles or microspheres with various size distributions with a mean of 1.4 µm.

The insulin microparticles or microspheres formed were separated from PEG by washing the microspheres via diafiltration under conditions in which the microspheres do not dissolve. The insulin microspheres were washed out of the suspension using an aqueous solution containing $Zn^{2+}$. The $Zn^{2+}$ ion reduces the solubility of the insulin and prevents dissolution that reduces yield and causes microsphere agglomeration.

Figure 14:
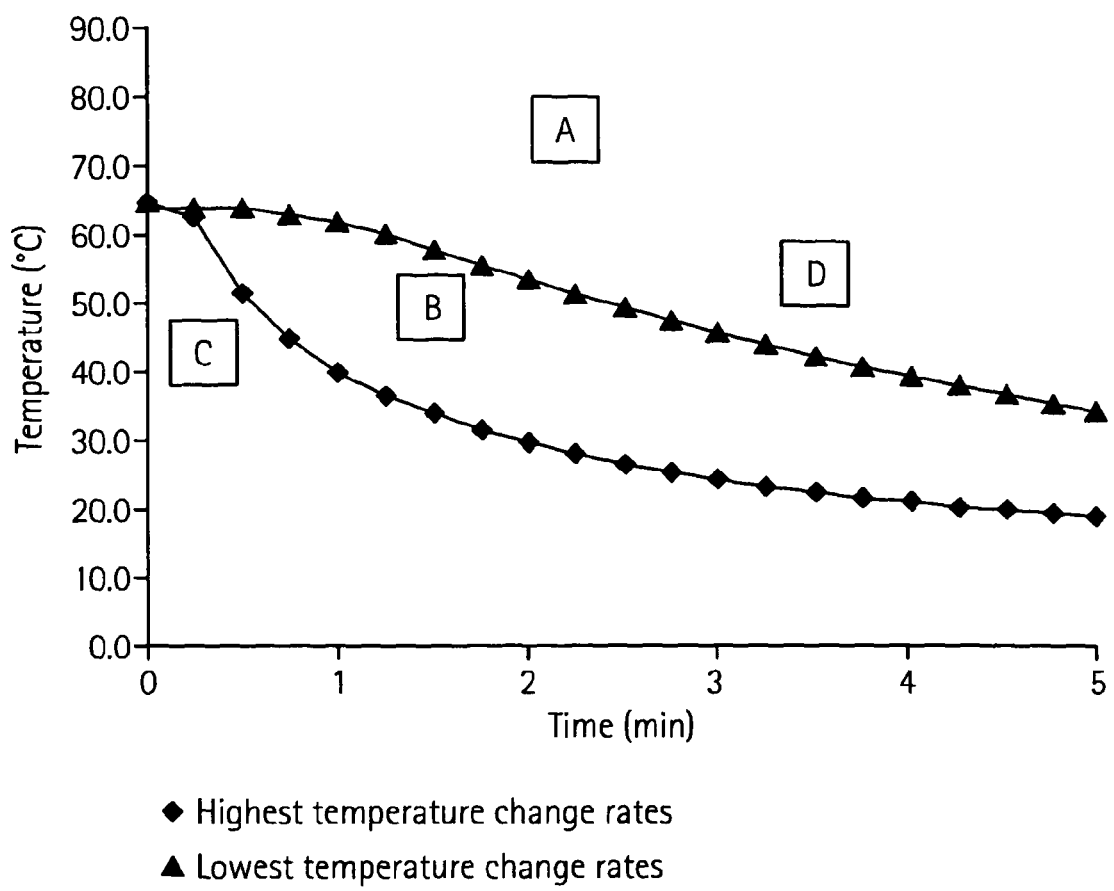
FIG. 14 is a cooling temperature profile.

FIG. 14 shows the influence of solution temperature and rate of cooling on the phase change of insulin in a buffered polymer solution. At temperatures above 60° C., insulin remains in solution (Region A in FIG. 14). Region B in FIG. 14 represents the area of optimal small spherical particle formation bounded by the highest (♦ symbols in FIG. 14) and lowest (▲ symbols in FIG. 14) temperature change rates observed in the heat exchanger. Faster cooling rates (Region C in FIG. 14) result in the formation of very fine non-spherical particles, whereas slower cooling rates (Region D in FIG. 14) results in a mixture of various sized small particles along with irregularly shaped particles and a flocculent precipitate.

Figure 15:
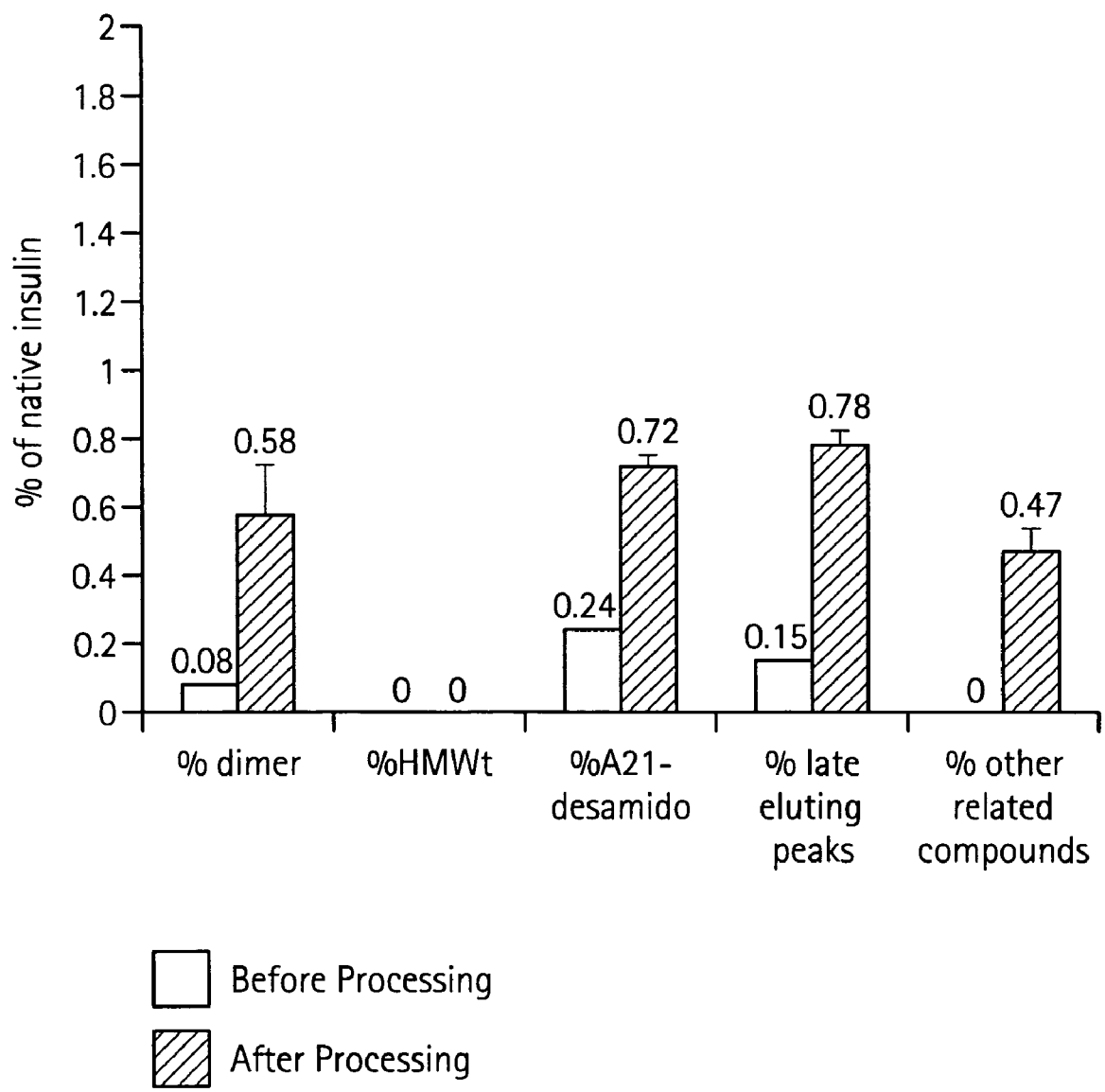
FIG. 15 is an HPLC analysis showing overall maintenance of chemical stability of insulin when prepared into small spherical particles.

FIG. 15 shows the chemical stability of insulin during the microsphere fabrication process. HPLC analysis indicated no increase in high molecular weight compounds associated with the process and increases over the starting insulin material in % dimer, % A21 desamido insulin, and % other compounds were within USP limits.

Figure 16A:
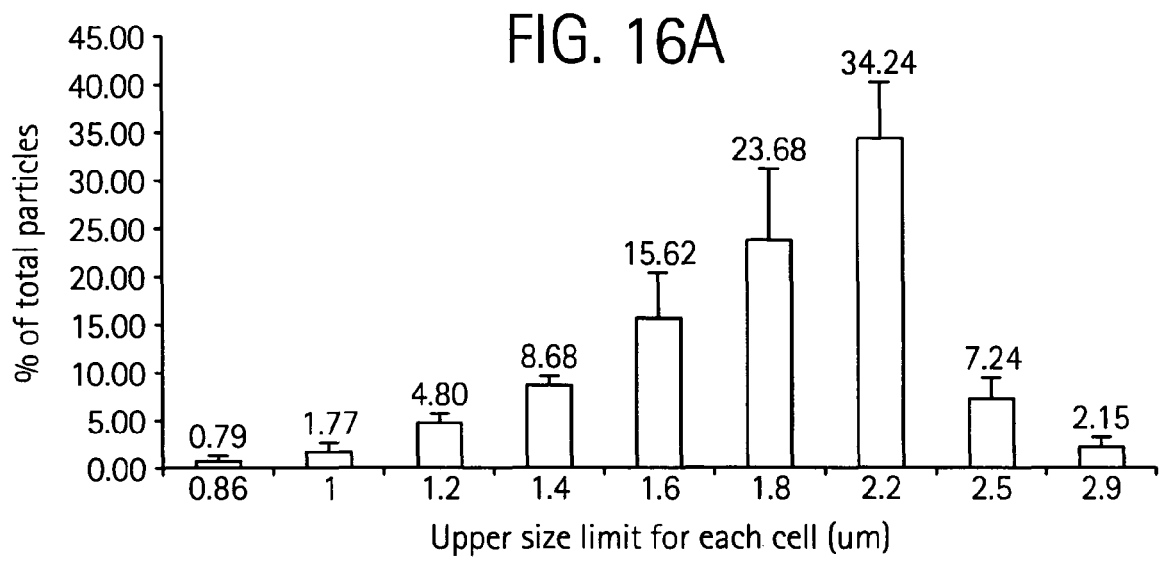
FIGS. 16a and 16b are schematics demonstrating batch-to-batch reproducibility.
Figure 16B:
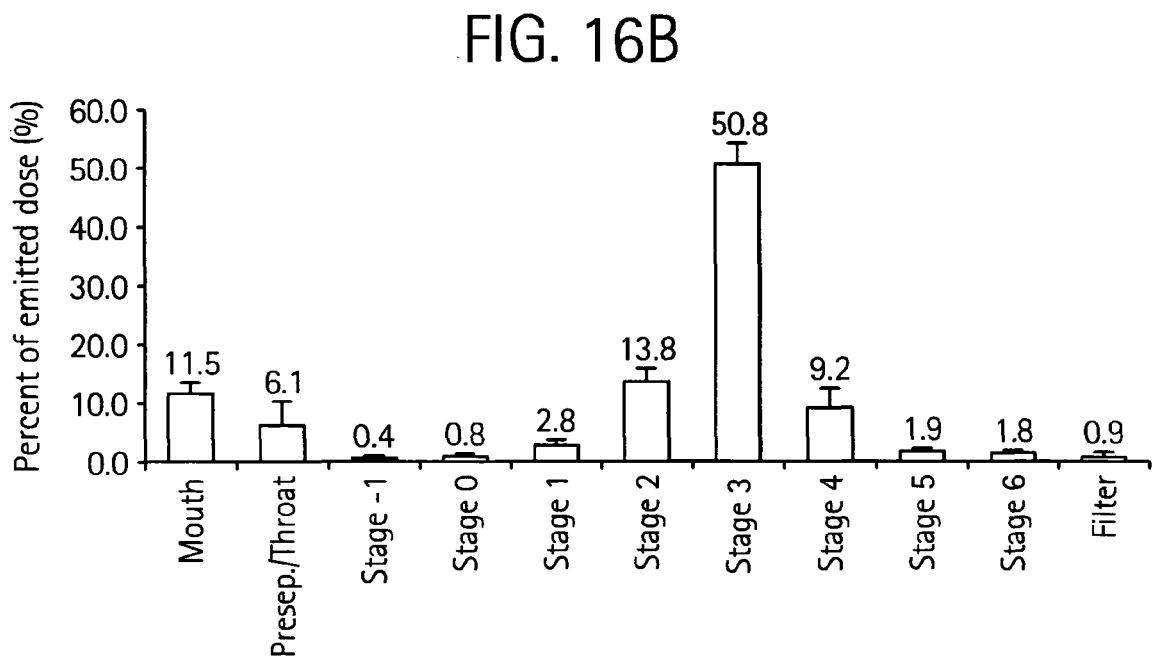

FIG. 16*a* shows the particle size distribution for insulin small spherical particles. The data were obtained using the Aerosizer time-of-flight method. For all six batches produced, greater than 96% of the particles fell between 0.86 and 2.9 microns and greater than 60% fell between 1.6 and 2.5 microns. Less than 1.1% of the small spherical particles fell outside of the size range covered by the graph. FIG. 16*b* shows particle size distribution for insulin small particles obtained using an Anderson Cascade Impactor. The data is an average (mean±SD) of results from six batches of insulin small spherical particles delivered from a cyclohaler device at 60 LPM. The ECD for stages 1, 2, 3 and 4 were 4.4, 3.3, 2.0 and 1.1 µm, respectively.

Figure 29:
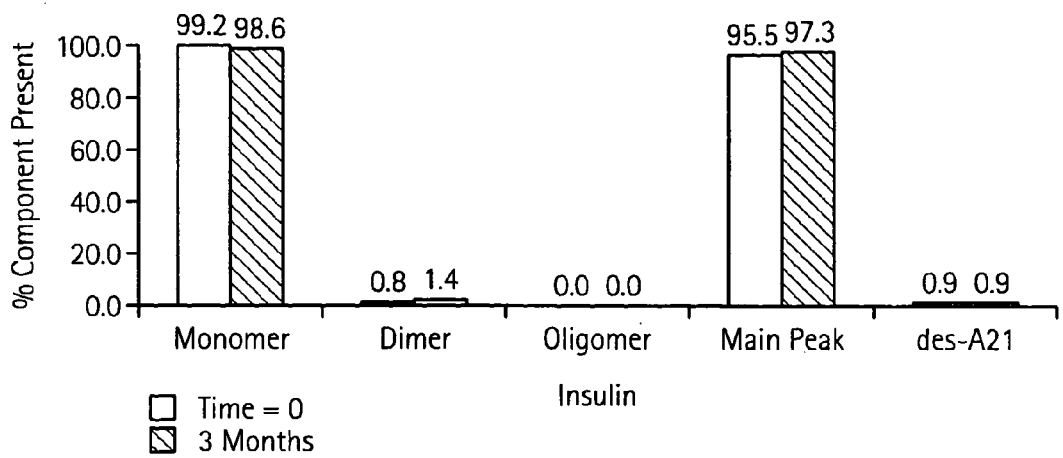
Figure 30:
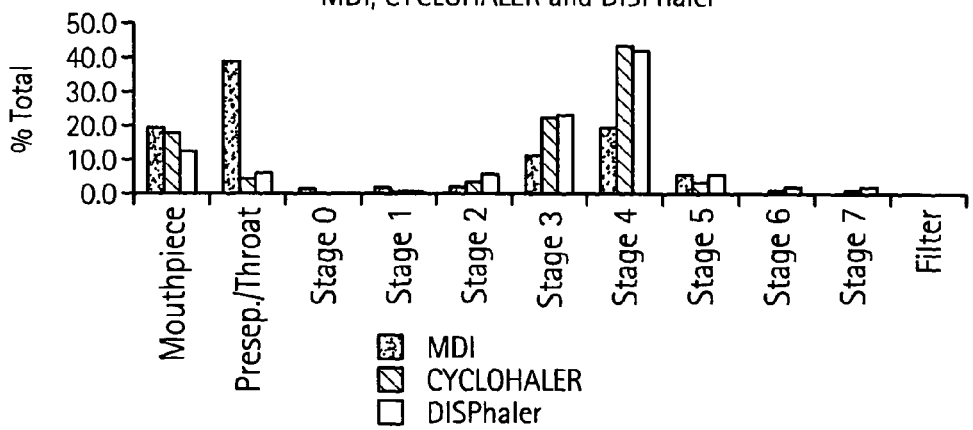
FIG. 30 is a chart comparing aerodynamic performance of Insulin using three inhalation devices.

FIG. 29 is a bar graph that shows that insulin in a microsphere form is stable after storage in HFA 134a propellant. In FIG. 30, the aerodynamic performance of small spherical particles containing insulin is compared using three different inhalation devices, a MDI, a Cyclohaler DPI and a Disphaler DPI.

Figure 31:
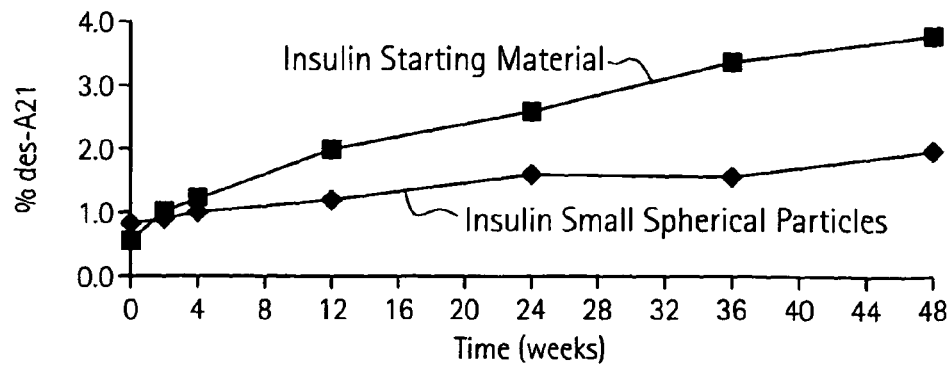
FIG. 31 is a chart of stability data of Insulin small spherical particles compared to Insulin starting material stored at 25° C.
Figure 32:
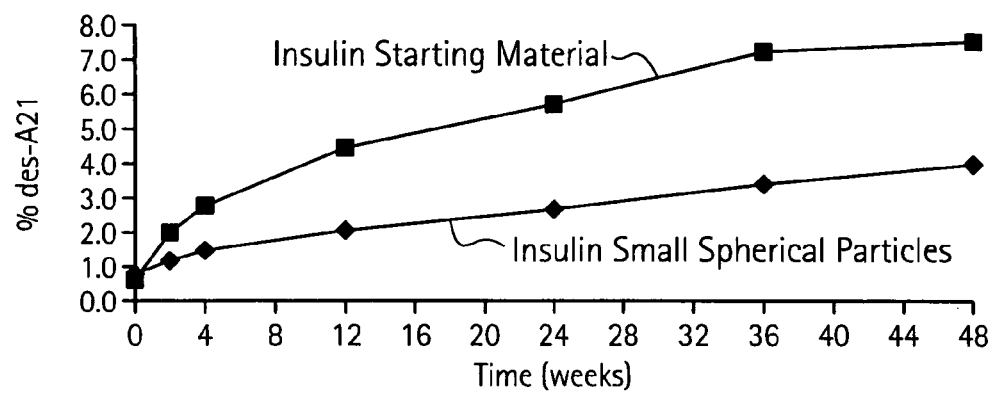
FIG. 32 is a chart of stability data of Insulin small spherical particles compared to Insulin starting material stored at 37° C.
Figure 33:
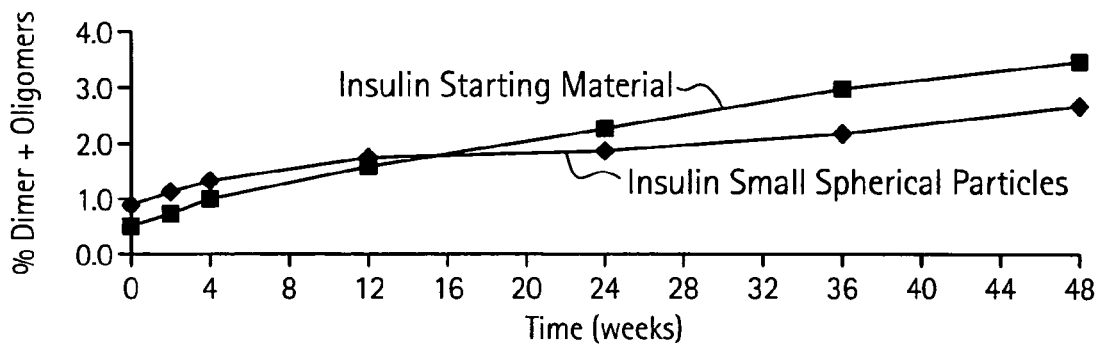
FIG. 33 is a chart of stability data of Insulin small spherical particles compared to Insulin starting material stored at 25° C.
Figure 34:
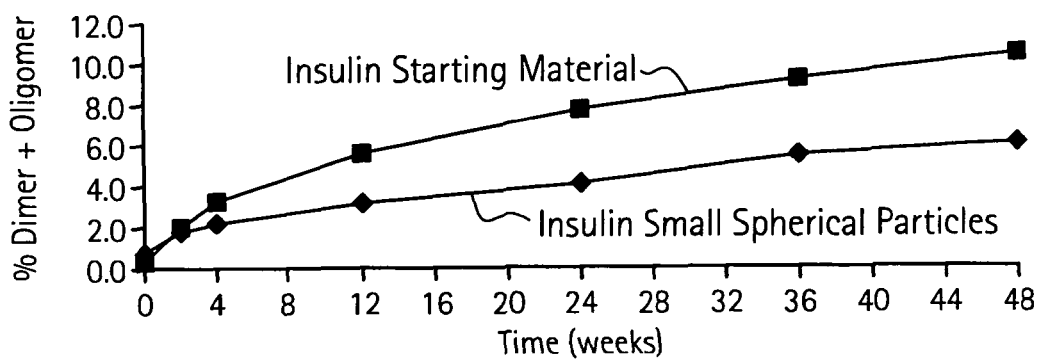
FIG. 34 is a chart of stability data of Insulin small spherical particles compared to Insulin starting material stored at 37° C.
Figure 35:
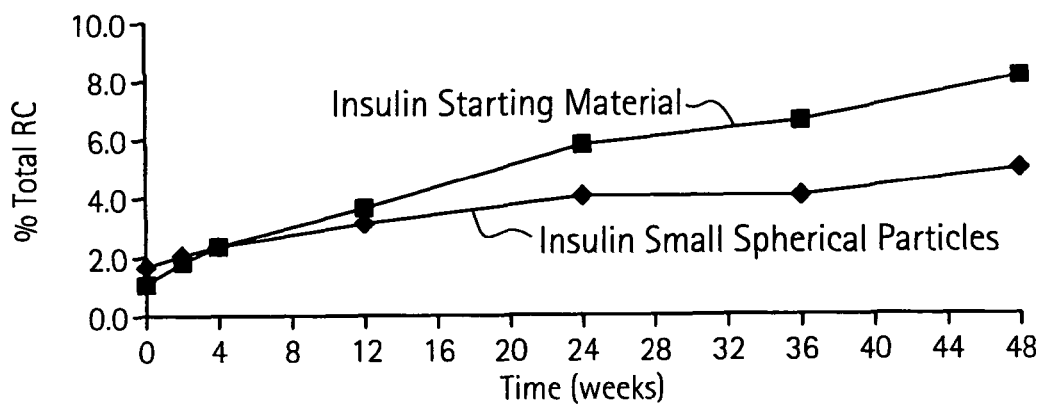
FIG. 35 is a chart of stability data of Insulin small spherical particles compared to Insulin starting material stored at 25° C.
Figure 36:
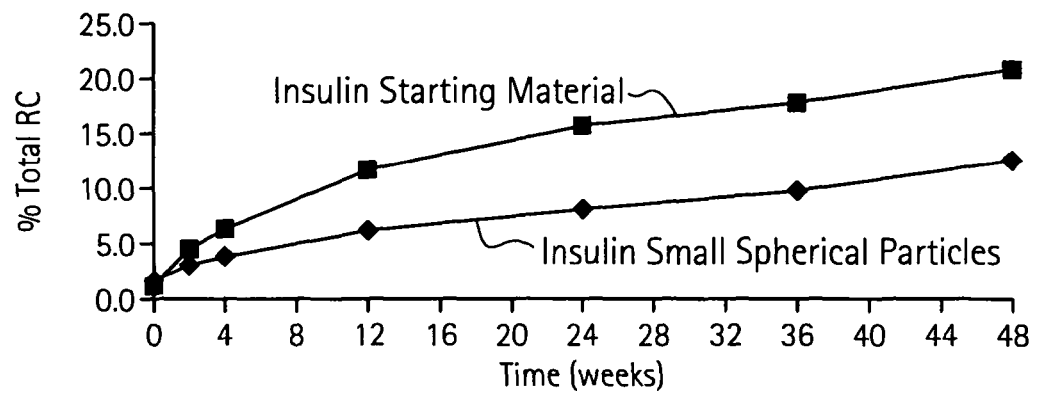
FIG. 36 is a chart of stability data of Insulin small spherical particles compared to Insulin starting material stored at 37° C.
Figure 37:
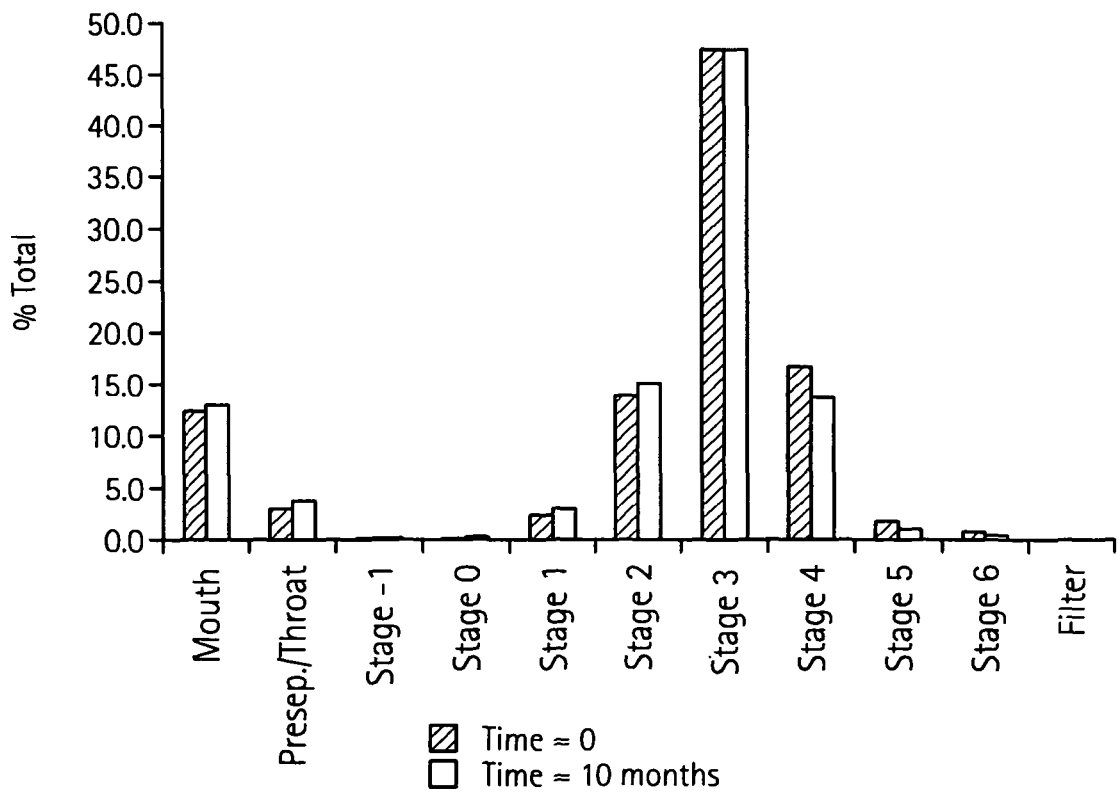
FIG. 37 is a bar graph of insulin aerodynamic stability using a Cyclohaler DPI.

FIGS. 31-36 show that at storage temperatures of 25° C. or 37° C., insulin in small spherical particles is significantly more stable to chemical degradation than the starting material without stabilizing excipients. In FIGS. 31 (25° C.) and 32 (37° C.), the percent insulin A21-desamido insulin formation of the starting material is significantly greater than the insulin in small spherical particles. In FIGS. 33 (25° C.) and 34 (37° C.), the percent insulin dimer and oligomer formation of the starting material is significantly greater than the insulin in small spherical particles. In FIGS. 35 (25° C.) and 36 (37° C.), the percent of insulin total related compounds of the starting material is significantly greater than the insulin in small spherical particles. FIG. 37 shows the aerodynamic stability of insulin small spherical particles using a Cyclohaler DPI in the Andersen Cascade Impactor device.

Example 14

The present invention can also be used to prepare small spherical particles of Alpha-1-Antitrypsin (AAT) which are particularly suitable for the preferred syringable delivery route of the invention. AAT has a molecular weight of about 44 kDa. This Example reports on jacketed column batch preparation of AAT small spherical particles (10-300 mg scale).

A solution buffered at pH 6.0 with 10 mM ammonium acetate containing 16% PEG 3350 and 0.02% Pluronic F-68 was mixed with a magnetic stirbar in a jacketed beaker and heated to 30° C. The beaker temperature was controlled using a circulating water bath. A concentrated solution of recombinant AAT (rAAT) was added to this solution while stirring and the pH was adjusted to 6.0. The rAAT concentration in the final solution was 2 mg/ml. The rAAT was completely soluble at this temperature in this solution composition. The entire contents of the vessel were transferred to a jacketed column and heated to 25-30° C. The circulating water bath for the column was set to ramp down to −5° C. The column and contents were cooled at approximately 1° C./minute to a temperature of about 4° C. The rAAT small spherical particles formed during the cooling step. The microsphere suspension was frozen in glass crystallizing dishes and lyophilized to remove the water and buffer.

In order to extract PEG from the protein small spherical particles after lyophilization, the PEG/protein cake was washed with methylene chloride ($MeCl_2$). Another washing media utilized was methylene chloride:acetone 1:1, or methylene chloride:pentane 1:1. The washing procedure was repeated for a total of 3 times the original volume washes. The final pellet was resuspended in a small volume of acetone or pentane and dried by either direct exposure to nitrogen gas or by rotary evaporation.

Example 15

In this example, AAT small spherical particles (200-2000 mg scale) were prepared using a jacketed vessel batch preparation. This type of preparation was done using the same formulation composition as the jacketed column but capable of accommodating larger volumes and was more suitable for scale-up. At this scale, the formulation was mixed at 75 rpm with an A-shaped paddle style impeller in a jacketed vessel, usually 500-1000 ml, and heated to 30° C. The vessel temperature was controlled using a circulating water bath. Keeping the solution in the same vessel, the water bath source was switched from a 30° C. bath to a 2° C. bath. The vessel and contents were cooled at approximately 1° C./minute to a temperature of 4° C. The rAAT small spherical particles formed during the cooling step. The temperature was monitored using a thermocouple, and when the suspension reached 4° C., it was held close to this temperature for an additional 30 minutes. After the hold step, the small spherical particle suspension was concentrated via diafiltration at around 4° C. to remove approximately 75% of the polymer and volume. The remaining small spherical particle suspension was frozen as a thin layer in a precooled lyophilization tray and lyophilized to remove the water and remaining buffer.

The protein small spherical particles were separated from the remaining dried polymer either by centrifugation with organic solvents (as described in Example 14) or by supercritical fluid (SCF) extraction. For SCF extraction, the dried material was transferred into a high pressure extraction chamber, which was pressurized to 2500 psi (at room temperature) with $CO_2$. Once operating pressure was reached, ethanol was introduced to the inlet fluid stream as a 70:30 $CO_2$:ethanol mix. This super critical fluid dissolved the polymer, leaving the small spherical particles. At the conclusion of the process, the system was flushed of ethanol and slowly decompressed.

Example 16

Small spherical particles were fabricated as described in Examples 14 and 15, and process yield was determined. After the cooling process was complete, a small aliquot of the suspension was removed and filtered through a 0.2 μm syringe filter to remove the solid small spherical particles. The absorbance of the filtrate, which was the rAAT remaining in solution, was determined at 280 nm using a UV spectrophotometer. The rAAT concentration was then calculated from a standard curve. The % conversion was calculated as:

$$\frac{(\text{Starting rAAT concentration} - \text{filtrate rAAT concentration})}{\text{Starting rAAT concentration}} * 100\% = \% \text{ conversion}$$

| Scale | % conversion to small spherical particles |
|---|---|
| 100–200 mg (n = 9, column) | 91.7 ± 4.4 |
| 300 mg (n = 4, column) | 93.4 ± 1.6 |
| 2 g (n = 5, vessel) | 90.4 ± 1.8 |

As shown in the above table, a high percentage of the AAT protein was converted into small spherical particles irrespective of the process scale.

Example 17

This Example shows particle size distribution of AAT particles at different process scales Aerosizer data. A sample of the final AAT dry powder small spherical particles was analyzed in a TSI AEROSIZER® 3225, which measures particle size by time of flight measurements. From these measurements, different ratios of volume diameters were calculated to demonstrate the particle size distribution of the AAT small spherical particles and were used to compare to particles fabricated by methods other than that of the present invention.

| Scale | d90/d10 (volume) | d80/d20 (volume) | (d90 − d10)/d50 (volume) |
|---|---|---|---|
| 5-10 mg (n = 12, column) | 1.88 ± 0.20 | 1.49 ± 0.10 | 0.67 ± 0.14 |
| 100-200 mg (n = 5, column) | 1.83 ± 0.05 | 1.41 ± 0.05 | 0.66 ± 0.05 |
| 300 mg (n = 3, column) | 2.05 ± 0.17 | 1.61 ± 0.11 | 0.77 ± 0.06 |
| 1-2 g (n = 4, vessel) | 2.21 ± 0.30 | 1.60 ± 0.11 | 0.86 ± 0.19 |

A 5-10 mg sample was weighed into a gel capsule and administered into the Andersen Cascade Impactor using the Cyclohaler Dry Powder Inhaler at a flow rate of 60 liters per minute (LPM). Small spherical particles were collected from all impact or stages, dissolved in 0.2M Tris-HCl buffer at pH 8.0, and quantitated using reverse phase HPLC. The data were analyzed and the geometric standard deviation (GSD) calculated as described in the United States Pharmacopeia (USP). The data demonstrated the narrow size distribution.

| Scale | GSD |
| --- | --- |
| 100-200 mg (n = 5, column) | 1.74 ± 0.22 |
| 300 mg (n = 3, column) | 1.77 ± 0.40 |
| 2 g (n = 5, vessel) | 1.70 ± 0.09 |

All of the distribution parameters shown above demonstrated the excellent particle size distribution that results from the fabrication method of the present invention.

Example 18

This Example illustrates retention of AAT bioactivity. To determine the specific activity, the rAAT small spherical particles were dissolved in 0.2M Tris-HCl pH 8.0 at room temperature. The resulting solution was analyzed by an assay which measures the capacity of rAAT to inhibit the ability of porcine pancreatic elastase (PPE) to hydrolyze synthetic peptides that contain a p-nitroanilide group at their C-terminus. The same solution of rAAT small spherical particles was then assayed for protein concentration using the Bicinchoninic Acid (BCA) assay. A control rAAT starting material solution was also analyzed in both assays. Because the activity assay was developed to determine the activity based on a concentration of 1 mg/ml protein per sample, the activity value was corrected based on the actual protein concentration as determined by BCA, giving the specific activity value:

$$\frac{\text{activity value for sample}}{\text{actual protein concentration}} = \text{specific activity for sample}$$

Inhibition of porcine pancreatic elastase by rAAT

| Scale | IU/mg small spherical particles | IU/mg control |
| --- | --- | --- |
| 100-300 mg (n = 12, column) | 64.19 ± 5.01 | 64.34 ± 4.95 |
| 200-300 mg (n = 8, vessel) | 62.53 ± 5.29 | 65.87 ± 0.98 |

The specific activity thus demonstrated the retention of bioactivity after fabrication of AAT into small spherical particles.

Example 19

This Example describes preparation of humanized monoclonal antibody microspheres with PEG or Poloxamer as solvent and microsphere formation under cooling. A 1 mL solution of 4 mg/mL humanized monoclonal antibody (anti-CD25 monoclonal antibody) in 40 mM ammonium acetate buffer at pH=5.9 was mixed with 1 mL of 30% (w/v) solution of PEG 3350 Da, available from Spectrum Chemicals (Gardena, Calif.) in water. Alternately, the solution was mixed with 1 mL of 30% (w/v) solution of poloxamer 188 NF (Lutrol F68), available from BASF Corporation (Florham Park, N.J.), in water. The mixtures were incubated in a water bath for 10 minutes at 35° C. and then were cooled to 2° C. at a rate of approximately 0.7 degrees Celsius per minute.

The samples were then viewed in the light microscope at 10× and 100× magnification, and showed formation of spherical particles using either polymer. Most of the microspheres appeared to be about 2 microns in diameter, but some were smaller. Few microspheres were larger than 5 microns in diameter.

Example 20

This Example illustrates retention of AAT structural integrity. One of the central differentiating points of controlled phase separation (CPS) technology is the formation of particles under mild conditions utilizing aqueous systems during particle formation and avoiding other stress-inducing conditions such as increased temperature, shear, etc. In the particle engineering field, major concerns are the stability of proteins during the fabrication and the storage stability. The main degradation pathways such as oxidation, deamidation and especially aggregation of proteins are believed to be responsible for protein formulation side effects including immunogenicity. Therefore, regulatory concerns require an extremely low level of degradation products in final particle formulations. HPLC, physical chemical characterization such as CD and DSC were utilized to determine whether protein modification occurred during formation.

Circular Dichroism (CD) is the most commonly used method for evaluation of structural changes in a protein subjected to perturbation, or comparison of the structure of an engineered protein to the parent protein. The CD method is assessing protein folding, and protein secondary and tertiary structure.

Secondary structure can be determined by CD spectroscopy in the "far-UV" spectral region (190-250 nm). At these wavelengths, the chromophore is the peptide bond when it is located in a regular, folded environment. Alpha-helix, beta-sheet, and random coil structures each give rise to a characteristic shape and magnitude of CD spectrum. The approximate fraction of each secondary structure type that is present in any protein can thus be determined by analyzing its far-UV CD spectrum as a sum of fractional multiples of such reference spectra for each structural type.

The CD spectrum of a protein in the "near-UV" spectral region (250-350 nm) can be sensitive to certain aspects of tertiary structure. At these wavelengths the chromophores are the aromatic amino acids and disulfide bonds, and the CD signals they produce are sensitive to the overall tertiary structure of the protein. Signals in the region from 250-270 nm are attributable to phenylalanine residues, signals from 270-290 nm are attributable to tyrosine, and those from 280-300 nm are attributable to tryptophan. Disulfide bonds give rise to broad weak signals throughout the near-UV spectrum.

Figure 17A:
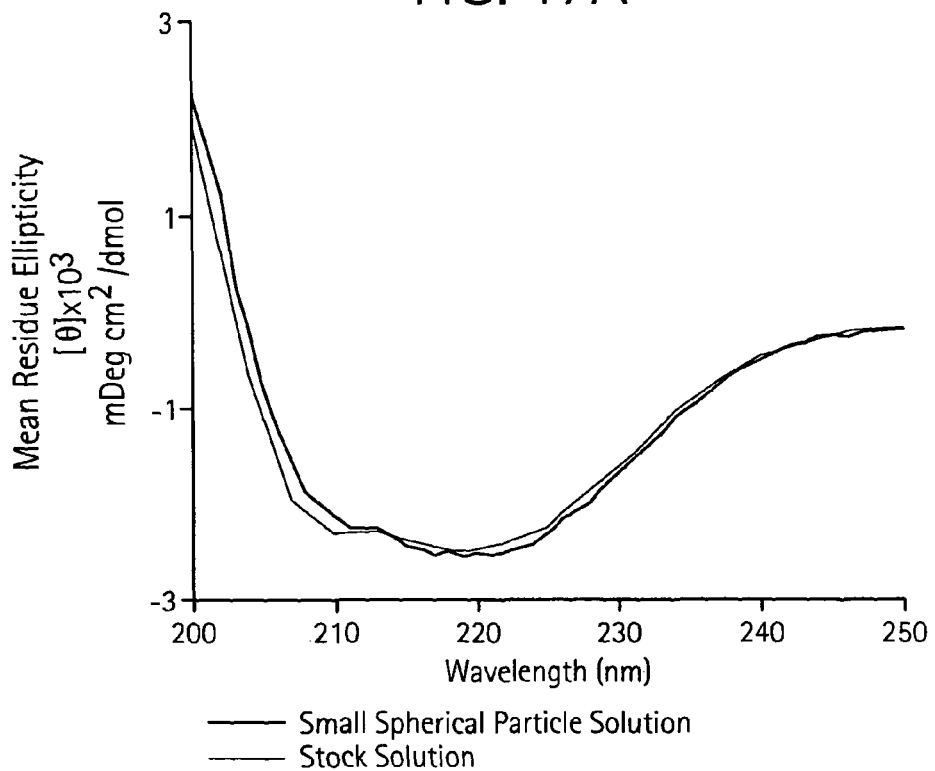
FIG. 17a is a circular dichroism (CD) plot for alpha-1-antitrypsin (AAT).

Far-UV CD spectra of the rAAT stock solution and AAT released from small spherical particles in phosphate buffer (pH 7.4, T=25° C., protein concentration 0.05 mg/mL) are shown in FIG. 17a. Each spectrum represents the average of 10 scans.

The far-UV CD spectra are indistinguishable, demonstrating that fabrication of AAT into small spherical particles upon its subsequent release resulted in AAT molecules with a structure identical to that of the starting AAT material.

Small spherical particles were dissolved in 0.2M Tris-HCl at pH 8.0 and analyzed by reverse-phase HPLC. When compared to a control solution of starting rAAT protein, there is no apparent difference in the appearance of the chromatograms.

Figure 17B:
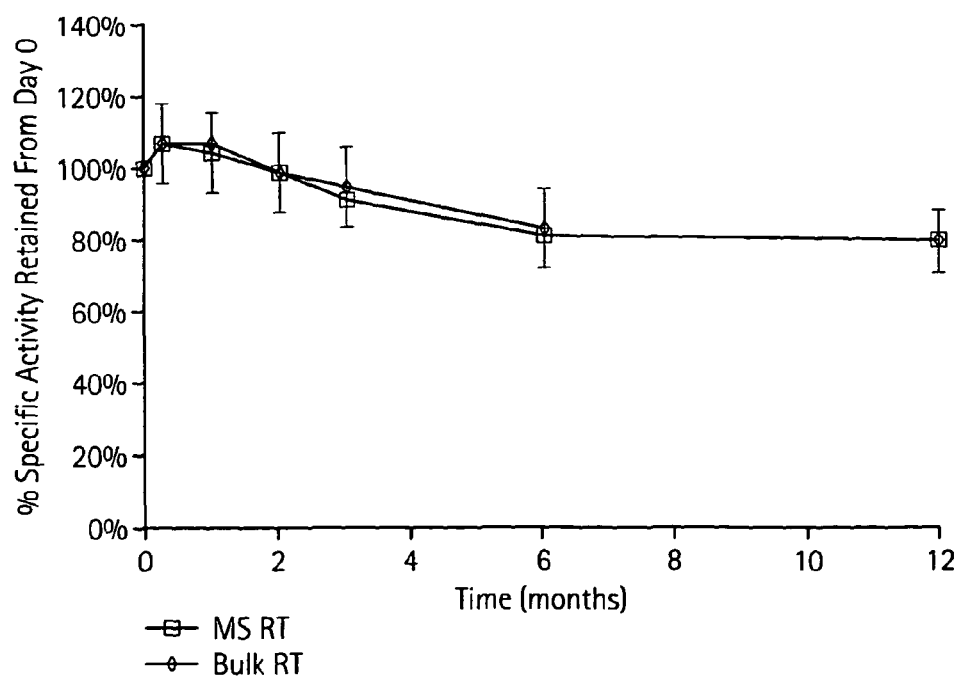
FIG. 17b is a plot of activity against storage time at room temperature in Example 21.
Figure 17C:
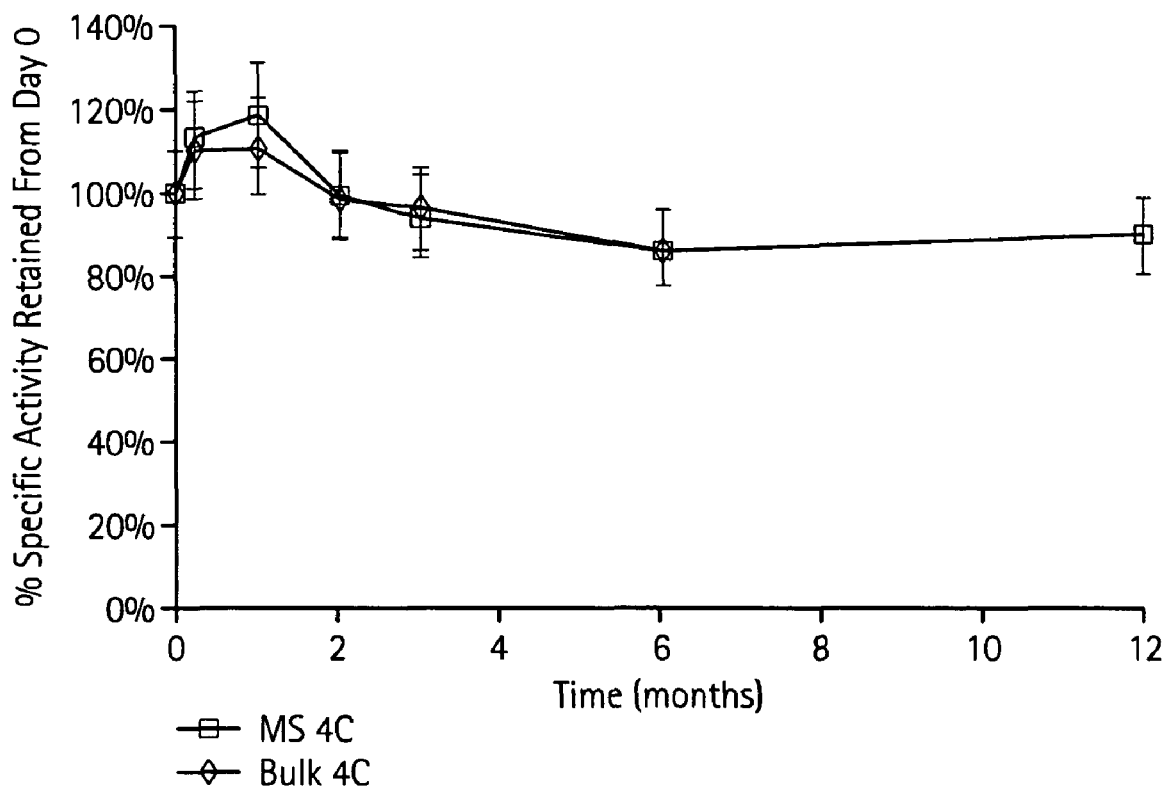
FIG. 17c is a plot of activity against storage time at 4° C. in Example 21.
Figure 18:
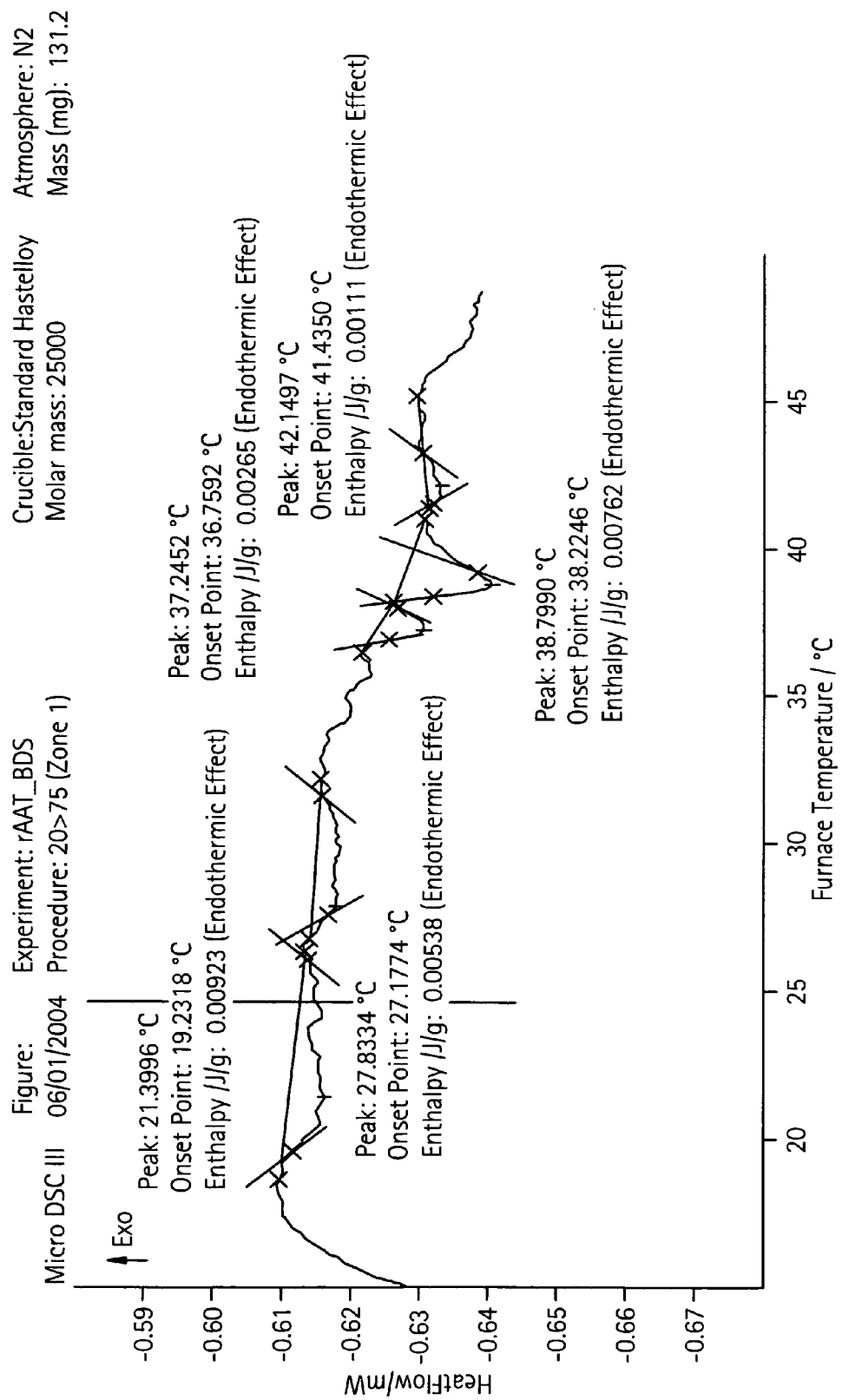
FIGS. 18-28b are DSC plots.
Figure 19:
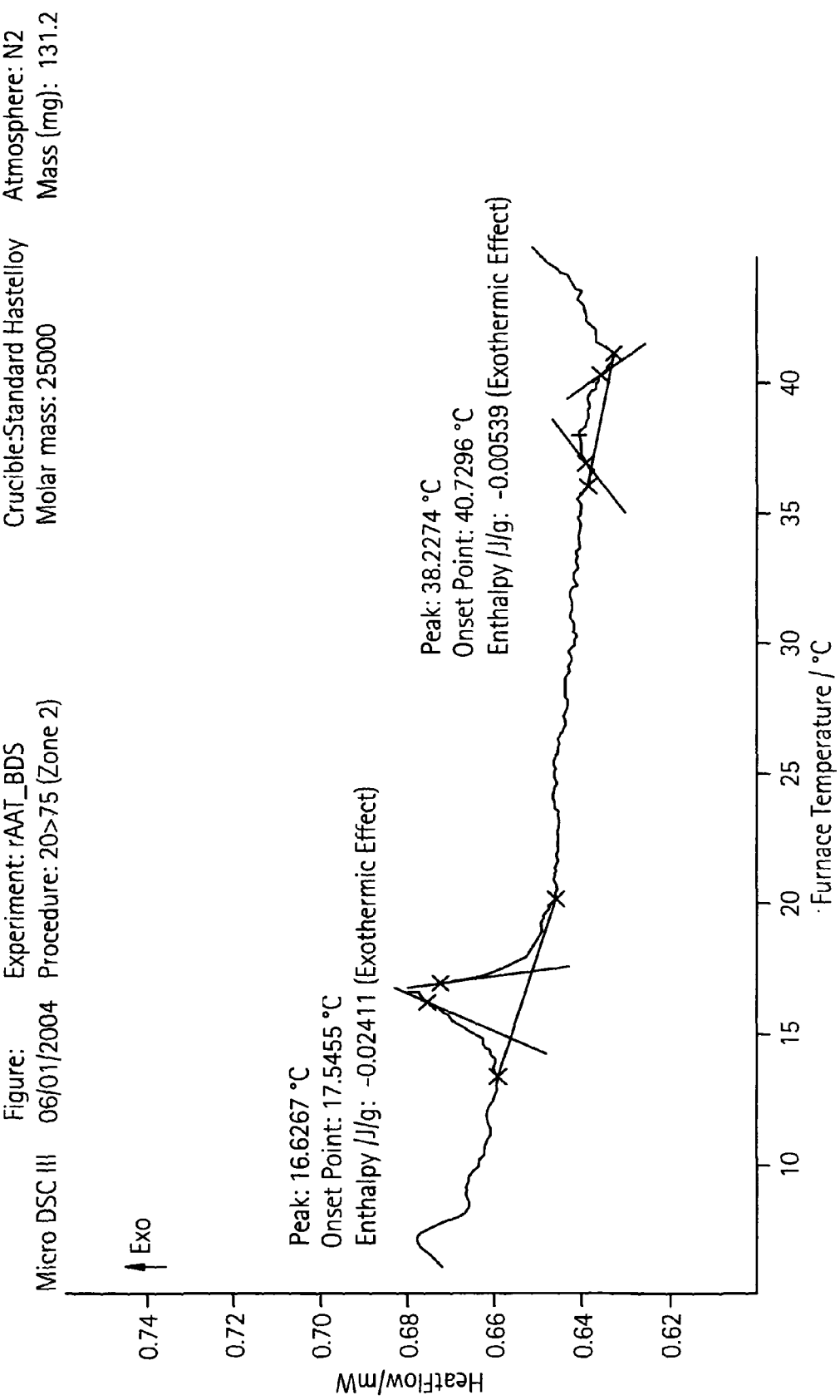
Figure 20:
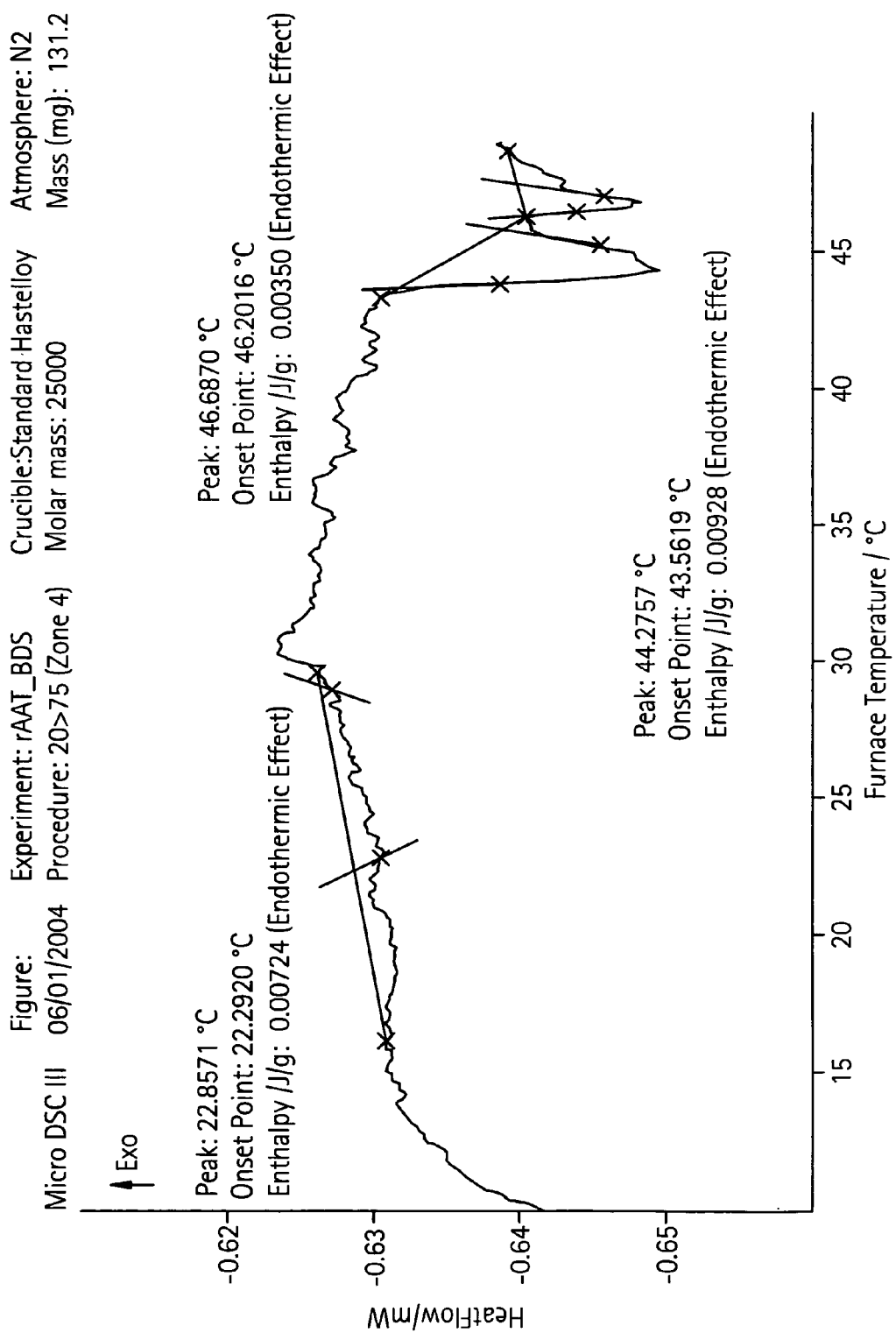
Figure 21:
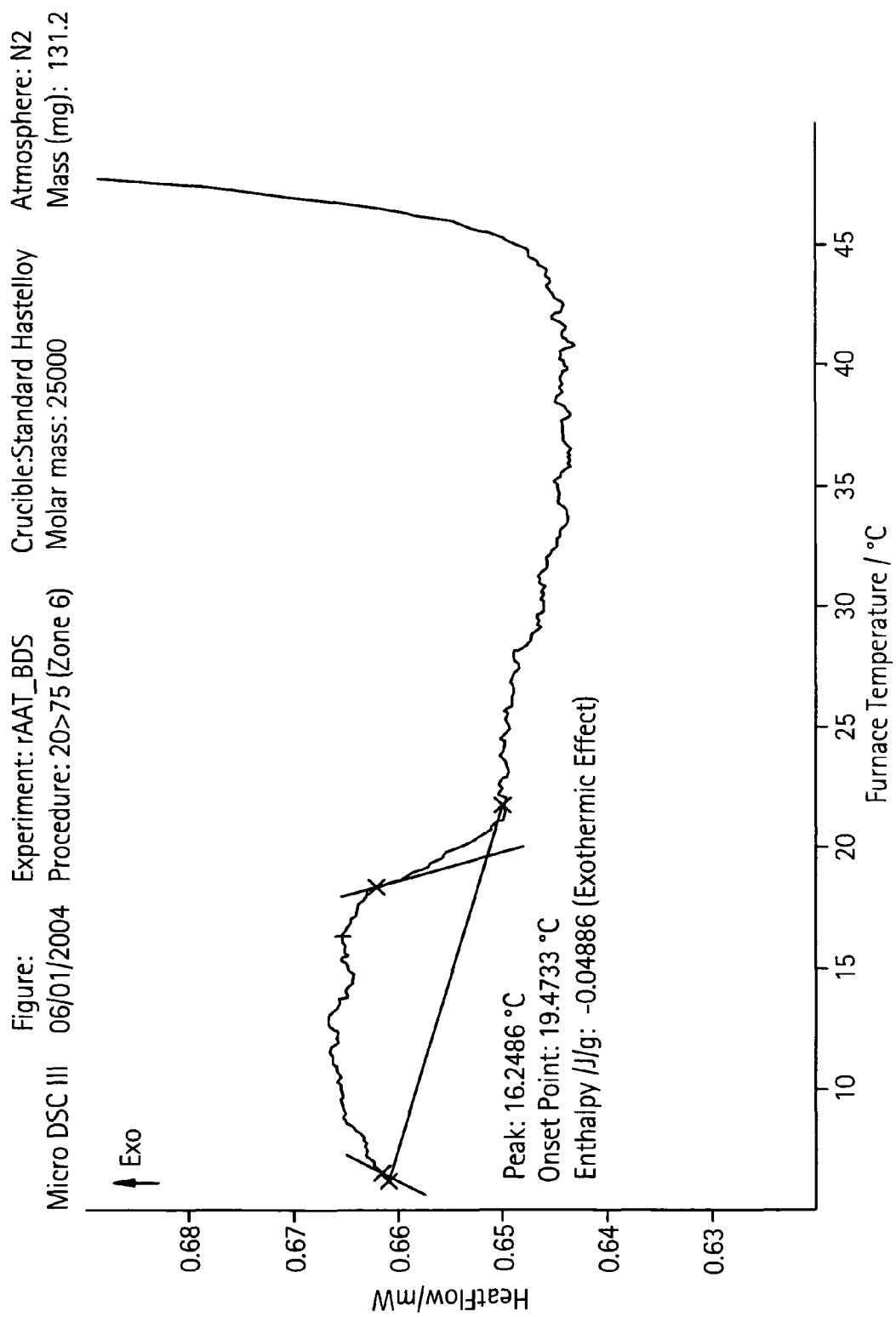
Figure 22:
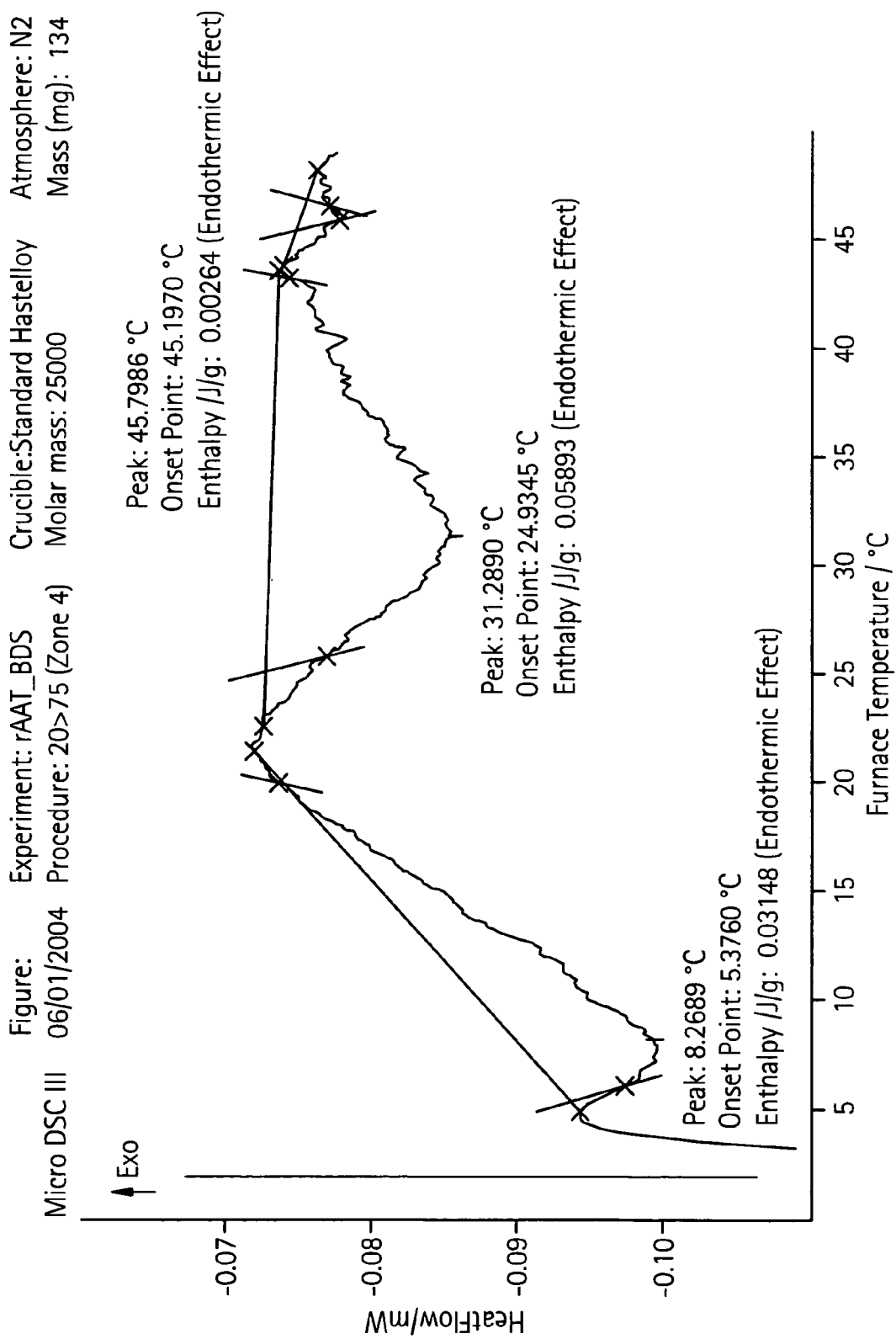
Figure 23:
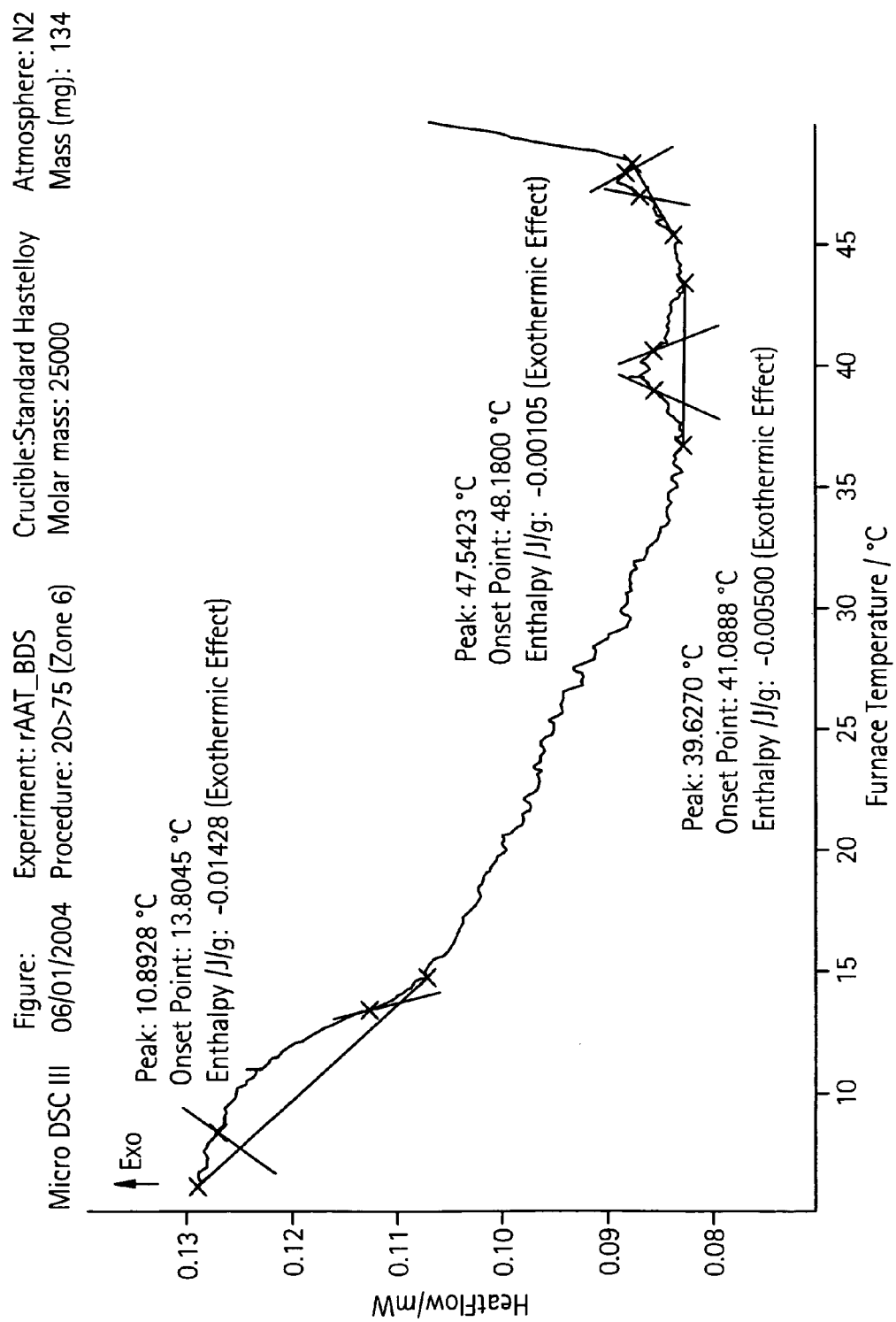
Figure 24:
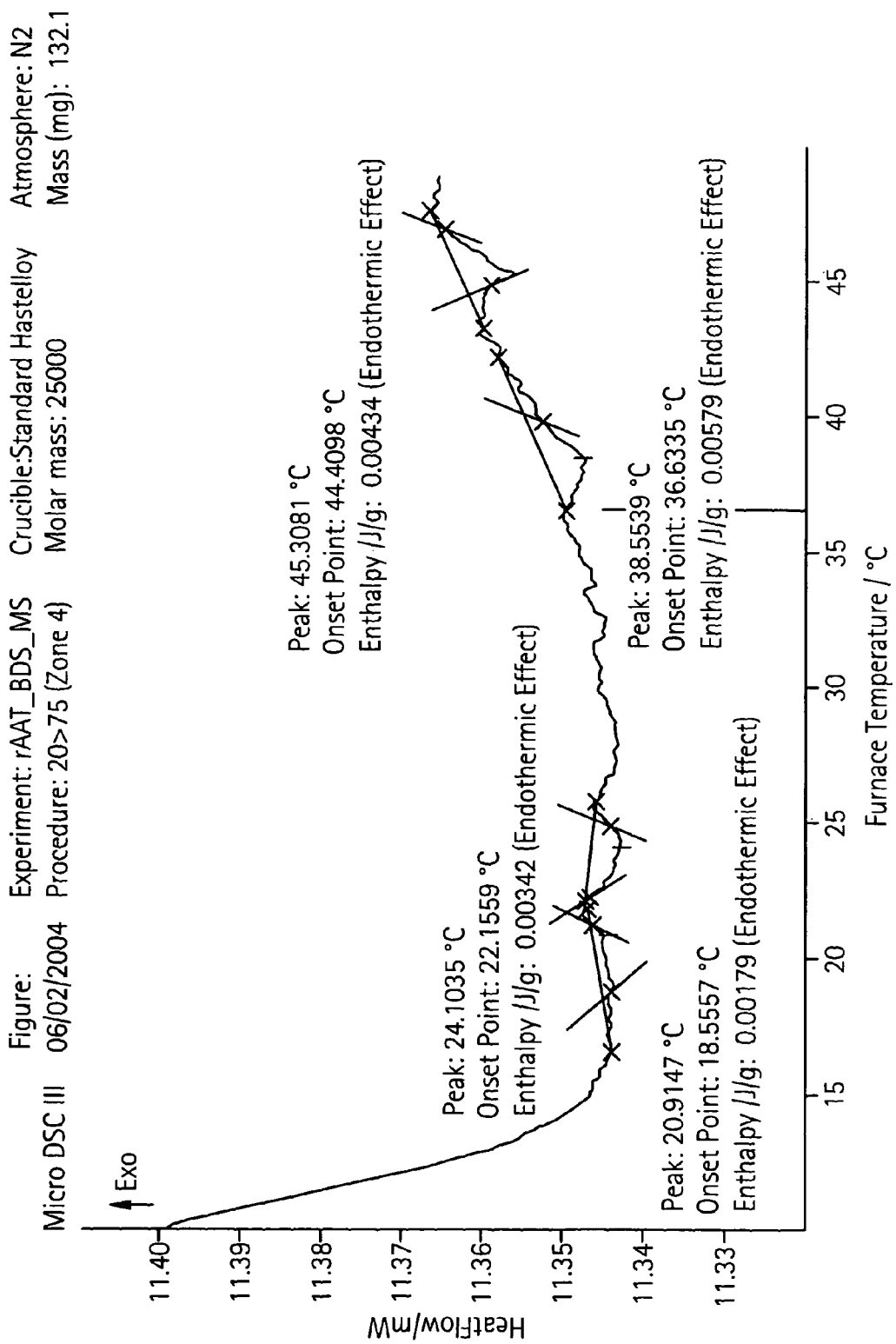
Figure 25:
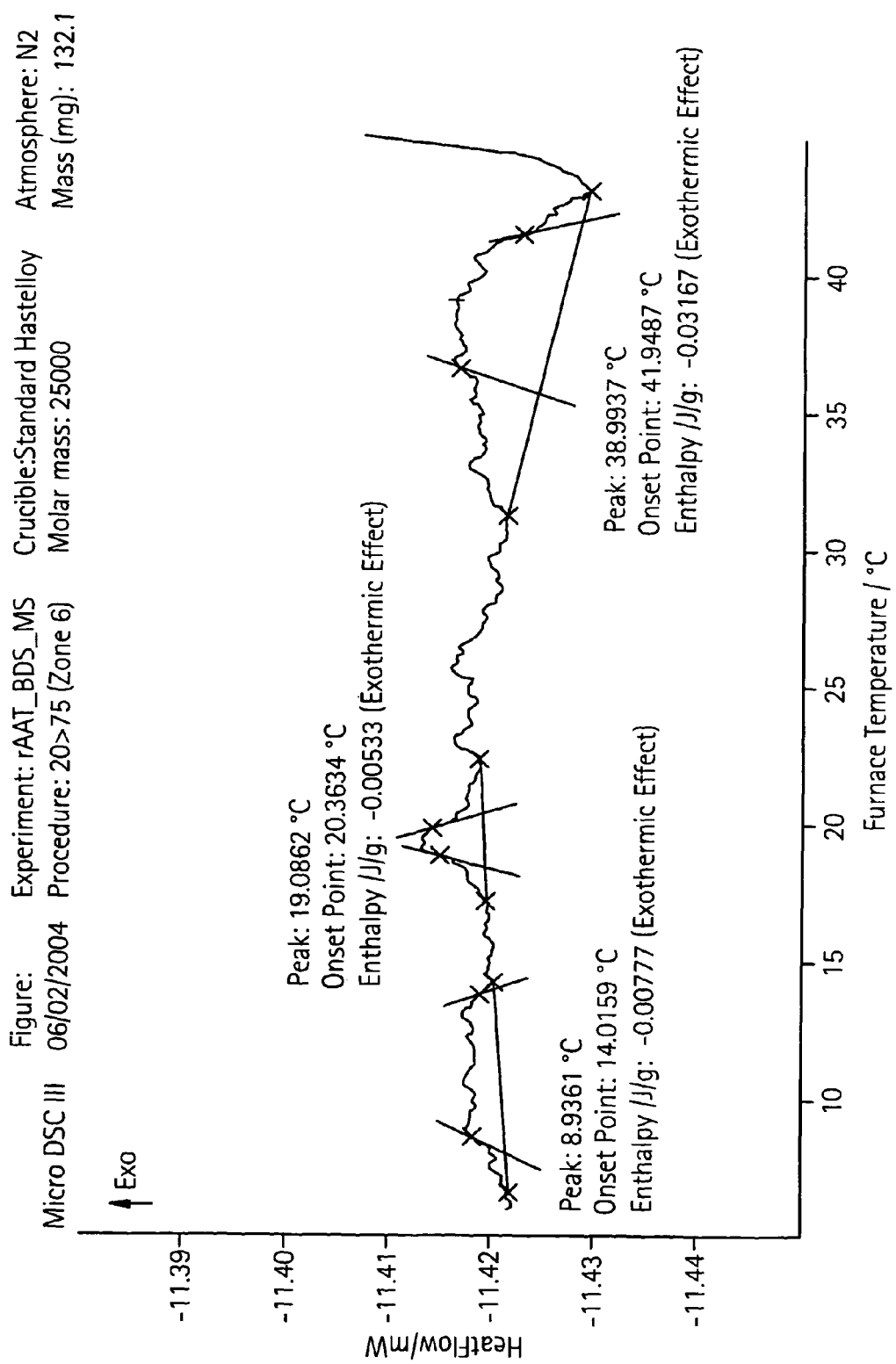
Figure 26:
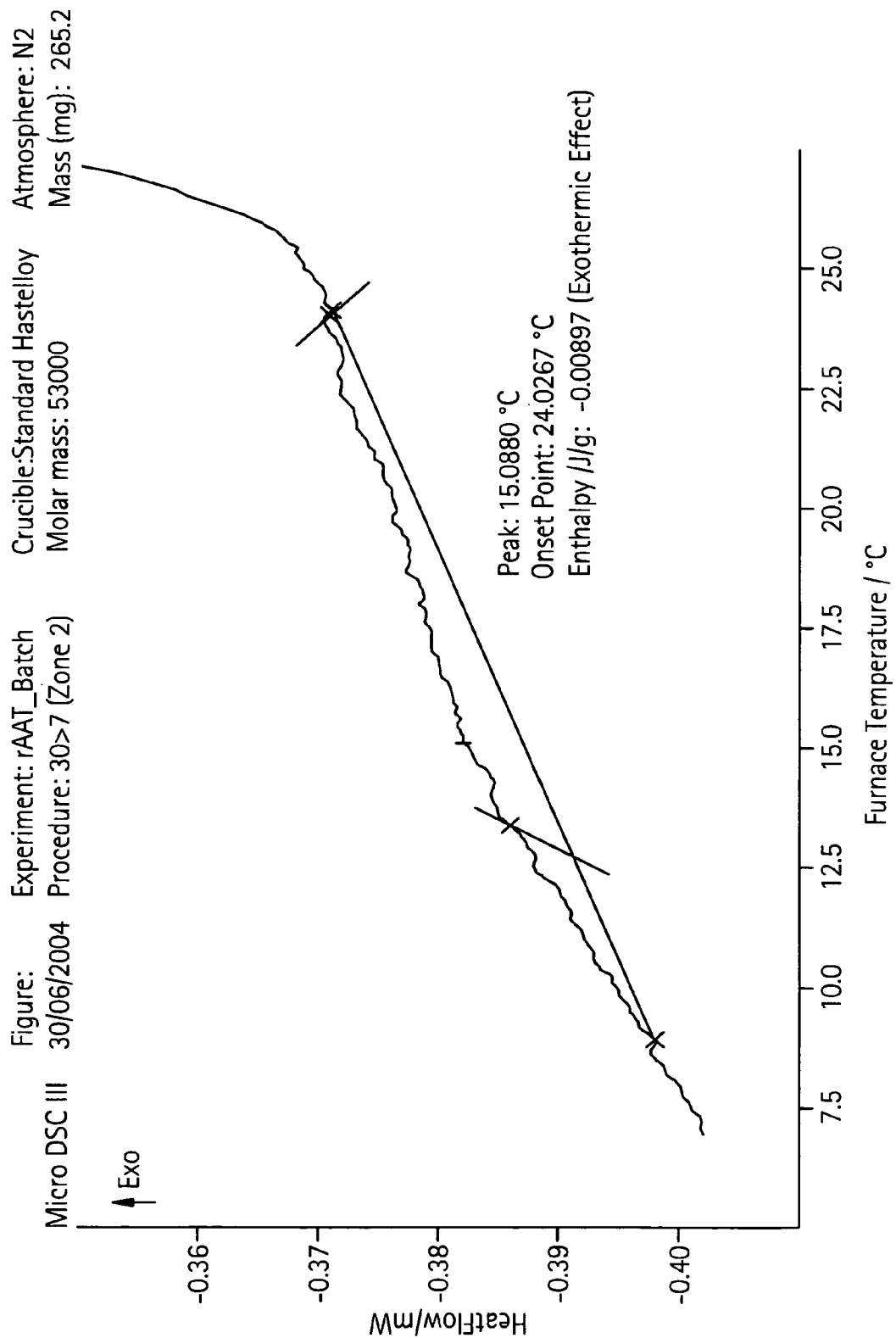
Figure 27:
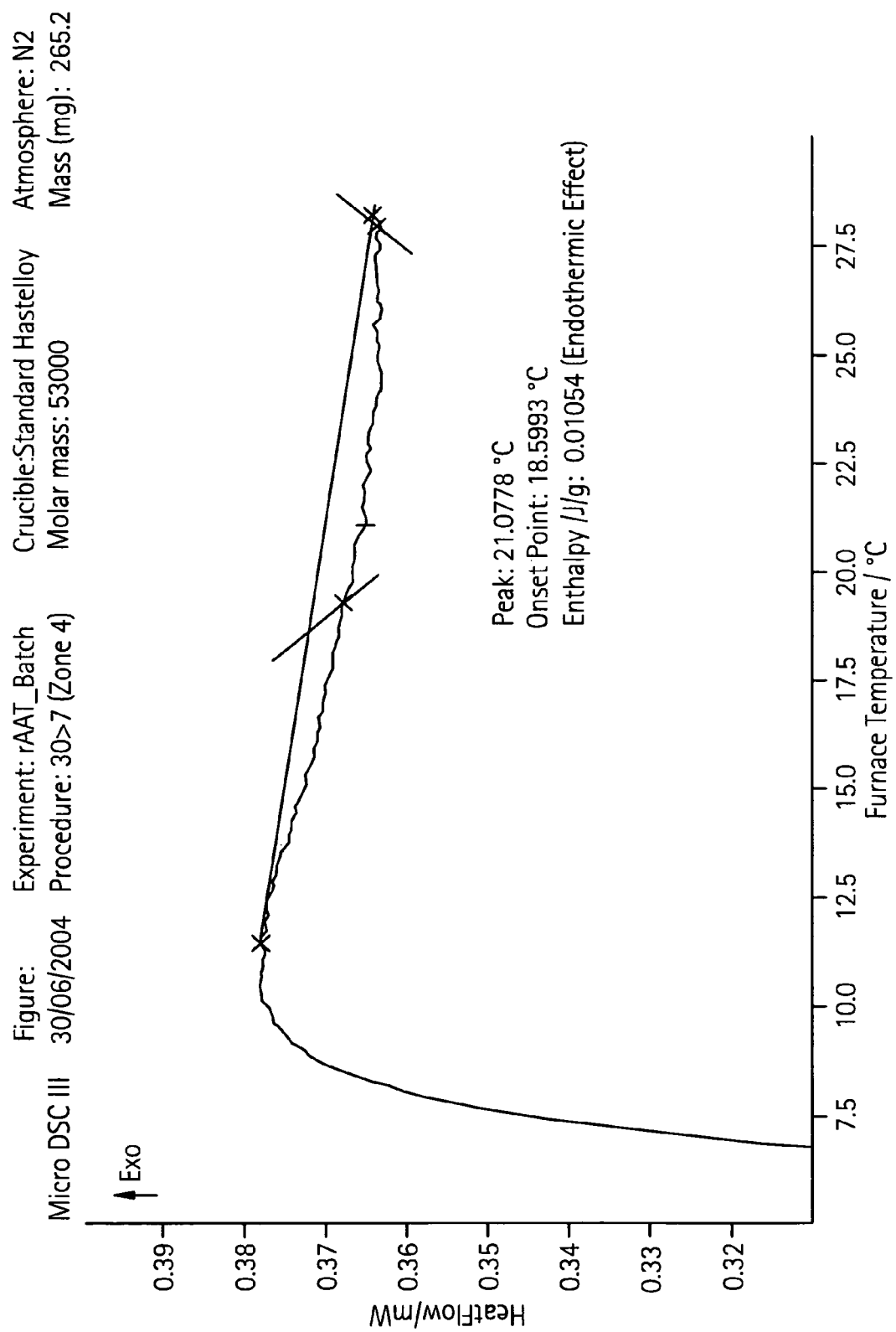
Figure 28A:
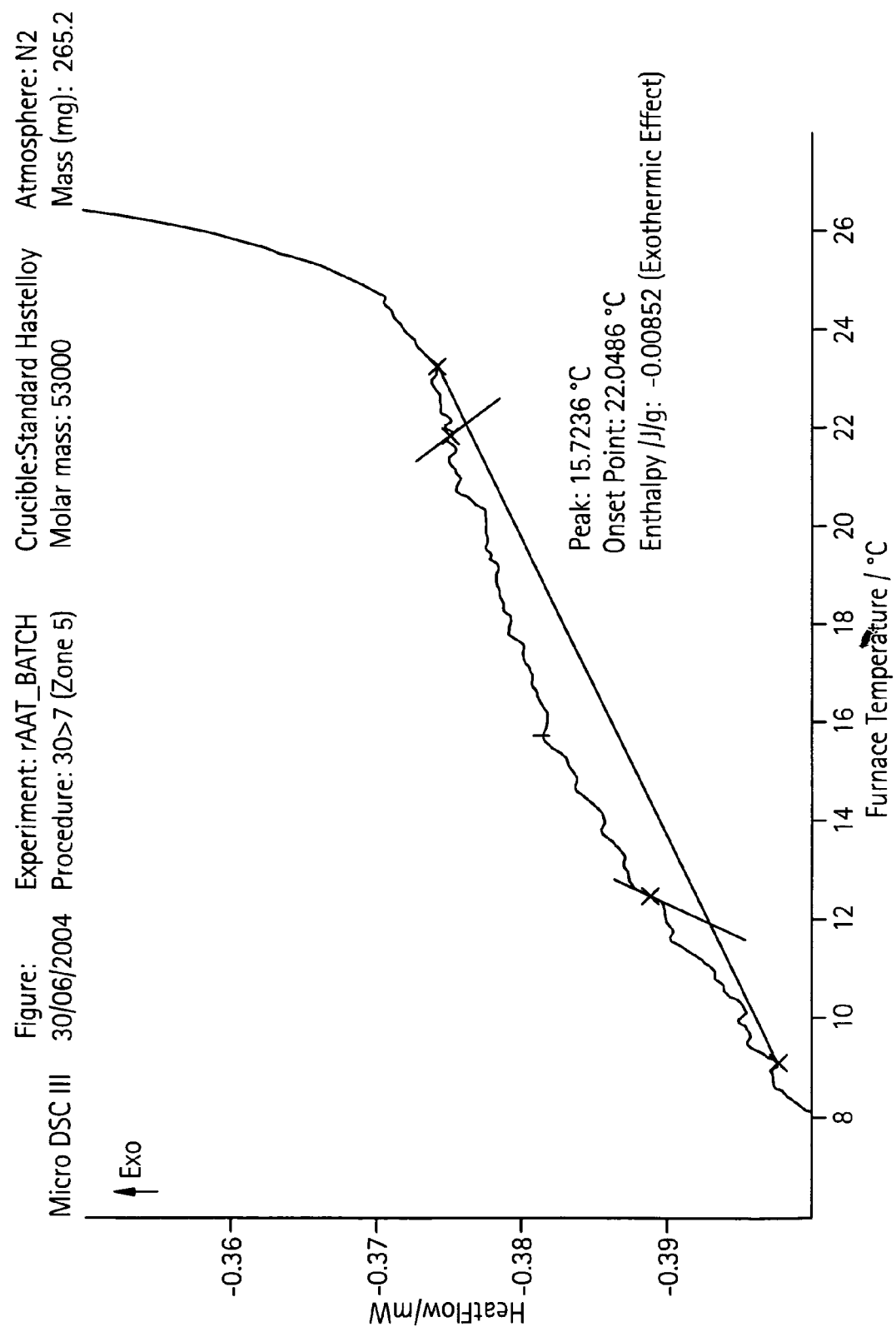
Figure 28B:
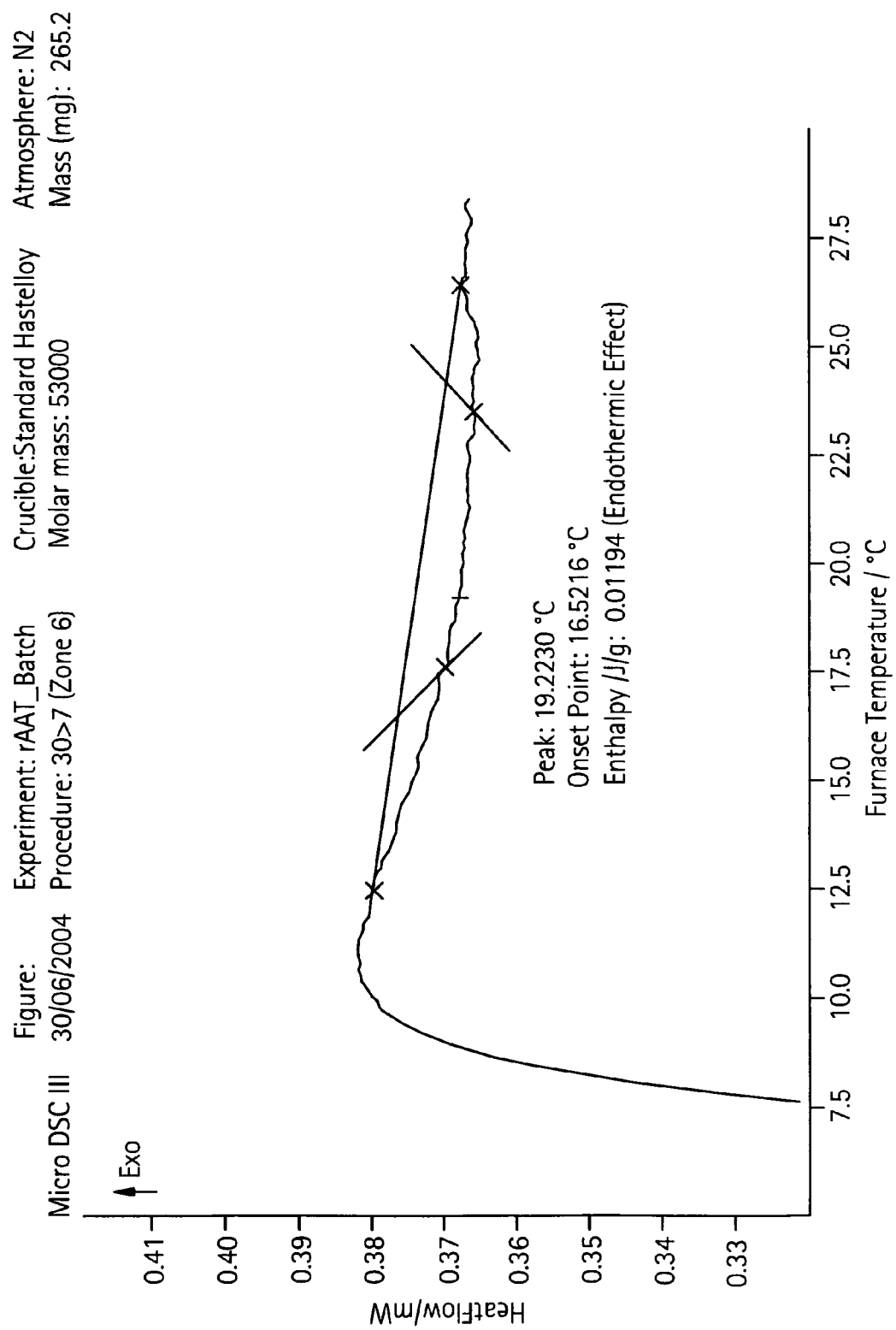

HPLC system:
HPLC Column—Pheomenex Jupiter, 5 micron, C4, 300A, 250×4.6 mm
Waters Alliance 2965 Pump/autosampler
Wavelength—280 nm
Injection Volume—75 ul
Gradient of concentration:
   Mobile phase 1: 0.1% TFA in water
   Mobile phase 2: 0.085% TFA in 90% (c/v) acetonitrile in water
Run time—60 min
Flow rate—1.0 ml/min DSC (differential scanning calorimetry) plots were generated. See [FIGS. 15-25b] FIGS. 18-28b. FIG. 18 is a first heating thermogram and FIG. 19 is a first cooling thermogram of a 50 mg/ml rAAT sample in BDS solution versus BDS. FIG. 20 is a first heating thermogram and FIG. 21 is a first cooling thermogram of a 50 mg/ml rAAT sample in BDS solution versus BDS. FIG. 22 is a second heating thermogram and FIG. 23 is a second cooling thermogram of a 45 mg/ml rAAT sample in acetate solution versus acetate buffer as a reference. FIG. 24 is a second heating thermogram and FIG. 25 is a second cooling thermogram of a 1 mg/ml rAAT sample in BDS solution versus BDS. The rAAT sample resulted from dissolving rAAT 3 small spherical particles in BDS. FIG. 26 is a first cooling thermogram and FIG. 27 is a first heating thermogram of the small spherical particle fabrication batch. FIG. 28a is a first cooling thermogram and FIG. 28b is a first heating thermogram of the small spherical particle fabrication batch.

Example 21

This Example reports storage stability of AAT small spherical particles relative to that of AAT starting material. Small spherical particles were analyzed for retention of bioactivity (using the assay described in Example 18) after storage at room temperature and 4° C. for 1 week, 1 month, 2 months, 3 months, 6 months, and 12 months. (FIGS. 17b and 17c.) The bulk material is rAAT starting solution which has been dialyzed and then lyophilized. For each time point and storage condition, there were duplicate samples which were each assayed in duplicate.

Example 22

Dnase small spherical particles were prepared. DNase has a molecular weight of approximately 38 kDa. Formulation example: A solution of: 0.18 mg/ml DNase (from stock 1 mg/ml), 18.2% PEG 3350 (from stock 25%), 9 mM ammonium acetate, pH 5.15 (from stock 1M). This suspension was cooled in the −80° C. freezer and, once frozen, was lyophilized on a manifold lyophilizer, and subsequently washed by centrifugation with MeCl$_2$/acetone.

Figure 38:
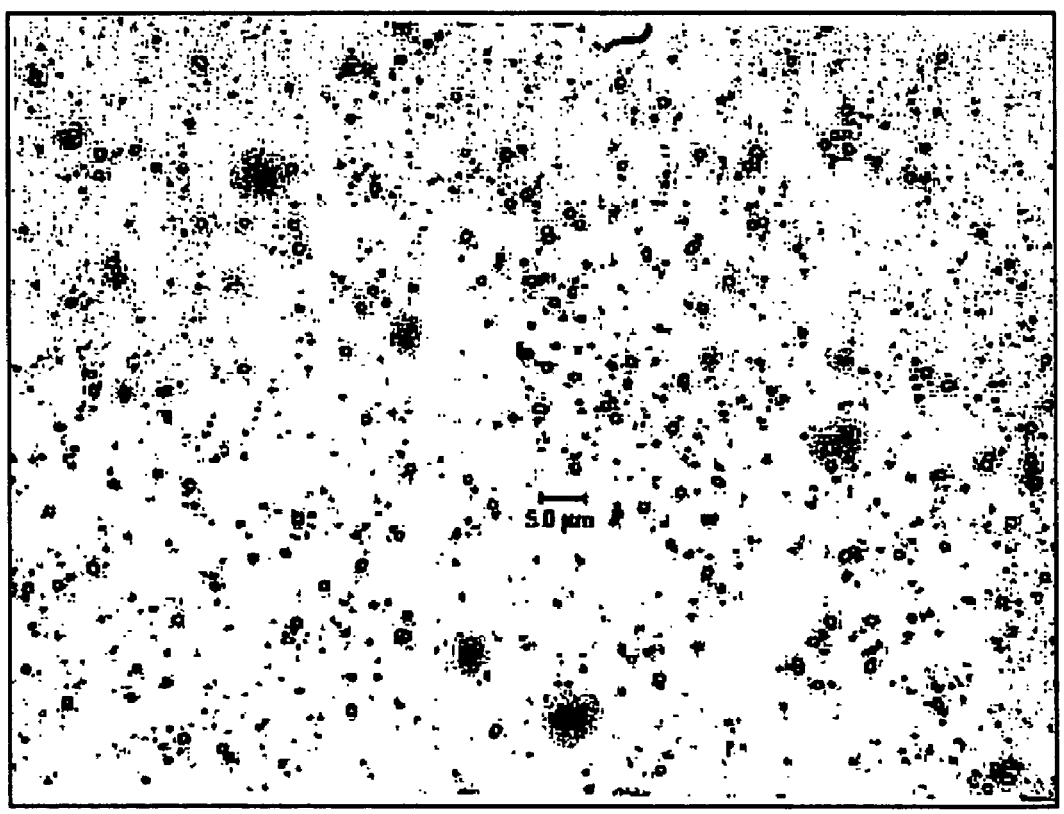
FIG. 38 is a light micrograph of [Danes] DNase small spherical particles.
Figure 39:
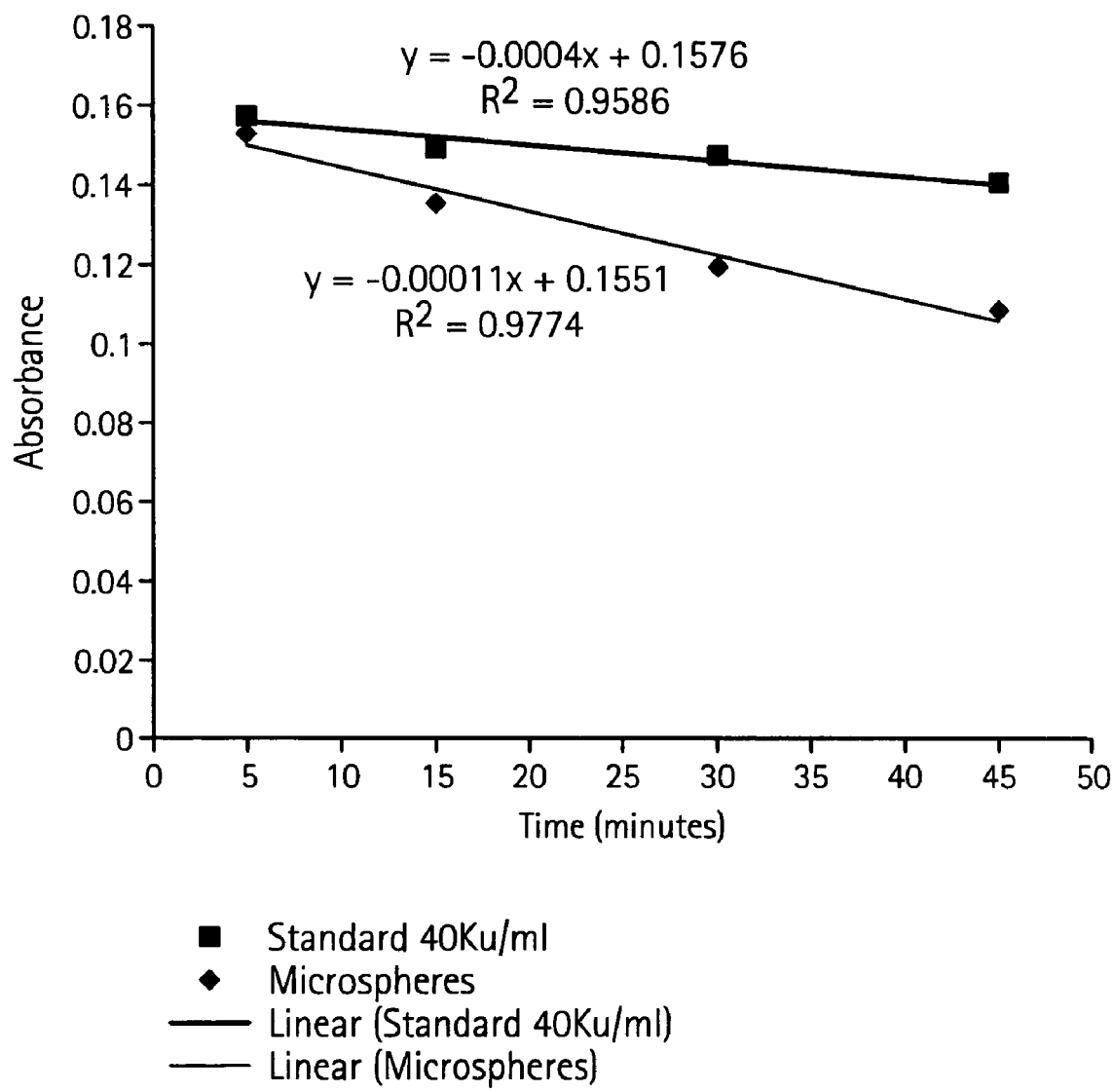
FIG. 39 is a chart of enzymatic activity of DNase.

Initial concentrations tried were 0.1 mg/ml DNase and 20% PEG 3350. But after trying to cool from 37° C. to 0° C. and not getting a precipitate, another amount of DNase was added to get the above concentrations. This solution was cooled in the −80° C. freezer and, once frozen, was lyophilized on the manifold lyophilizer and washed by centrifugation with MeCl$_2$/acetone. Initial concentrations tried were 0.1 mg/ml DNase and 20% PEG 3350. But after trying to cool from 37° C. to 0° C. and not getting a precipitate, another amount of DNase was added to get the above concentrations. This solution was cooled in the −80° C. freezer and, once frozen, was lyophilized on the manifold lyophilizer and washed by centrifugation with MeCl$_2$/acetone. FIG. 38 is a light micrograph of microspheres of DNaseI. FIG. 39 is a chart of enzymatic activity for DNase in microspheres and a standard reference solution. The chart shows the disappearance of methyl green at 640 nm.

Activity (Assay for DNase-I using DNA-Methyl Green, purchased from Sigma). The theoretical activity for the starting material is listed as 775 Ku/mg protein. The stock solution was determined to be 0.145 mg/ml protein. This concentration was diluted into 5 ml for a final concentration of 0.0199 mg/ml. The activity should be 775 Ku/mg*0.0199 mg/ml=15.46 Ku/ml.

$$\text{Kunitz units/ml of solution} = \frac{\Delta A640 \text{ per min of unknown} \times 40 \times \text{dilution factor}}{\Delta A640 \text{ per min of known}}$$

$$\text{Ku/ml} = -0.0004 \times 40 \times 1 / -0.011 = 14.55 \text{ Ku/ml}$$

Compare to theoretical: Small Spherical Particles/theoretical*100%=% activity:

$$14.55 \text{ Ku/ml}/15.46 \text{ Ku/ml}*100\%=94.1\%$$

Example 23

Figure 40:
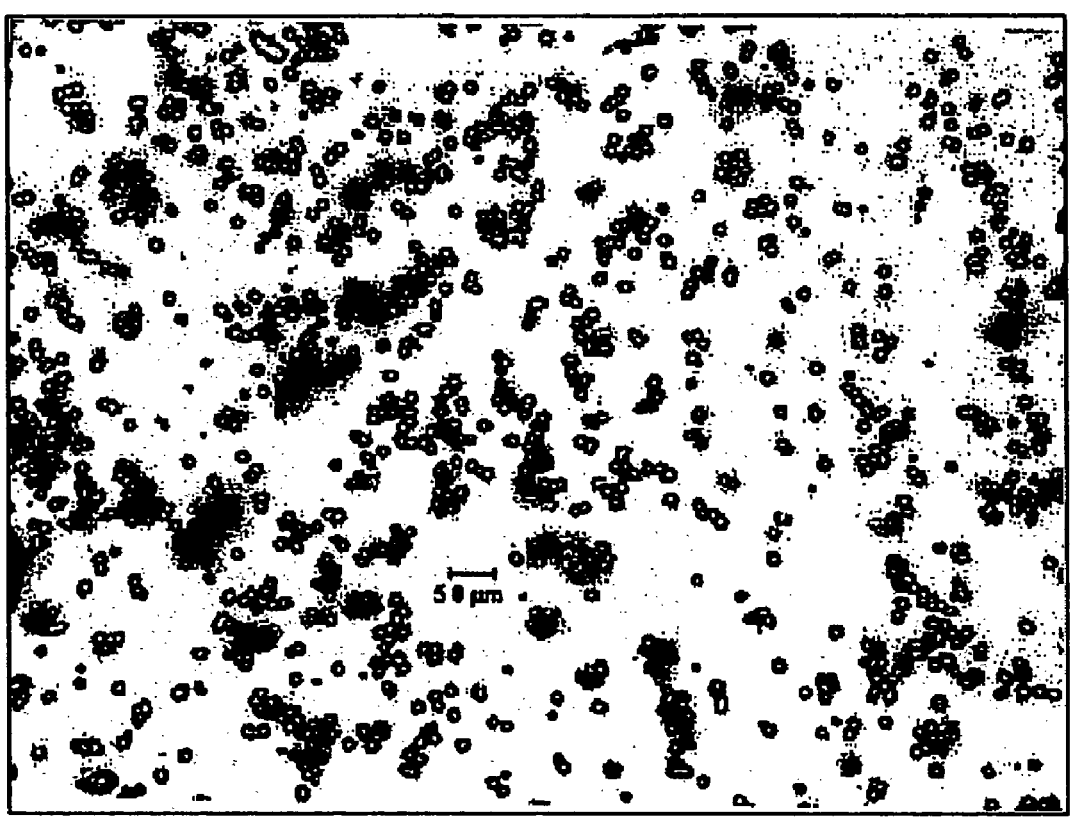
FIG. 40 is a light micrograph of SOD small spherical particles.
Figure 41:
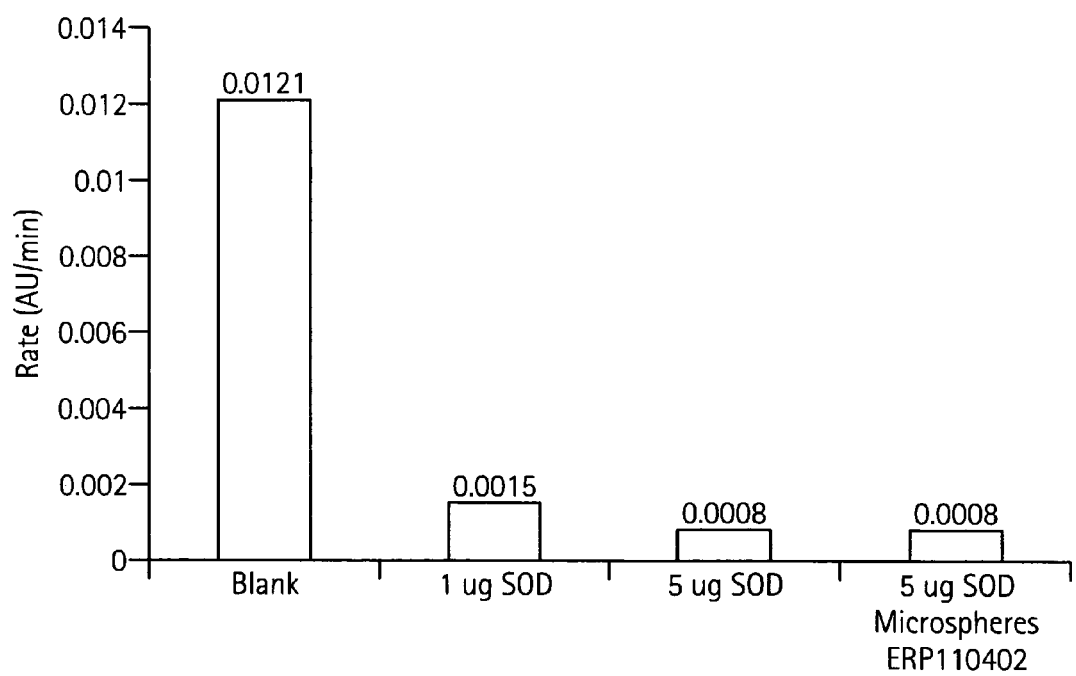
FIG. 41 is a chart of enzymatic data for SOD small spherical particles.

Superoxide dismutase (molecular weight of about 32 kDa) small spherical particles are prepared. A solution of 0.68 mg/ml SOD (from stock 5 mg/ml), 24.15% PEG 3350 (from stock 31.25%), 9.1 mM ammonium acetate (from stock 1M), Final pH=4.99, adjusted with ammonium hydroxide and acetic acid. The solution was cooled from 40° C. to 0° C. over 50 minutes (~0.8° C./min) and precipitation initiated around 25° C. The suspension was flash frozen in liquid nitrogen, and lyophilized on manifold lyophilizer, and subsequently washed by centrifugation with MeCl$_2$/acetone. Small spherical particles were formed and the majority of acetone was retained. FIG. 40 shows a light micrograph of SOD small spherical particles. FIG. 41 shows the chart of enzymatic activity of SOD where the activity of SOD is measured by inhibition of nitro blue tetrazolium reduction.

Example 24

Subtilisin (molecular weight of about 35, 230 Daltons) small spherical particles are prepared using non-polymer phase-separation enhancing agents. The continuous phase of the initial system may contain a non-polymer phase-separation enhancing agent to induce phase separation of a protein during cooling. Subtilisin small spherical particles can be formed according to the present invention using a mixture of propylene glycol and ethanol without the use of any polymers. Propylene glycol serves as a freezing point depression agent and ethanol serves as the phase-separation enhancing agent in this system. Propylene glycol also aids in the formation of a spherical shape of the small spherical particles.

A 20 mg/mL subtilisin solution in 35% propylene glycol—10% Formate—0.02% CaCl$_2$ was prepared. The 35% propylene glycol—subtilisin solution was then brought to 67% ethanol while mixing. The solution remained clear at room temperature. However, when cooled to −20° C. for one hour, a suspension of particles formed. After centrifugation to collect the particles and washing with 90% ethanol, Coulter Particle Size analysis was performed, with absolute ethanol as the suspension fluid. The particles yielded Coulter results consistent with discrete particles having an average diameter of 2.2 microns and 95% of the particles were between 0.46 and 3.94 microns. Light microscopy evaluation confirmed these results showing substantially spherical particles. SEM analysis of the particles confirmed the Coulter results.

The retention of subtilisin enzyme activity after conversion of subtilisin in solution to subtilisin small spherical particles was confirmed by a colorimetric assay. The theoretical total units of activity for the small spherical particles were calculated by subtracting the total units found in the supernatant (after separation of the subtilisin particles) from the total units of subtilisin assayed in the ethanol-subtilisin-propylene glycol solution prior to cooling. The actual total units found for the subtilisin small spherical particles divided by the theoretical units expressed as a percentage represents the retention of subtilisin activity after particle formation. By this calculation, 107% of the theoretical subtilisin activity was retained after formation of the subtilisin small spherical particles.

It is to be understood that the embodiments disclosed herein are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner. The embodiments of the present invention which have been described are illustrative of some of the applications of the principles of the present invention, and modifications may be made, including those combinations of features that are individually disclosed or claimed herein.

The invention claimed is:

1. A process of preparing microparticles comprising (a) combining an antibody and a phase separating enhancing agent (PSEA) that is water-soluble or soluble in a water-miscible solvent in an aqueous solution to form a single continuous liquid phase and to provide a substantially amorphous antibody composition, and (b) cooling the composition to a temperature below phase transition temperature of the composition such that microparticles are formed after the composition is at or below the phase transition temperature of the composition and said PSEA remains in a liquid phase, wherein said antibody is at least about 20% of said microparticles by weight and microparticles are formed upon cooling the composition and said microparticles are readily soluble upon injection in a physiological environment.

2. The process of claim 1, further comprising removing said PSEA from the composition.

3. The process of claim 1, wherein said antibody is selected from the group consisting of a monoclonal antibody, a polyclonal antibody, a monoclonal antibody fragment, a trap molecule, a single chain antibody, a recombinant form thereof, and combinations thereof.

4. A process of preparing microparticles comprising (a) combining protein and a phase separating enhancing agent (PSEA) that is water-soluble or soluble in a water-miscible solvent in an aqueous solution to form a single continuous liquid phase and to provide a substantially amorphous protein composition, and (b) cooling the composition to a temperature below phase transition temperature of the composition such that microparticles are formed after the composition is at or below the phase transition temperature of the composition and said PSEA remains in a liquid phase, wherein said protein is at least about 20% of said microparticles by weight and microparticles are formed upon cooling the composition and said microparticles are readily soluble upon injection in a physiological environment.

5. The process of claim 1, further comprising removing said PSEA from the composition.

6. A composition comprising microparticles produced by the method of claim 1, 2, 3, 4, or 5.

7. A pharmaceutical microparticle composition that is injectable at a concentration of at least about 50 mg of protein in said microparticles per ml of said composition through a needle of at least 20 gauge or finer, said microparticle composition comprising substantially amorphous antibody microparticles made by the method of claim 1 or claim 2, said microparticles are optionally associated with a phase separation enhancing agent (PSEA) utilized in preparation of said microparticles, wherein the microparticles are readily soluble upon injection in a physiological environment.

8. The composition of claim 7, wherein said microparticles are non-crystalline.

9. The composition of claim 7, wherein said antibody is a monoclonal antibody.

10. The composition of claim 7, wherein said microparticles are microspheres having a particle size not greater than about 50 microns.

11. The composition of claim 7, wherein said antibody microparticles comprise antibodies selected from the group consisting of monoclonal antibodies, polyclonal antibodies, monoclonal antibody fragments, trap molecules single chain antibodies recombinant forms thereof, and combinations thereof.

12. The composition of claim 7, wherein said antibody has a molecular weight of at least about 25,000 Daltons.

13. The composition of claim 7, wherein said microparticles are encapsulated within a polymer matrix.

14. The composition of claim 7, wherein said microparticles further include an excipient.

15. The composition of claim 7 wherein said composition provides said antibody microparticle at a concentration from about 50 mg per ml to about 400 mg per ml.

16. The composition of claim 15 wherein said antibody is at least about 50% by weight of said microparticles based on the total weight of the microparticles.

17. The composition of claim 15 wherein said antibody is at least about 80% by weight of said microparticles based on the total weight of the microparticles.

18. The composition of claim 15 wherein said antibody is at least about 90% by weight of said microparticles based on the total weight of the microparticles.

19. The composition of claim 7 wherein said composition provides said antibody microparticle at a concentration from at least about 50 mg per ml.

20. The composition of claim 19 wherein said antibody is at least about 50% by weight of said microparticles based on the total weight of the microparticles.

21. The composition of claim 19 wherein said antibody is at least about 80% by weight of said microparticles based on the total weight of the microparticles.

22. The composition of claim 19 wherein said antibody is at least about 90% by weight of said microparticles based on the total weight of the microparticles.

23. The composition of claim 7 wherein said antibody is at least about 50% of said microparticle by weight.

24. The composition of claim 7 wherein said antibody is about 80% of said microparticle by weight.

25. The composition of claim 7 wherein said antibody is at least about 90% of said microparticle by weight.

26. An injectable pharmaceutical composition of microparticles comprising a suspension of substantially amorphous protein microparticles made by the method of claim 4 or claim 5, the composition providing a concentration of at least about 50 mg of protein in said microparticles per ml of said composition, and the protein has a molecular weight of at least about 25,000 Daltons, wherein the microparticles are readily soluble upon injection in a physiological environment, and wherein said microparticles optionally are associated with a phase separation enhancing agent (PSEA) utilized in preparation of said microparticles.

27. The composition of claim 26, wherein said protein microparticles comprise antibodies.

28. The composition of claim 26, wherein said protein microparticles comprise monoclonal antibodies.

29. The composition of claim 26, wherein said protein microparticles are microspheres.

30. The composition of claim 26, wherein said protein microparticles are noncrystalline.

31. The composition of claim 26, wherein said protein microparticles comprise antibodies selected from the group consisting of monoclonal antibodies, polyclonal antibodies, antibody fragments, trap molecules, single chain antibodies, recombinant forms thereof, and combinations thereof.

32. The composition of claim 31, wherein a dose of said composition protein is dispersed in not greater than about 10 ml of said composition.

33. The composition of claim 31, wherein said microparticles have an average particle size of not greater than about 50 microns, and the injectable composition passes through an injection needle of 20 gauge or finer.

34. The composition of claim 26, wherein a clinically effective dose of said composition protein is dispersed in not greater than about 10 ml of said composition.

35. The composition of claim 26, wherein said microparticles exhibit a rate of dissolution upon injection that is faster than crystalline microparticles having an average particle size of not greater than about 50 microns, and the injectable composition passes through an injection needle of 20 gauge or finer.

36. The composition of claim 26, wherein at least about 90 percent of the protein is chemically intact as said protein in the microparticles.

37. The composition of claim 26, wherein said microparticles are encapsulated.

38. The composition of claim 37, wherein said microparticles are encapsulated within a matrix.

39. The composition of claim 37, wherein said microparticles further include an excipient.

40. The composition of claim 26 wherein said composition provides said protein microparticles at a concentration from about 50 mg per ml to about 400 mg per ml.

41. The composition of claim 40 wherein said protein is at least about 50% by weight of said microparticles based on the total weight of the microparticles.

42. The composition of claim 40 wherein said protein is at least about 80% by weight of said microparticles based on the total weight of the microparticles.

43. The composition of claim 40 wherein said protein is at least about 90% by weight of said microparticles based on the total weight of the microparticles.

44. The composition of claim 26 wherein said composition provides said protein microparticles at a concentration from at least about 50 mg per ml.

45. The composition of claim 44 wherein said protein is at least about 50% by weight of said microparticles based on the total weight of the microparticles.

46. The composition of claim 44 wherein said protein is at least about 80% by weight of said microparticles based on the total weight of the microparticles.

47. The composition of claim 44 wherein said protein is at least about 90% by weight of said microparticles based on the total weight of the microparticles.

48. The composition of claim 26 wherein said protein is at least about 50% by weight of said microparticles based on the total weight of the microparticles.

49. The composition of claim 26 wherein said protein is at least about 80% by weight of said microparticles based on the total weight of the microparticles.

50. The composition of claim 26 wherein said protein is at least about 90% by weight of said microparticles based on the total weight of the microparticles.

51. The composition of claim 26 wherein said suspension of microparticles is injectable under clinically acceptable conditions of time and force.

52. The composition of claim 26 wherein one ml of said suspension of microparticles is injectable in less than about 45 seconds under clinically acceptable conditions of force.

53. The composition of claim 26 wherein one ml of said suspension of microparticles is injectable in less than about 30 seconds under clinically acceptable conditions of force.

54. A method for administering the pharmaceutical microparticle composition of claim 7 said method comprising:
    loading said microparticle composition into a syringe unit having a fine gauge needle as a suspension of not greater than about 10 ml and at a concentration of at least about 50 mg of antibody in said microparticles per ml of composition; and
    administering the micorparticle composition to an individual by injecting the microparticle composition through said syringe, wherein the microparticles are readily soluble upon injection in a physiological environment.

55. The method of claim 54, wherein said antibody is selected from the group consisting of a monoclonal antibody, a polyclonal antibody, a monoclonal antibody fragment, a trap molecule, a single chain antibody, a recombinant form thereof, and combinations thereof.

56. The method of claim 54, wherein the needle of the loading and administering is 20 gauge or finer.

57. The method of claim 54 wherein said composition provides said antibody at a concentration from about 50 mg per ml to about 400 mg per ml.

58. The method of claim 57 wherein said antibody is at least about 50% by weight of said microparticles based on the total weight of the microparticles.

59. The method of claim 57 wherein said antibody is at least about 80% by weight of said microparticles based on the total weight of the microparticles.

60. The method of claim 57 wherein said antibody is at least about 90% by weight of said microparticles based on the total weight of the microparticles.

61. The method of claim 54 wherein said microparticles are at a concentration from at least about 50 mg per ml.

62. The method of claim 61 wherein said antibody is at least about 50% by weight of said microparticles based on the total weight of the microparticles.

63. The method of claim 61 wherein said antibody is at least about 80% by weight of said microparticles based on the total weight of the microparticles.

64. The method of claim 61 wherein said antibody is at least about 90% by weight of said microparticles based on the total weight of the microparticles.

65. The method of claim 54 wherein said antibody is at least about 50% by weight of said microparticle, based on the total weight of the microparticle.

66. The method of claim 54 wherein said antibody is at least about 80% by weight of said microparticle, based on the total weight of the microparticle.

67. The method of claim 54 wherein said antibody is at least about 90% by weight of said microparticle, based on the total weight of the microparticle.

68. A method for administering the pharmaceutical microparticle composition of claim 26 said method comprising:

loading said microparticle composition into a syringe unit having a fine gauge needle as a suspension of not greater than about 10 ml at a concentration of at least about 50 mg of high molecular weight protein in said microparticles per ml of composition; and administering the micorparticle composition to an individual by injecting the microparticle composition through said syringe, wherein the microparticles are readily soluble upon injection in a physiological environment.

69. The method of claim 68, wherein said high molecular weight protein is selected from the group consisting of a monoclonal antibody, a polyclonal antibody, a monoclonal antibody fragment, a trap molecule, a single chain antibody, a recombinant form thereof, and combinations thereof.

70. The method of claim 68, wherein the needle of the loading and administering is 20 gauge or finer.

71. The method of claim 68 wherein said microparticles are at a concentration from about 50 mg per ml to about 400 mg per ml.

72. The method of claim 71 wherein said protein is at least about 50% by weight of said microparticles based on the total weight of the microparticles.

73. The method of claim 71 wherein said protein is at least about 80% by weight of said microparticles based on the total weight of the microparticles.

74. The method of claim 71 wherein said protein is at least about 90% by weight of said microparticles based on the total weight of the microparticles.

75. The method of claim 68 wherein said microparticles are at a concentration from at least about 50 mg per ml.

76. The method of claim 75 wherein said protein is at least about 50% by weight of said microparticles based on the total weight of the microparticles.

77. The method of claim 75 wherein said protein is at least about 80% by weight of said microparticles based on the total weight of the microparticles.

78. The method of claim 75 wherein said protein is at least about 90% by weight of said microparticles based on the total weight of the microparticles.

79. The method of claim 68 wherein said protein is at least about 50% by weight of said microparticle, based on the total weight of the microparticle.

80. The method of claim 68 wherein said protein is at least about 80% by weight of said microparticle, based on the total weight of the microparticle.

81. The method of claim 68 wherein said protein is at least about 90% by weight of said microparticle, based on the total weight of the microparticle.

* * * * *